US007550145B2

(12) United States Patent
O'Hagan et al.

(10) Patent No.: US 7,550,145 B2
(45) Date of Patent: Jun. 23, 2009

(54) ADJUVANT COMPOSITIONS

(75) Inventors: Derek O'Hagan, Berkeley, CA (US); Nicholas Valiante, Fremont, CA (US)

(73) Assignee: Novarttis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 10/265,083

(22) Filed: Oct. 3, 2002

(65) Prior Publication Data

US 2003/0170273 A1  Sep. 11, 2003

Related U.S. Application Data

(60) Provisional application No. 60/326,929, filed on Oct. 3, 2001, provisional application No. 60/373,547, filed on Apr. 17, 2002.

(51) Int. Cl.
*A61K 39/29* (2006.01)
(52) U.S. Cl. ............... 424/184.1; 424/218.1; 424/278.1
(58) Field of Classification Search .............. 424/184.1, 424/204.1, 208.1, 228.1, 250.1, 130.1, 450, 424/489; 536/23.1, 23.72, 23.7
See application file for complete search history.

(56) References Cited

U.S. PATENT DOCUMENTS

| | | | |
|---|---|---|---|
| 3,906,092 A * | 9/1975 | Hilleman et al. .......... 424/209.1 |
| 5,384,133 A | 1/1995 | Boyes et al. |
| 5,712,257 A | 1/1998 | Carter |
| 5,739,118 A * | 4/1998 | Carrano et al. ............... 514/44 |
| 5,906,980 A | 5/1999 | Carter |
| 6,086,901 A * | 7/2000 | O'Hagan et al. .......... 424/283.1 |
| 6,150,087 A * | 11/2000 | Chien ............................ 435/5 |
| 6,218,371 B1 | 4/2001 | Krieg et al. |
| 6,239,116 B1 | 5/2001 | Krieg et al. |
| 6,299,884 B1 | 10/2001 | Van Nest et al. |
| 6,306,405 B1 | 10/2001 | O'Hagan et al. |
| 6,451,325 B1 | 9/2002 | Van Nest et al. |
| 6,458,370 B1 | 10/2002 | O'Hagan et al. |
| 6,855,492 B2 | 2/2005 | O'Hagan et al. |
| 6,861,410 B1 | 3/2005 | Ott et al. |
| 6,884,435 B1 | 4/2005 | O'Hagan et al. |

FOREIGN PATENT DOCUMENTS

| | | |
|---|---|---|
| EP | 0 991 403 B1 | 2/2003 |
| EP | 1 156 781 B1 | 8/2005 |
| WO | WO 90/14837 A1 | 12/1990 |
| WO | WO 98/33487 A1 | 8/1998 |
| WO | WO 99/02132 A2 * | 1/1999 |
| WO | WO 99/30737 A1 | 6/1999 |
| WO | WO 00/06123 A1 * | 2/2000 |
| WO | WO 00/15768 A1 | 3/2000 |
| WO | WO 00/67787 A2 | 5/2000 |
| WO | WO 00/50006 A2 | 8/2000 |
| WO | WO 01/36599 A1 | 5/2001 |

OTHER PUBLICATIONS

Pizza et al. Identification of Vaccine Candidates Against Serogroup B Meningococcus by Whole-Genome Sequencing, Science, Mar. 10, 2000, vol. 287, pp. 1816-1820.*
Le Bon et al., "Type I interferons potently enhance humoral immunity and can promote isotype switching by stimulating dendritic cells in vivo," *Immunity* 14:461-470, 2001.
Majde, "Viral double-stranded RNA, cytokines, and the flu," *J. Interferon and Cytokine Research* 20:259-272, 2000.
Ott et al., "MF59—Design and evaluation of a safe and potent adjuvant for human vaccines," in *Vaccine Design: The Subunit and Adjuvant Approach* (Powell, M.F. and Newman, M.J. eds.) Plenum Press, New York, 1995, pp. 277-296.
Singh et al., "Cationic microparticles: a potent delivery system for DNA vaccines," *PNAS* 97(2):811-816, 2000.
Tazulakhova et al., "Russian experience in screening, analysis, and clinical application of novel interferon inducers," *J. Interferon and Cytokine Research* 21:65-73, 2001.
Cella, et al., "Maturation, Activation, and Protection of Dendritic Cells Induced by Double-Stranded RNA," *J Exp Med* 189(5):821-829 (1999).
Dupuis, et al., "Dendritic Cells Internalize Vaccine Adjuvant After Intramuscular Injection," *Cellular Immunology* 186:18-27 (1998).
McCluskie, et al., CpG DNA is an Effective Oral Adjutant to Protein Antigens in Mice, *Vaccine* 19:950-957 (2001).
Moss, et al., "In Vitro Immune Function After Vaccination with an Inactivated gp 120 Depleted HIV-1 Antigen with Immunostimulatory Oligonucleotides," *Vaccine* 18:1081-1087 (2000).
Moss, et al., "Human Immunodeficiency Virus (HIV)-Specific Immune Responses are Generated with the Simultaneous Vaccination of gp 120-Depleted Whole-Killed HIV-1 Immunogen with Cytosine-Phosphorothioate-Guanine Dinucleotide Immunostimulatory Sequence of DNA," *J Hum Virol* 4:39-43 (2001).
O'Hagan, et al., "Synergistic Adjuvant Activity of Immunostimulatory DNA Oil/Water Emulsions for Immunization with HIV p55 Gag Antigen," *Vaccine* 20:3389-3398 (2002).
O'Hagan, et al., "Microparticles in MF59, A Potent Adjuvant Combination for a Recombinant Protein Vaccine Against HIV-1," *Vaccine* 18:1793-1801 (2000).
Parkin, et al., "An Overview of the Immune System," *The Lancet* 357:1777-1789 (2001).
Singh, et al., "Advances in Vaccine Adjuvants," *Nature Biotechnol* 17(11):1075-1081 (1999).

* cited by examiner

*Primary Examiner*—Stacy B Chen
(74) *Attorney, Agent, or Firm*—Helen Lee; Roberta Robins; Robert Gorman

(57) ABSTRACT

Adjuvant compositions comprising type 1 interferon inducers, such as double-stranded RNA, in combination with antigen delivery systems and/or immunostimulatory molecules, such as immunostimulatory nucleic acid sequences, for enhancing the immune response of a coadministered antigen, are described.

9 Claims, 10 Drawing Sheets

```
                                                              MATURE E1
SerPheSerIlePheLeuLeuAlaLeuLeuSerCysLeuThrValProAlaSerAlaTyr  192
TCTTTCTCTATCTTCCTTCTGGCCCTGCTCTCTTGCTTGACTGTGCCCGCTTCGGCCTAC
AGAAAGAGATAGAAGGAAGACCGGGACGAGAGAACGAACTGACACGGGCGAAGCCGGATG

GlnValArgAsnSerThrGlyLeuTyrHisValThrAsnAspCysProAsnSerSerIle  212
CAAGTGCGCAACTCCACGGGGCTCTACCACGTCACCAATGATTGCCCTAACTCGAGTATT
GTTCACGCGTTGAGGTGCCCCGAGATGGTGCAGTGGTTACTAACGGGATTGAGCTCATAA

ValTyrGluAlaAlaAspAlaIleLeuHisThrProGlyCysValProCysValArgGlu  232
GTGTACGAGGCGGCCGATGCCATCCTGCACACTCCGGGGTGCGTCCCTTGCGTTCGCGAG
CACATGCTCCGCCGGCTACGGTAGGACGTGTGAGGCCCCACGCAGGGAACGCAAGCGCTC

GlyAsnAlaSerArgCysTrpValAlaMetThrProThrValAlaThrArgAspGlyLys  252
GGCAACGCCTCGAGGTGTTGGGTGGCGATGACCCCTACGGTGGCCACCAGGGATGGCAAA
CCGTTGCGGAGCTCCACAACCCACCGCTACTGGGGATGCCACCGGTGGTCCCTACCGTTT

LeuProAlaThrGlnLeuArgArgHisIleAspLeuLeuValGlySerAlaThrLeuCys  272
CTCCCCGCGACGCAGCTTCGACGTCACATCGATCTGCTTGTCGGGAGCGCCACCCTCTGT
GAGGGGCGCTGCGTCGAAGCTGCAGTGTAGCTAGACGAACAGCCCTCGCGGTGGGAGACA

SerAlaLeuTyrValGlyAspLeuCysGlySerValPheLeuValGlyGlnLeuPheThr  292
TCGGCCCTCTACGTGGGGGACCTGTGCGGGTCTGTCTTTCTTGTCGGCCAACTGTTTACC
AGCCGGGAGATGCACCCCCTGGACACGCCCAGACAGAAAGAACAGCCGGTTGACAAATGG

PheSerProArgArgHisTrpThrThrGlnGlyCysAsnCysSerIleTyrProGlyHis  312
TTCTCTCCCAGGCGCCACTGGACGACGCAAGGTTGCAATTGCTCTATCTATCCCGGCCAT
AAGAGAGGGTCCGCGGTGACCTGCTGCGTTCCAACGTTAACGAGATAGATAGGGCCGGTA

IleThrGlyHisArgMetAlaTrpAspMetMetMetAsnTrpSerProThrThrAlaLeu  332
ATAACGGGTCACCGCATGGCATGGGATATGATGATGAACTGGTCCCCTACGACGGCGTTG
TATTGCCCAGTGGCGTACCGTACCCTATACTACTACTTGACCAGGGGATGCTGCCGCAAC

ValMetAlaGlnLeuLeuArgIleProGlnAlaIleLeuAspMetIleAlaGlyAlaHis  352
GTAATGGCTCAGCTGCTCCGGATCCCACAAGCCATCTTGGACATGATCGCTGGTGCTCAC
CATTACCGAGTCGACGAGGCCTAGGGTGTTCGGTAGAACCTGTACTAGCGACCACGAGTG

TrpGlyValLeuAlaGlyIleAlaTyrPheSerMetValGlyAsnTrpAlaLysValLeu  372
TGGGGAGTCCTGGCGGGCATAGCGTATTTCTCCATGGTGGGGAACTGGGCGAAGGTCCTG
ACCCCTCAGGACCGCCCGTATCGCATAAAGAGGTACCACCCCTTGACCCGCTTCCAGGAC
                             E2
ValValLeuLeuLeuPheAlaGlyValAspAlaGluThrHisValThrGlyGlySerAla  392
GTAGTGCTGCTGCTATTTGCCGGCGTCGACGCGGAAACCCACGTCACCGGGGGAAGTGCC
CATCACGACGACGATAAACGGCCGCAGCTGCGCCTTTGGGTGCAGTGGCCCCCTTCACGG

GlyHisThrValSerGlyPheValSerLeuLeuAlaProGlyAlaLysGlnAsnValGln  412
GGCCACACTGTGTCTGGATTTGTTAGCCTCCTCGCACCAGGCGCCAAGCAGAACGTCCAG
CCGGTGTGACACAGACCTAAACAATCGGAGGAGCGTGGTCCGCGGTTCGTCTTGCAGGTC
```

FIGURE 1A

```
LeuIleAsnThrAsnGlySerTrpHisLeuAsnSerThrAlaLeuAsnCysAsnAspSer   432
CTGATCAACACCAACGGCAGTTGGCACCTCAATAGCACGGCCCTGAACTGCAATGATAGC
GACTAGTTGTGGTTGCCGTCAACCGTGGAGTTATCGTGCCGGGACTTGACGTTACTATCG

LeuAsnThrGlyTrpLeuAlaGlyLeuPheTyrHisHisLysPheAsnSerSerGlyCys   452
CTCAACACCGGCTGGTTGGCAGGGCTTTTCTATCACCACAAGTTCAACTCTTCAGGCTGT
GAGTTGTGGCCGACCAACCGTCCCGAAAAGATAGTGGTGTTCAAGTTGAGAAGTCCGACA

ProGluArgLeuAlaSerCysArgProLeuThrAspPheAspGlnGlyTrpGlyProIle   472
CCTGAGAGGCTAGCCAGCTGCCGACCCCTTACCGATTTTGACCAGGGCTGGGGCCCTATC
GGACTCTCCGATCGGTCGACGGCTGGGGAATGGCTAAAACTGGTCCCGACCCCGGGATAG

SerTyrAlaAsnGlySerGlyProAspGlnArgProTyrCysTrpHisTyrProProLys   492
AGTTATGCCAACGGAAGCGGCCCCGACCAGCGCCCTACTGCTGGCACTACCCCCCAAAA
TCAATACGGTTGCCTTCGCCGGGGCTGGTCGCGGGGATGACGACCGTGATGGGGGGTTTT

ProCysGlyIleValProAlaLysSerValCysGlyProValTyrCysPheThrProSer   512
CCTTGCGGTATTGTGCCCGCGAAGAGTGTGTGTGGTCCGGTATATTGCTTCACTCCCAGC
GGAACGCCATAACACGGGCGCTTCTCACACACACCAGGCCATATAACGAAGTGAGGGTCG

ProValValValGlyThrThrAspArgSerGlyAlaProThrTyrSerTrpGlyGluAsn   532
CCCGTGGTGGTGGGAACGACCGACAGGTCGGGCGCGCCCACCTACAGCTGGGGTGAAAAT
GGGCACCACCACCCTTGCTGGCTGTCCAGCCCGCGCGGGTGGATGTCGACCCCACTTTTA

AspThrAspValPheValLeuAsnAsnThrArgProProLeuGlyAsnTrpPheGlyCys   552
GATACGGACGTCTTCGTCCTTAACAATACCAGGCCACCGCTGGGCAATTGGTTCGGTTGT
CTATGCCTGCAGAAGCAGGAATTGTTATGGTCCGGTGGCGACCCGTTAACCAAGCCAACA

ThrTrpMetAsnSerThrGlyPheThrLysValCysGlyAlaProProCysValIleGly   572
ACCTGGATGAACTCAACTGGATTCACCAAAGTGTGCGGAGCGCCTCCTTGTGTCATCGGA
TGGACCTACTTGAGTTGACCTAAGTGGTTTCACACGCCTCGCGGAGGAACACAGTAGCCT

GlyAlaGlyAsnAsnThrLeuHisCysProThrAspCysPheArgLysHisProAspAla   592
GGGGCGGGCAACAACACCCTGCACTGCCCCACTGATTGCTTCCGCAAGCATCCGGACGCC
CCCCGCCCGTTGTTGTGGGACGTGACGGGGTGACTAACGAAGGCGTTCGTAGGCCTGCGG

ThrTyrSerArgCysGlySerGlyProTrpIleThrProArgCysLeuValAspTyrPro   612
ACATACTCTCGGTGCGGCTCCGGTCCCTGGATCACACCCAGGTGCCTGGTCGACTACCCG
TGTATGAGAGCCACGCCGAGGCCAGGGACCTAGTGTGGGTCCACGGACCAGCTGATGGGC

TyrArgLeuTrpHisTyrProCysThrIleAsnTyrThrIlePheLysIleArgMetTyr   632
TATAGGCTTTGGCATTATCCTTGTACCATCAACTACACTATATTTAAAATCAGGATGTAC
ATATCCGAAACCGTAATAGGAACATGGTAGTTGATGTGATATAAATTTTAGTCCTACATG

ValGlyGlyValGluHisArgLeuGluAlaAlaCysAsnTrpThrArgGlyGluArgCys   652
GTGGGAGGGGTCGAGCACAGGCTGGAAGCTGCCTGCAACTGGACGCGGGGCGAACGTTGC
CACCCTCCCCAGCTCGTGTCCGACCTTCGACGGACGTTGACCTGCGCCCCGCTTGCAACG

AspLeuGluAspArgAspArgSerGluLeuSerProLeuLeuLeuThrThrThrGlnTrp   672
GATCTGGAAGATAGGGACAGGTCCGAGCTCAGCCCGTTACTGCTGACCACTACACAGTGG
CTAGACCTTCTATCCCTGTCCAGGCTCGAGTCGGGCAATGACGACTGGTGATGTGTCACC
```

FIGURE 1B

```
GlnValLeuProCysSerPheThrThrLeuProAlaLeuSerThrGlyLeuIleHisLeu  692
CAGGTCCTCCCGTGTTCCTTCACAACCCTGCCAGCCTTGTCCACCGGCCTCATCCACCTC
GTCCAGGAGGGCACAAGGAAGTGTTGGGACGGTCGGAACAGGTGGCCGGAGTAGGTGGAG

HisGlnAsnIleValAspValGlnTyrLeuTyrGlyValGlySerSerIleAlaSerTrp  712
CACCAGAACATTGTGGACGTGCAGTACTTGTACGGGGTGGGGTCAAGCATCGCGTCCTGG
GTGGTCTTGTAACACCTGCACGTCATGAACATGCCCCACCCCAGTTCGTAGCGCAGGACC

AlaIleLysTrpGluTyrValValLeuLeuPheLeuLeuLeuAlaAspAlaArgValCys  732
GCCATTAAGTGGGAGTACGTCGTCCTCCTGTTCCTTCTGCTTGCAGACGCGCGCGTCTGC
CGGTAATTCACCCTCATGCAGCAGGAGGACAAGGAAGACGAACGTCTGCGCGCGCAGACG

P7
SerCysLeuTrpMetMetLeuLeuIleSerGlnAlaGluAlaAlaLeuGluAsnLeuVal  752
TCCTGCTTGTGGATGATGCTACTCATATCCCAAGCGGAAGCGGCTTTGGAGAACCTCGTA
AGGACGAACACCTACTACGATGAGTATAGGGTTCGCCTTCGCCGAAACCTCTTGGAGCAT

IleLeuAsnAlaAlaSerLeuAlaGlyThrHisGlyLeuValSerPheLeuValPhePhe  772
ATACTTAATGCAGCATCCCTGGCCGGGACGCACGGTCTTGTATCCTTCCTCGTGTTCTTC
TATGAATTACGTCGTAGGGACCGGCCCTGCGTGCCAGAACATAGGAAGGAGCACAAGAAG

CysPheAlaTrpTyrLeuLysGlyLysTrpValProGlyAlaValTyrThrPheTyrGly  792
TGCTTTGCATGGTATCTGAAGGGTAAGTGGGTGCCCGGAGCGGTCTACACCTTCTACGGG
ACGAAACGTACCATAGACTTCCCATTCACCCACGGGCCTCGCCAGATGTGGAAGATGCCC

MetTrpProLeuLeuLeuLeuLeuLeuAlaLeuProGlnArgAlaTyrAlaOC         809
ATGTGGCCTCTCCTCCTGCTCCTGTTGGCGTTGCCCCAGCGGGCGTACGCGTAA
TACACCGGAGAGGAGGACGAGGACAACCGCAACGGGGTCGCCCGCATGCGCATT
```

FIGURE 1C

```
tggaagggtt aatttactcc aagaaaaggc aagaaatcct tgatttgtgg gtctatcaca  60
cacaaggctt cttccctgat tggcaaaact acacaccggg gccaggggtc agatatccac 120
tgacctttgg atggtgctac aagctagtgc cagttgaccc aggggaggtg gaagaggcca 180
acggaggaga agacaactgt ttgctacacc ctatgagcca acatggagca gaggatgaag 240
atagagaagt attaaagtgg aagtttgaca gcctcctagc acgcagacac atggcccgcg 300
agctacatcc ggagtattac aaagactgct gacacagaag ggactttccg cctgggactt 360
tccactgggg cgttccggga ggtgtggtct gggcgggact gggagtggt caaccctcag 420
atgctgcata taagcagctg cttttcgcct gtactgggtc tctctcggta gaccagatct 480
gagcctggga gccctctggc tatctaggga acccactgct taagcctcaa taaagcttgc 540
cttgagtgct ttaagtagtg tgtgcccatc tgttgtgtga ctctggtaac tagagatccc 600
tcagaccctt tgtggtagtg tggaaaatct ctagcagtgg cgcccgaaca gggaccagaa 660
agtgaaagtg agaccagagg agatctctcg acgcaggact cggcttgctg aagtgcacac 720
ggcaagaggc gagaggggcg gctggtgagt acgccaattt tacttgacta gcggaggcta 780
gaaggagaga gatgggtgcg agagcgtcaa tattaagcgg cggaaaatta gataaatggg 840
aaagaattag gttaaggcca gggggaaaga aacattatat gttaaaacat ctagtatggg 900
caagcaggga gctggaaaga tttgcactta accctggcct gttagaaaca tcagaaggct 960
gtaaacaaat aataaaacag ctacaaccag ctcttcagac aggaacagag gaacttagat 1020
cattattcaa cacagtagca actctctatt gtgtacataa agggatagag gtacgagaca 1080
ccaaggaagc cttagacaag atagaggaag aacaaaacaa atgtcagcaa aaagcacaac 1140
aggcaaaagc agctgacgaa aaggtcagtc aaaattatcc tatagtacag aatgcccaag 1200
ggcaaatggt acaccaagct atatcaccta gaacattgaa tgcatggata aaagtaatag 1260
aggaaaaggc tttcaatcca gaggaaatac ccatgtttac agcattatca gaaggagcca 1320
ccccacaaga tttaaacaca atgttaaata cagtgggggg acatcaagca gccatgcaaa 1380
tgttaaaaga taccatcaat gaggaggctg cagaatggga taggacacat ccagtacatg 1440
cagggcctgt tgcaccaggc cagatgagag aaccaagggg aagtgacata gcaggaacta 1500
ctagtaccct tcaggaacaa atagcatgga tgacaagtaa tccacctatt ccagtagaag 1560
acatctataa aagatggata attctggggt taaataaaat agtaagaatg tatagccctg 1620
ttagcatttt ggacataaaa caagggccaa agaacccctt tagagactat gtagaccggt 1680
tctttaaaac cttaagagct gaacaagcta cacaagatgt aaagaattgg atgacagaca 1740
ccttgttggt ccaaaatgcg aacccagatt gtaagaccat tttaagagca ttaggaccag 1800
gggcctcatt agaagaaatg atgacagcat gtcagggagt gggaggacct agccataaag 1860
caagagtgtt ggctgaggca atgagccaag caaacagtaa catactagtg cagagaagca 1920
attttaaagg ctctaacaga attattaaat gtttcaactg tggcaaagta gggcacatag 1980
ccagaaattg cagggcccct aggaaaaagg gctgttggaa atgtggacag gaaggacacc 2040
aaatgaaaga ctgtactgag aggcaggcta atttttagg gaaaatttgg ccttcccaca 2100
aggggaggcc agggaatttc ctccagaaca gaccagagcc aacagcccca ccagcagaac 2160
caacagcccc accagcagag agcttcaggt tcgaggagac aaccccgtg ccgaggaagg 2220
agaaagagag ggaacctta acttccctca aatcactctt tggcagcgac cccttgtctc 2280
aataaaagta gagggccaga taaaggaggc tctcttagac acaggagcag atgatacagt 2340
attagaagaa atagatttgc agggaaatg gaaaccaaaa atgataggg gaattggagg 2400
ttttatcaaa gtaagacagt atgatcaaat acttatagaa atttgtggaa aaaggctat 2460
aggtacagta ttagtaggc ctacaccagt caacataatt ggaagaaatc tgttaactca 2520
gcttggatgc acactaaatt ttccaattag tcctattgaa actgtaccag taaaattaaa 2580
accaggaatg gatggcccaa aggtcaaaca atggccattg acagaagaaa aataaaagc 2640
attaacagca atttgtgagg aaatggagaa ggaaggaaaa attacaaaaa ttgggcctga 2700
taatccatat aacactccag tatttgccat aaaaagaag gacagtacta agtggagaaa 2760
attagtagat ttcagggaac tcaataaaag aactcaagac ttttggaag ttcaattagg 2820
aataccacac ccagcaggat taaaaagaa aaaatcagtg acagtgctag atgtggggga 2880
tgcatatttt tcagttcctt tagatgaaag cttcaggaaa tatactgcat tcaccatacc 2940
```

FIGURE 5A

```
tagtataaac aatgaaacac cagggattag atatcaatat aatgtgctgc cacagggatg 3000
gaaaggatca ccagcaatat tccagagtag catgacaaaa atcttagagc ccttcagagc 3060
aaaaaatcca gacatagtta tctatcaata tatggatgac ttgtatgtag gatctgactt 3120
agaaataggg caacatagag caaaaataga agagttaagg gaacatttat tgaaatgggg 3180
atttacaaca ccagacaaga aacatcaaaa agaaccccca tttctttgga tggggtatga 3240
actccatcct gacaaatgga cagtacaacc tatactgctg ccagaaaagg atagttggac 3300
tgtcaatgat atacagaagt tagtgggaaa attaaactgg gcaagtcaga tttacccagg 3360
gattaaagta aggcaactct gtaaactcct caggggggcc aaagcactaa cagacatagt 3420
accactaact gaagaagcag aattagaatt ggcagagaac agggaaattt taagagaacc 3480
agtacatgga gtatattatg atccatcaaa agacttgata gctgaaatac agaaacaggg 3540
gcatgaacaa tggacatatc aaatttatca agaaccattt aaaaatctga aacagggaa 3600
gtatgcaaaa atgaggacta cccacactaa tgatgtaaaa cagttaacag aggcagtgca 3660
aaaaatagcc atggaaagca tagtaatatg gggaaagact cctaaattta gactacccat 3720
ccaaaaagaa acatgggaga catggtggac agactattgg caagccacct ggatccctga 3780
gtgggagttt gttaataccc ctcccctagt aaaattatgg taccaactag aaaaagatcc 3840
catagcagga gtagaaactt tctatgtaga tggagcaact aatagggaag ctaaaatagg 3900
aaaagcaggg tatgttactg acagaggaag gcagaaaatt gttactctaa ctaacacaac 3960
aaatcagaag actgagttac aagcaattca gctagctctg caggattcag gatcagaagt 4020
aaacatagta acagactcac agtatgcatt aggaatcatt caagcacaac cagataagag 4080
tgactcagag atatttaacc aaataataga acagttaata aacaaggaaa gaatctacct 4140
gtcatgggta ccagcacata aaggaattgg gggaaatgaa caagtagata aattagtaag 4200
taagggaatt aggaaagtgt tgtttctaga tggaatagat aaagctcaag aagagcatga 4260
aaggtaccac agcaattgga gagcaatggc taatgagttt aatctgccac ccatagtagc 4320
aaaagaaata gtagctagct gtgataaatg tcagctaaaa ggggaagcca tacatggaca 4380
agtcgactgt agtccaggga tatggcaatt agattgtacc catttagagg gaaaaatcat 4440
cctggtagca gtccatgtag ctagtggcta catggaagca gaggttatcc cagcagaaac 4500
aggacaagaa acagcatatt ttatattaaa attagcagga agatggccag tcaaagtaat 4560
acatacagac aatggcagta atttaccag tactgcagtt aaggcagcct gttggtgggc 4620
aggtatccaa caggaatttg gaattcccta caatcccaa agtcagggag tggtagaatc 4680
catgaataaa gaattaaaga aaataatagg acaagtaaga gatcaagctg agcaccttaa 4740
gacagcagta caaatggcag tattcattca caattttaaa agaaaggggg gaattggggg 4800
gtacagtgca ggggaaagaa taatagacat aatagcaaca gacatacaaa ctaaagaatt 4860
acaaaaacaa attataagaa ttcaaaattt tcgggtttat tacagagaca gcagagaccc 4920
tatttggaaa ggaccagccg aactactctg gaaaggtgaa ggggtagtag taatagaaga 4980
taaaggtgac ataaaggtag taccaaggag gaaagcaaaa atcattagag attatgaaaa 5040
acagatggca ggtgctgatt gtgtggcagg tggacaggat gaagattaga gcatggaata 5100
gtttagtaaa gcaccatatg tatatatcaa ggagagctag tggatgggtc tacagacatc 5160
attttgaaag cagacatcca aaagtaagtt cagaagtaca tatcccatta ggggatgcta 5220
gattagtaat aaaaacatat ggggtttgc agacaggaga aagagattgg catttgggtc 5280
atggagtctc catagaatgg agactgagag aatacagcac acaagtagac cctgacctgg 5340
cagaccagct aattcacatg cattattttg attgttttac agaatctgcc ataagacaag 5400
ccatattagg acacatagtt tttcctaggt gtgactatca agcaggacat aagaaggtag 5460
gatctctgca atacttggca ctgacagcat tgataaaacc aaaaaagaga aagccacctc 5520
tgcctagtgt tagaaaatta gtagaggata gatggaacga ccccagaag accagggcc 5580
gcagagggaa ccatacaatg aatggacact agagattcta gaagaactca gcaggaagc 5640
tgtcagacac tttcctagac catggctcca tagcttagga caatatatct atgaaaccta 5700
tggggatact tggacgggag ttgaagctat aataagagta ctgcaacaac tactgttcat 5760
tcatttcaga attggatgcc aacatagcag aataggcatc ttgcgacaga gaagagcaag 5820
aaatggagcc agtagatcct aaactaaagc cctggaacca tccaggaagc caacctaaaa 5880
cagcttgtaa taattgcttt tgcaaacact gtagctatca ttgtctagtt tgctttcaga 5940
caaaaggttt aggcatttcc tatggcagga agaagcggag acagcgacga agcgctcctc 6000
```

FIGURE 5B

```
caagtggtga agatcatcaa aatcctctat caaagcagta agtacacata gtagatgtaa 6060
tggtaagttt aagtttattt aaaggagtag attatagatt aggagtagga gcattgatag 6120
tagcactaat catagcaata atagtgtgga ccatagcata tatagaatat aggaaattgg 6180
taagacaaaa gaaaatagac tggttaatta aaagaattag ggaaagagca gaagacagtg 6240
gcaatgagag tgatggggac acagaagaat tgtcaacaat ggtggatatg gggcatctta 6300
ggcttctgga tgctaatgat ttgtaacacg gaggacttgt gggtcacagt ctactatggg 6360
gtacctgtgt ggagagaagc aaaaactact ctattctgtg catcagatgc taaagcatat 6420
gagacagaag tgcataatgt ctgggctaca catgcttgtg tacccacaga ccccaaccca 6480
caagaaatag ttttgggaaa tgtaacagaa aattttaata tgtggaaaaa taacatggca 6540
gatcagatgc atgaggatat aatcagttta tgggatcaaa gcctaaagcc atgtgtaaag 6600
ttgaccccac tctgtgtcac tttaaactgt acagacaa atgttacagg taatagaact 6660
gttacaggta atacaaatga taccaatatt gcaaatgcta catataagta tgaagaaatg 6720
aaaaattgct ctttcaatgc aaccacagaa ttaagagata agaaacataa agagtatgca 6780
ctctttata aacttgatat agtaccactt aatgaaaata gtaacaactt tacatataga 6840
ttaataaatt gcaataccctc aaccataaca caagcctgtc caaggtctc ttttgacccg 6900
attcctatac attactgtgc tccagctgat tatgcgattc taaagtgtaa taataagaca 6960
ttcaatggga caggaccatg ttataatgtc agcacagtac aatgtacaca tggaattaag 7020
ccagtggtat caactcaact actgttaaat ggtagtctag cagaagaagg gataataatt 7080
agatctgaaa atttgacaga gaataccaaa acaataatag tacatcttaa tgaatctgta 7140
gagattaatt gtacaaggcc caacaataat acaaggaaaa gtgtaaggat aggaccagga 7200
caagcattct atgcaacaaa tgacgtaata ggaaacataa gacaagcaca ttgtaacatt 7260
agtacagata gatggaataa aactttacaa caggtaatga aaaattagg agagcatttc 7320
cctaataaaa caataaaatt tgaaccacat gcaggagggg atctagaaat tacaatgcat 7380
agctttaatt gtagaggaga attttctat tgcaatacat caaacctgtt taatagtaca 7440
tactacccta agaatggtac atacaaatac aatggtaatt caagcttacc catcacactc 7500
caatgcaaaa taaaacaaat tgtacgcatg tggcaagggg taggacaagc aatgtatgcc 7560
cctcccattg caggaaacat aacatgtaga tcaaacatca caggaatact attgacacgt 7620
gatgggggat taacaacac aaacaacgac acagaggaga cattcagacc tggaggagga 7680
gatatgaggg ataactggag aagtgaatta tataaatata agtggtaga aattaagcca 7740
ttgggaatag cacccactaa ggcaaaaaga agagtggtgc agagaaaaaa aagagcagtg 7800
ggaataggag ctgtgttcct tgggttcttg ggagcagcag gaagcactat gggcgcagcg 7860
tcaataacgc tgacggtaca ggccagacaa ctgttgtctg gtatagtgca acagcaaagc 7920
aatttgctga aggctataga ggcgcaacag catatgttgc aactcacagt ctggggcatt 7980
aagcagctcc aggcgagagt cctggctata gaaagatacc taaaggatca acagctccta 8040
gggatttggg gctgctctgg aagactcatc tgcaccactg ctgtgccttg aactccagt 8100
tggagtaata aatctgaagc agatatttgg gataacatga cttggatgca gtgggataga 8160
gaaattaata attacacaga acaatattc aggttgcttg aagactcgca aaaccagcag 8220
gaaagaatg aaaaagattt attagaattg gacaagtgga ataatctgtg gaattggttt 8280
gacatatcaa actggctgtg gtatataaaa atattcataa tgatagtagg aggcttgata 8340
ggtttaagaa taatttttgc tgtgctctct atagtgaata gagttaggca gggatactca 8400
cctttgtcat ttcagaccct taccccaagc ccgaggggac tcgacaggct cggaggaatc 8460
gaagaagaag gtggagagca agacagagac agatccatac gattggtgag cggattcttg 8520
tcgcttgcct gggacgatct gcggagcctg tgcctcttca gctaccaccg cttgagagac 8580
ttcatattaa ttgcagtgag gcagtggaa cttctgggac acagcagtct cagggactaa 8640
cagaggggt gggagatcct taagtatctg gaagtcttg tgcagtattg gggtctagag 8700
ctaaaaaga gtgctattag tccgcttgat accatagcaa tagcagtagc tgaaggaaca 8760
gataggatta tagaattggt acaaagaatt tgtagagcta tcctcaacat acctaggaga 8820
ataagacagg gctttgaagc agctttgcta taaatggga ggcaàgtggt caaaacgcag 8880
catagttgga tggcctgcag taagagaaag aatgagaaga actgagccàg cagcagaggg 8940
agtaggagca gcgtctcaag acttagatag acatggggca cttacaagca gcaacacacc 9000
tgctactaat gaagcttgtg cctggctgca agcacaagag gaggacggag atgtaggctt 9060
```

FIGURE 5C

```
tccagtcaga cctcaggtac ctttaagacc aatgacttat aagagtgcag tagatctcag 9120
cttctttta  aaagaaaagg ggggactgga agggttaatt tactctagga aaaggcaaga 9180
aatccttgat ttgtgggtct ataacacaca aggcttcttc cctgattggc aaaactacac 9240
atcggggcca ggggtccgat tcccactgac ctttggatgg tgcttcaagc tagtaccagt 9300
tgacccaagg gaggtgaaag aggccaatga aggagaagac aactgtttgc tacaccctat 9360
gagccaacat ggagcagagg atgaagatag agaagtatta aagtggaagt ttgacagcct 9420
tctagcacac agacacatgg cccgcgagct acatccggag tattacaaag actgctgaca 9480
cagaagggac tttccgcctg ggactttcca ctggggcgtt ccgggaggtg tggtctgggc 9540
gggacttggg agtggtcacc ctcagatgct gcatataagc agctgctttt cgcttgtact 9600
gggtctctct cggtagacca gatctgagcc tgggagctct ctggctatct agggaaccca 9660
ctgcttaggc ctcaataaag cttgccttga gtgctctaag tagtgtgtgc ccatctgttg 9720
tgtgactctg gtaactagag atccctcaga cctttgtgg tagtgtggaa aatctctagc 9780
a                                                                 9781
```

FIGURE 5D

ADJUVANT COMPOSITIONS

CROSS-REFERENCE TO RELATED APPLICATION

This application is related to provisional patent application Ser. No. 60/326,929, filed Oct. 3, 2001, and provisional patent application Ser. No. 60/373,547, filed Apr. 17, 2002, from which applications priority is claimed under 35 USC §119(e)(1) and which applications are incorporated herein by reference in their entireties.

TECHNICAL FIELD

The present invention pertains generally to adjuvant compositions. In particular, the invention relates to the use of adjuvant compositions comprising type 1 interferon inducers, such as double-stranded RNA, in combination with antigen delivery systems and/or immunostimulatory molecules, such as immunostimulatory nucleic acid sequences, for enhancing the immune response of a coadministered antigen. The adjuvant compositions will find use in both prophylactic and therapeutic compositions.

BACKGROUND OF THE INVENTION

Vaccine compositions often include immunological adjuvants to enhance immune responses. For example, Complete Freund's adjuvant (CFA) is a powerful immunostimulatory agent that has been successfully used with many antigens on an experimental basis. CFA includes three components: a mineral oil, an emulsifying agent, and killed mycobacteria, such as *Mycobacterium tuberculosis*. Aqueous antigen solutions are mixed with these components to create a water-in-oil emulsion. Although effective as an adjuvant, CFA causes severe side-effects, including pain, abscess formation and fever, primarily due to the presence of the mycobacterial component. CFA, therefore, is not used in human and veterinary vaccines.

Muramyl dipeptide (MDP) is the minimal unit of the mycobacterial cell wall complex that generates the adjuvant activity observed with CFA. See, e.g., Ellouz et al., *Biochem. Biophys. Res. Commun.* (1974) 59:1317. Several synthetic analogs of MDP have been generated that exhibit a wide range of adjuvant potency and side-effects. For a review of these analogs, see, Chedid et al., *Prog. Allergy* (1978) 25:63. Representative analogs of MDP include threonyl derivatives of MDP (Byars et al., *Vaccine* (1987) 5:223), n-butyl derivatives of MDP (Chedid et al., *Infect. Immun.* 35:417), and a lipophilic derivative of a muramyl tripeptide (Gisler et al., in *Immunomodulations of Microbial Products and Related Synthetic Compounds* (1981) Y. Yamamura and S. Kotani, eds., Excerpta Medica, Amsterdam, p. 167).

One lipophilic derivative of MDP is N-acetylmuramyl-L-alanyl-D-isogluatminyl-L-alanine-2-(1'-2'-dipalmitoyl-sn-glycero-3-huydroxyphosphoryloxy)-ethylamine (MTP-PE). This muramyl tripeptide includes phospholipid tails that allow association of the hydrophobic portion of the molecule with a lipid environment while the muramyl peptide portion associates with the aqueous environment. Thus, the MTP-PE itself is able to act as an emulsifying agent to generate stable oil-in-water emulsions. MTP-PE has been used in an emulsion of 4% squalene with 0.008% TWEEN 80™, termed MTP-PE-LO (low oil), to deliver the herpes simplex virus gD antigen with effective results (Sanchez-Pescador et al., *J. Immunol.* (1988) 141:1720-1727), albeit poor physical stability. Recently, MF59, a safe, highly immunogenic, submicron oil-in-water emulsion which contains 4-5% w/v squalene, 0.5% w/v TWEEN 80™, 0.5% SPAN 85™, and optionally, varying amounts of MTP-PE, has been developed for use in vaccine compositions. See, e.g., Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277-296.

Interferons and other cytokines, such as IFN-1, are normally expressed at low levels but are induced to high levels of expression by a number of stimuli such as viral and bacterial infection. It is now believed that the viral product responsible for cytokine production is double-stranded RNA (dsRNA). See, e.g., Majde, J. A., *J. Interfer. Cytokine Res.* (2000) 20:259-272. In fact, proinflammatory cytokines induced by viral dsRNA are now thought to be largely responsible for the flu-like symptoms caused by bacterial and viral infections, such as fever, fatigue, drowsiness and muscle aches. IFN-1 production, stimulated by delivery of dsRNA, has been reported to display adjuvant activity. See, e.g., Le Bon et al., *Immunity* (2001) 14:461-470.

Despite the presence of adjuvants, conventional vaccines often fail to provide adequate protection against the targeted pathogen. Accordingly, there is a continuing need for effective vaccine compositions which include safe and non-toxic adjuvants.

SUMMARY OF THE INVENTION

The present invention is based in part, on the surprising discovery that the use of type 1 interferon inducers, such as double-stranded RNA (dsRNA), in combination with one or more antigen delivery systems e.g., submicron oil-in-water emulsions, cationic lipids, liposomes, ISCOMs, microparticles, and the like and/or immunostimulatory molecules, such as immunostimulatory nucleic acid sequences (ISS), including CpY, CpR and unmethylated CpG motifs (a cytosine followed by guanosine and linked by a phosphate bond), provides for significantly higher antibody titers to a coadministered antigen, than those observed without such delivery systems. The use of such combinations provides a safe and effective approach for enhancing the immunogenicity of a variety of vaccine antigens for use in both prophylactic and therapeutic compositions.

Accordingly, in one embodiment, the invention is directed to a composition comprising: (1) a type 1 interferon inducer; and (2) an antigen delivery system and/or an immunostimulatory molecule, wherein the composition is capable of increasing the immune response to a coadministered antigen, as compared to delivery of antigen and type 1 interferon inducer alone without the antigen delivery system and/or the immunostimulatory molecule. The coadministered antigen may be present in the adjuvant composition or may be delivered in a separate composition. If delivered separately, the antigen may be delivered to the same or different site, and may be delivered prior to, subsequent to, or concurrent with the composition. These embodiments are discussed in greater detail below.

In yet another embodiment, the subject invention is directed to a method of stimulating an immune response in a vertebrate subject which comprises administering to the subject a therapeutically effective amount of a selected antigen and an adjuvant composition comprising a type 1 interferon inducer and an antigen delivery system and/or an immunostimulatory molecule, wherein the adjuvant composition is capable of increasing the immune response to the selected antigen. The antigen may be present in the adjuvant composition or may be administered in a separate composition. As explained above, if the antigen is delivered separately, it may be delivered to the same or different site, and may be delivered prior to, subsequent to, or concurrent with the adjuvant composition.

In still further embodiments, the invention is directed to a method of making a composition comprising combining a type 1 interferon inducer with an antigen delivery system and/or an immunostimulatory molecule. In certain embodiments, the method further comprises combining a selected antigen with the type 1 interferon inducer and antigen delivery system and/or an immunostimulatory molecule. In certain embodiments, the type 1 interferon inducer is dsRNA, the antigen delivery system is a submicron oil-in-water emulsion and/or a microparticle, the immunostimulatory molecule is an umnethylated CpG motif such as CpG1 (5'-TCCATGACGTTCCTGACGTT-3' (SEQ ID NO:3) and the antigen is an HCV antigen, such as an HCV E1E2 polypeptide, an HIV antigen, such as gp120 or p55gag, or a meningoccal antigen such as a MenB protein from ORFs 287 and/or 961

In additional embodiments, the invention is directed to a composition comprising an HCV, HIV or meningococcal antigen, a dsRNA and an antigen delivery system and/or an immunostimulatory molecule. In certain embodiments, the HCV antigen is an HCV E1E2 polypeptide, the HIV antigen is gp120 and/or p55gag and the meningococcal antigen is a MenB protein from ORFs 287 and/or 961. In certain embodiments, the antigen delivery system is a submicron oil-in-water emulsion and/or a microparticle, and the immunostimulatory molecule is an unmethylated CpG motif.

In yet another embodiment, the subject invention is directed to a method of stimulating an immune response in a vertebrate subject which comprises administering to the subject a therapeutically effective amount of an HCV, HIV or meningoccal antigen and an adjuvant composition comprising a dsRNA and a submicron oil-in-water emulsion. The antigen may be administered in the adjuvant composition or may be administered in a separate composition. If the antigen is delivered separately, it may be delivered to the same or different site, and may be delivered prior to, subsequent to, or concurrent with the adjuvant composition. In certain embodiments, the HCV antigen is an HCV E1E2 polypeptide, the HIV antigen is gp120 or p55gag and the meningoccal antigen is a MenB protein from ORFs 287 and/or 961.

In another embodiment, the subject invention is directed to a method of stimulating an immune response in a vertebrate subject which comprises administering to the subject a therapeutically effective amount of an HCV, HIV or meningococcal antigen and an adjuvant composition comprising a dsRNA and a microparticle. The antigen may be administered in the adjuvant composition or may be administered in a separate composition. If the antigen is delivered separately, it may be delivered to the same or different site, and may be delivered prior to, subsequent to, or concurrent with the adjuvant composition. In certain embodiments, the HCV antigen is an HCV E1E2 polypeptide, the HIV antigen is gp120 or p55gag and the meningoccal antigen is a MenB protein from ORFs 287 and/or 961.

In certain of the embodiments detailed above, the dsRNA is viral dsRNA or synthetic dsRNA, such as but are not limited to, polyriboinosinic-polyribocytidylic acid (poly[rI-rC]), polyriboguanylic-polyribocytidylic acid (poly[rG-rC]) or polyriboadenylic-polyribouridylic acid (poly[rA-rU]).

Additionally, the submicron oil-in-water emulsion may comprise:

(1) a metabolizable oil, wherein the oil is present in an amount of 0.5% to 20% of the total volume and (2) an emulsifying agent, wherein the emulsifying agent is 0.01% to 2.5% by weight (w/v), and wherein the oil and the emulsifying agent are present in the form of an oil-in-water emulsion having oil droplets substantially all of which are about 100 nm to less than 1 micron in diameter.

In other embodiments, the submicron oil-in-water emulsion is as described above and lacks any polyoxypropylene-polyoxyethylene block copolymer, as well as any muramyl peptide.

In additional embodiments, the emulsifying agent comprises a polyoxyethylene sorbitan mono-, di-, or triester and/or a sorbitan mono-, di-, or triester.

In certain embodiments, the oil is present in an amount of 1% to 12%, such as 1% to 4%, of the total volume and the emulsifying agent is 0.01% to 1% by weight (w/v), such as 0.01% to 0.05% by weight (w/v).

In other embodiments described herein, the submicron oil-in-water emulsion comprises 4-5% w/v squalene, 0.25-1.0% w/v TWEEN 80™ (polyoxyelthylenesorbitan monooleate), and/or 0.25-1.0% SPAN 85™ (sorbitan trioleate), and optionally, N-acetylmuramyl-L-alanyl-D-isogluatminyl-L-alanine-2-(1'-2'-dipalmitoyl-sn-glycero-3-huydroxyphosphoryloxy)-ethylamine (MTP-PE).

In other embodiments, the submicron oil-in-water emulsion consists essentially of:

(1) 5% by volume of squalene; and (2) one or more emulsifying agents selected from the group consisting of TWEEN 80™ (polyoxyelthylenesorbitan monooleate) and SPAN 85™ (sorbitan trioleate), wherein the total amount of emulsifying agent(s) present is 1% by weight (w/v); wherein the squalene and the emulsifying agent(s) are present in the form of an oil-in-water emulsion having oil droplets substantially all of which are about 100 nm to less than 1 micron in diameter and wherein the composition lacks any polyoxypropylene-polyoxyethylene block copolymer.

In other embodiments, the one or more emulsifying agents are polyoxyelthylenesorbitan monooleate and sorbitan trioleate and the total amount of polyoxyelthylenesorbitan monooleate and sorbitan trioleate present is 1% by weight (w/v).

In certain embodiments, the composition lacks a muramyl peptide.

In yet additional embodiments of the invention described above, the microparticle comprises a polymer selected from the group consisting of a poly($\alpha$-hydroxy acid), a polyhydroxy butyric acid, a polycaprolactone, a polyorthoester, and a polyanhydride. In particular embodiments, the microparticle comprises a poly(a-hydroxy acid) selected from the group consisting of poly(L-lactide), poly(D,L-lactide) and poly(D,L-lactide-co-glycolide) (PLG).

In additional embodiments, the type 1 interferon inducer and/or the antigen are associated with a microparticle. In certain embodiments, the type 1 interferon inducer is adsorbed to a PLG microparticle wherein the surface of the microparticle has been treated with a cationic detergent, such as CTAB, to impart enhanced adsorption properties to the microparticle. In other embodiments, the antigen is adsorbed to a microparticle, such as a PLG microparticle wherein the surface of the microparticle has been treated with an anionic detergent, such as DSS, to impart enhanced adsorption properties to the microparticle.

These and other aspects of the present invention will become evident upon reference to the following detailed description and attached drawings. In addition, various references are set forth herein which describe in more detail certain procedures or compositions, and are therefore incorporated by reference in their entireties.

BRIEF DESCRIPTION OF THE DRAWINGS

FIGS. 1A-1C (SEQ ID NOS:1 and 2) show the nucleotide and corresponding amino acid sequence for the HCV-1 E1/E2/p7 region. The numbers shown in the figure are relative to the full-length HCV-1 polyprotein. The E1, E2 and p7 regions are shown.

FIGS. 5A-5D (SEQ ID NO:5) show the nucleotide sequence of HIV Type C 8_5_TV1_C.ZA (also referred to as TV 1). Various regions are shown in Table 2.

DETAILED DESCRIPTION OF THE INVENTION

Figure 2:
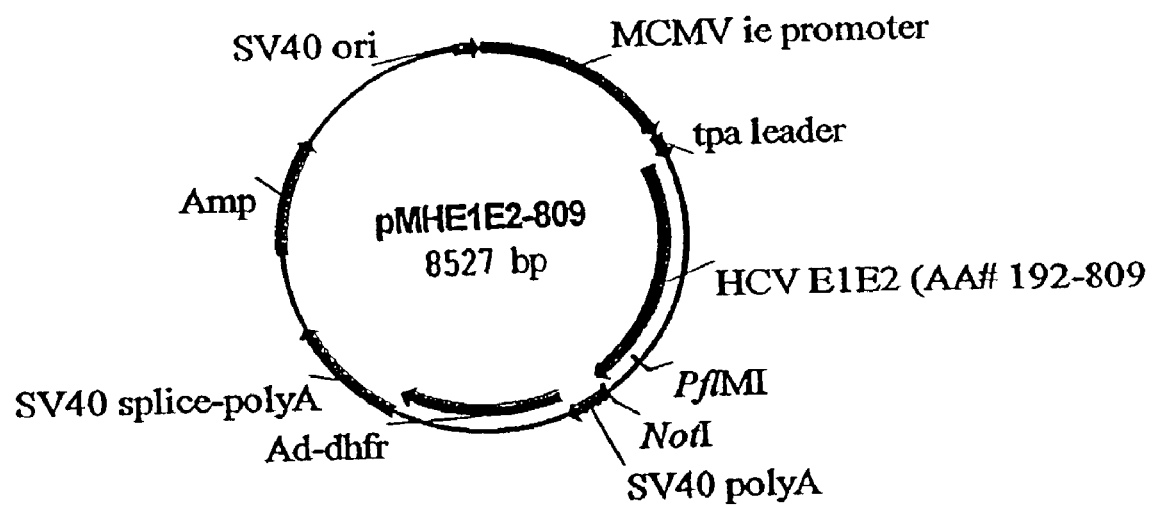
FIG. 2 is a diagram of plasmid pMHE1E2-809, encoding E1E2$_{809}$, a representative E1E2 protein for use with the present invention.

The practice of the present invention will employ, unless otherwise indicated, conventional methods of chemistry, biochemistry, recombinant DNA techniques and immunology, within the skill of the art. Such techniques are explained fully in the literature. See, e.g., *Fundamental Virology*, 2nd Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. Definitions

In describing the present invention, the following terms will be employed, and are intended to be defined as indicated below.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

By "antigen" is meant a molecule, which contains one or more epitopes (defined below) that will stimulate a host's immune system to make a cellular antigen-specific immune response when the antigen is presented, or a humoral antibody response. The term "antigen" as used herein denotes both subunit antigens, i.e., proteins which are separate and discrete from a whole organism with which the antigen is associated in nature, as well as killed, attenuated or inactivated bacteria, viruses, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses a therapeutic or immunogenic protein, or antigenic determinant in vivo, such as in gene therapy and nucleic acid immunization applications, is also included in the definition of antigen herein. Further, for purposes of the present invention, antigens can be derived from any of several known viruses, bacteria, parasites and fungi, as well as any of the various tumor antigens.

An "HCV antigen" is an antigen, as defined above, derived from the HCV polyprotein. The polypeptide need not be physically derived from HCV, but may be synthetically or recombinantly produced. Moreover, the polypeptide may be derived from any of the various HCV strains discussed further below. A number of conserved and variable regions are known between these strains and, in general, the amino acid sequences of epitopes derived from these regions will have a high degree of sequence homology, e.g., amino acid sequence homology of more than 30%, preferably more than 40%, when the two sequences are aligned. The complete genotypes of many of these strains are known. See, e.g., U.S. Pat. No. 6,150,087 and GenBank Accession Nos. AJ238800 and AJ238799.

By an "E1 polypeptide" is meant a molecule derived from an HCV E1 region. The mature E1 region of HCV-1 begins at approximately amino acid 192 of the polyprotein and continues to approximately amino acid 383, numbered relative to the full-length HCV-1 polyprotein. (See, FIGS. 1A-1C. Amino acids 192-383 of FIGS. 1A-1C correspond to amino acid positions 20-211 of SEQ ID NO:2.) Amino acids at around 173 through approximately 191 (amino acids 1-19 of SEQ ID NO: 2) serve as a signal sequence for E1. Thus, by an "E1 polypeptide" is meant either a precursor E1 protein, including the signal sequence, or a mature E1 polypeptide which lacks this sequence, or even an E1 polypeptide with a heterologous signal sequence. The E1 polypeptide includes a C-terminal membrane anchor sequence which occurs at approximately amino acid positions 360-383 (see, International Publication No. WO 96/04301, published Feb. 15, 1996). An E1 polypeptide, as defined herein, may or may not include the C-terminal anchor sequence or portions thereof.

By an "E2 polypeptide" is meant a molecule derived from an HCV E2 region. The mature E2 region of HCV-1 begins at approximately amino acid 383-385, numbered relative to the full-length HCV-1 polyprotein. (See, FIGS. 1A-1C. Amino acids 383-385 of FIGS. 1A-1C correspond to amino acid positions 211-213 of SEQ ID NO:2.) A signal peptide begins at approximately amino acid 364 of the polyprotein. Thus, by an "E2 polypeptide" is meant either a precursor E2 protein, including the signal sequence, or a mature E2 polypeptide which lacks this sequence, or even an E2 polypeptide with a heterologous signal sequence. The E2 polypeptide includes a C-terminal membrane anchor sequence which occurs at approximately amino acid positions 715-730 and may extend as far as approximately amino acid residue 746 (see, Lin et al., *J. Virol.* (1994) 68:5063-5073). An E2 polypeptide, as defined herein, may or may not include the C-terminal anchor sequence or portions thereof. Moreover, an E2 polypeptide may also include all or a portion of the p7 region which occurs immediately adjacent to the C-terminus of E2. As shown in FIGS. 1A-1C, the p7 region is found at positions 747-809, numbered relative to the full-length HCV-1 polyprotein (amino acid positions 575-637 of SEQ ID NO:2). Additionally, it is known that multiple species of HCV E2 exist (Spaete et al., *Virol.* (1992) 188:819-830; Selby et al., *J. Virol.* (1996) 70:5177-5182; Grakoui et al., *J. Virol.* (1993) 67:1385-1395; Tomei et al., *J. Virol.* (1993) 67:4017-4026). Accordingly, for purposes of the present invention, the term "E2" encompasses any of these species of E2 including, without limitation, species that have deletions of 1-20 or more of the amino acids from the N-terminus of the E2, such as, e.g, deletions of 1, 2, 3, 4, 5 . . . 10 . . . 15, 16, 17, 18, 19 . . . etc. amino acids. Such E2 species include those beginning at amino acid 387, amino acid 402, amino acid 403, etc.

Representative E1 and E2 regions from HCV-1 are shown in FIGS. 1A-1C and SEQ ID NO:2. For purposes of the present invention, the E1 and E2 regions are defined with respect to the amino acid number of the polyprotein encoded by the genome of HCV-1, with the initiator methionine being designated position 1. See, e.g., Choo et al., *Proc. Natl. Acad. Sci. USA* (1991) 88:2451-2455. However, it should be noted that the term an "E1 polypeptide" or an "E2 polypeptide" as used herein is not limited to the HCV-1 sequence. In this regard, the corresponding E1 or E2 regions in other HCV isolates can be readily determined by aligning sequences from the isolates in a manner that brings the sequences into maximum alignment. This can be performed with any of a number of computer software packages, such as ALIGN 1.0, available from the University of Virginia, Department of Biochemistry (Attn: Dr. William R. Pearson). See, Pearson et al., *Proc. Natl. Acad. Sci. USA* (1988) 85:2444-2448.

Furthermore, an "E1 polypeptide" or an "E2 polypeptide" as defined herein is not limited to a polypeptide having the exact sequence depicted in the Figures. Indeed, the HCV genome is in a state of constant flux in vivo and contains several variable domains which exhibit relatively high degrees of variability between isolates. A number of conserved and variable regions are known between these strains and, in general, the amino acid sequences of epitopes derived from these regions will have a high degree of sequence homology, e.g., amino acid sequence homology of more than 30%, preferably more than 40%, more than 60%, and even more than 80-90% homology, when the two sequences are aligned. It is readily apparent that the terms encompass E1 and E2 polypeptides from any of the various HCV strains and isolates including isolates having any of the 6 genotypes of HCV described in Simmonds et al., *J. Gen. Virol.* (1993) 74:2391-2399 (e.g., strains 1, 2, 3, 4 etc.), as well as newly identified isolates, and subtypes of these isolates, such as HCV1a, HCV1b etc.

Thus, for example, the term "E1" or "E2" polypeptide refers to native E1 or E2 sequences from any of the various HCV strains, as well as analogs, muteins and immunogenic fragments, as defined further below. The complete genotypes of many of these strains are known. See, e.g., U.S. Pat. No. 6,150,087 and GenBank Accession Nos. AJ238800 and AJ238799.

Additionally, the terms "E1 polypeptide" and "E2 polypeptide" encompass proteins which include modifications to the native sequence, such as internal deletions, additions and substitutions (generally conservative in nature). These modifications may be deliberate, as through site-directed mutagenesis, or may be accidental, such as through naturally occurring mutational events. All of these modifications are encompassed in the present invention so long as the modified E1 and E2 polypeptides function for their intended purpose. Thus, for example, if the E1 and/or E2 polypeptides are to be used in vaccine compositions, the modifications must be such that immunological activity (i.e., the ability to elicit a humoral or cellular immune response to the polypeptide) is not lost.

By "E1E2" complex is meant a protein containing at least one E1 polypeptide and at least one E2 polypeptide, as described above. Such a complex may also include all or a portion of the p7 region which occurs immediately adjacent to the C-terminus of E2. As shown in FIGS. 1A-1C, the p7 region is found at positions 747-809, numbered relative to the full-length HCV-1 polyprotein (amino acid positions 575-637 of SEQ ID NO:2). A representative E1E2 complex which includes the p7 protein is termed "E1E2$_{809}$" herein.

The mode of association of E1 and E2 in an E1E2 complex is immaterial. The E1 and E2 polypeptides may be associated through non-covalent interactions such as through electrostatic forces, or by covalent bonds. For example, the E1E2 polypeptides of the present application may be in the form of a fusion protein which includes an immunogenic E1 polypeptide and an immunogenic E2 polypeptide, as defined above. The fusion may be expressed from a polynucleotide encoding an E1E2 chimera. Alternatively, E1E2 complexes may form spontaneously simply by mixing E1 and E2 proteins which have been produced individually. Similarly, when co-expressed and secreted into media, the E1 and E2 proteins can form a complex spontaneously. Thus, the term encompasses E1E2 complexes (also called aggregates) that spontaneously form upon purification of E1 and/or E2. Such aggregates may include one or more E1 monomers in association with one or more E2 monomers. The number of E1 and E2 monomers present need not be equal so long as at least one E1 monomer and one E2 monomer are present. Detection of the presence of an E1E2 complex is readily determined using standard protein detection techniques such as polyacrylamide gel electrophoresis and immunological techniques such as immunoprecipitation.

An "HIV antigen" is an antigen, as defined above, derived from the HIV polyprotein. The polypeptide need not be physically derived from HIV, but may be synthetically or recombinantly produced. Moreover, the polypeptide may be derived from any of the various HIV isolates. A number of conserved and variable regions are known between these strains and, in general, the amino acid sequences of epitopes derived from these regions will have a high degree of sequence homology, e.g., amino acid sequence homology of more than 30%, preferably more than 40%, when the two sequences are aligned. Representative HIV isolates include SF162, SF2, AF110965, AF110967, AF110968, AF110975, 8_5_TV1_C.ZA, 8_2TV1_C.ZA or 12-5_1_TV2_C.ZA. The various regions of the HIV genome are shown in Table 2, with numbering relative to 8_5_TV1_C.ZA (FIGS. 5A-5D; SEQ ID NO:5).

By a "gp120 antigen" is meant an antigen, as defined above, derived from a gp120 region of the Env polypeptide of HIV. The primary amino acid sequence of gp120 is approximately 511 amino acids, with a polypeptide core of about 60,000 daltons. The polypeptide is extensively modified by N-linked glycosylation to increase the apparent molecular weight of the molecule to 120,000 daltons. The amino acid sequence of gp120 contains five relatively conserved domains interspersed with five hypervariable domains. The positions of the 18 cysteine residues in the gp120 primary sequence of the HIV-1$_{HXB-2}$ strain, and the positions of 13 of the approximately 24 N-linked glycosylation sites in the gp120 sequence are common to most, if not all, gp120 sequences. The hypervariable domains contain extensive amino acid substitutions, insertions and deletions. Despite this variation, most, if not all, gp120 sequences preserve the virus's ability to bind to the viral receptor CD4. A "gp120 antigen" includes both single subunits or multimers. Moreover, the term encompasses gp120 sequences that have been modified for optimum codon usage to simulate human codons and to reduce toxicity. Such modified sequences are known in the art and the sequences and methods of producing the same are described in detail in commonly owned International Publication No. WO 00/39302, incorporated by reference herein in its entirety.

By a "p55gag antigen" is meant an antigen, as defined above, representing the GAG region of HIV which encoded by a region spanning approximately 1494 nucleotides (see, Table 2). The term encompasses sequences that have been modified for optimum codon usage to simulate human codons and to reduce toxicity. Such modified sequences are known in the art and the sequences and methods of producing the same are described in detail in commonly owned International Publication No. WO 00/39302, incorporated by reference herein in its entirety.

The terms "analog" and "mutein" refer to biologically active derivatives of the reference molecule, or fragments of such derivatives, that retain desired activity, such as immunoreactivity as described herein. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to peptides having one or more peptide mimics ("peptoids"), such as those described in International Publication No. WO 91/04282, incorporated by reference herein in its entirety. Preferably, the analog or mutein has at least the same immunoactivity as the native molecule. Methods for making polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 or 50 conservative or non-conservative amino acid substitutions, or any integer between 5-50, so long as the desired function of the molecule remains intact. One of skill in the art may readily determine regions of the molecule of interest that can tolerate change by reference to Hopp/Woods and Kyte-Doolittle plots, well known in the art.

By "fragment" is intended a polypeptide consisting of only a part of the intact full-length polypeptide sequence and structure. The fragment can include a C-terminal deletion an N-terminal deletion, and/or an internal deletion of the native polypeptide. An "immunogenic fragment" of a particular protein will generally include at least about 5-10 contiguous amino acid residues of the full-length molecule, preferably at least about 15-25 contiguous amino acid residues of the fill-length molecule, and most preferably at least about 20-50 or more contiguous amino acid residues of the full-length molecule, that define an epitope, or any integer between 5 amino acids and the full-length sequence, provided that the fragment in question retains the ability to elicit an immunological response as defined herein. For a description of known immunogenic fragments of HCV polypeptides, see, e.g., Chien et al., *Proc. Natl. Acad. Sci. USA* (1992) 89:10011-10015; Chien et al., *J. Gastroent. Hepatol*. (1993) 8:S33-39; Chien et al., International Publication No. WO 93/00365; Chien, D.Y., International Publication No. WO 94/01778; U.S. Pat. Nos. 6,150,087 and 6,121,020, all of which are incorporated by reference herein in their entireties.

The term "epitope" as used herein refers to a sequence of at least about 3 to 5, preferably about 5 to 10 or 15, and not more than about 500 amino acids (or any integer therebetween), which define a sequence that by itself or as part of a larger sequence, elicits an immunological response in the subject to which it is administered. Often, an epitope will bind to an antibody generated in response to such sequence. There is no critical upper limit to the length of the fragment, which may comprise nearly the full-length of the protein sequence, or even a fusion protein comprising two or more epitopes from the antigen of interest. An epitope for use in the subject invention is not limited to a polypeptide having the exact sequence of the portion of the parent protein from which it is derived. For example, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, New Jersey. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1985) *Proc. Natl. Acad. Sci. USA* 82:178-182; Geysen et al. (1986) *Molec. Immunol.* 23:709-715, all incorporated herein by reference in their entireties. Using such techniques, a number of epitopes of HCV have been identified. See, e.g., Chien et al., *Viral Hepatitis and Liver Disease* (1994) pp. 320-324, and further below. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824-3828 for determining antigenicity profiles, and the Kyte-Doolittle technique, Kyte et al., *J. Mol. Biol.* (1982) 157:105-132 for hydropathy plots.

An "immunological response" to a selected antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376.

Thus, an immunological response as used herein may be one which stimulates the production of CTLs, and/or the production or activation of helper T-cells. The antigen of interest may also elicit an antibody-mediated immune response, including, or example, neutralization of binding (NOB) antibodies. The presence of an NOB antibody response is readily determined by the techniques described in, e.g., Rosa et al., *Proc. Natl. Acad. Sci. USA* (1996) 93:1759. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection or alleviation of symptoms to an immunized host. Such responses can be determined using standard immunoassays and neutralization assays, well known in the art.

By "type 1 interferon inducer" is meant a molecule that elicits type 1 interferon (IFN-1) production above base levels. IFN-α and IFN-β are the major species of type 1 interferons. Thus, IFN-1 levels can be assessed using assays that measure IFN-α and IFN-β. Such assays are well known in the art. One representative assay measures the ability of the sample to inhibit the cytopathic effect of vesicular stomatitis virus on L cells in monolayer culture. See, e.g., Le Bon et al., *Immunity* (2001) 14:461-470. Another assay measures antiviral activity in culture using encephalomyocarditis virus (EMCV) as a test virus. See, e.g., Tazulakhova et al., *J. Interfer. Cyotkine Res.* (2001) 21:65-73.

The term "antigen delivery system" encompasses adjuvants that are particulate in nature, such as cationic emulsions, submicron oil-in-water emulsions, microparticles, ISCOMs, liposomes, and the like. Such delivery systems generally function to target associated antigens (e.g., either entrapped, adsorbed or otherwise associated) to antigen presenting cells (APC). Such antigen delivery systems are described in detail below.

The term "immunostimulatory molecule" intends an adjuvant that is derived from a pathogen and represents pathogen associated molecular patterns (PAMP) such as LPS and MPL. The term also encompasses immunostimulatory nucleotide sequences, as defined below, which molecules activate cells of the innate immune system. Once activated, cells of innate immunity drive and focus the acquired immune response.

As used herein an "immunostimulatory nucleotide sequence" or "ISS" means a polynucleotide that includes at least one immunostimulatory oligonucleotide (ISS-ODN) moiety. The ISS moiety is a single- or double-stranded DNA or RNA oligonucleotide having at least six nucleotide bases that may include, or consist of, a modified oligonucleotide or a sequence of modified nucleosides. The ISS moieties comprise, or may be flanked by, a CG-containing nucleotide sequence or a p(1C) nucleotide sequence, which may be palindromic. The cysteine may be methylated or unmethylated. Examples of particular ISS molecules for use in the present invention include CpG molecules, discussed further below, as well as CpY and CpR molecules and the like.

A "recombinant" protein is a protein which retains the desired activity and which has been prepared by recombinant DNA techniques as described herein. In general, the gene of interest is cloned and then expressed in transformed organisms, as described further below. The host organism expresses the foreign gene to produce the protein under expression conditions.

By "isolated" is meant, when referring to a polypeptide, that the molecule is separate and discrete from the whole organism with which the molecule is found in nature or is present in the substantial absence of other biological macromolecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

By "equivalent antigenic determinant" is meant an antigenic determinant from different sub-species or strains of a particular pathogen, such as HCV, for example from strains 1, 2, 3, etc., of HCV which antigenic determinants are not necessarily identical due to sequence variation, but which occur in equivalent positions in the genomic sequence in question. In general the amino acid sequences of equivalent antigenic determinants will have a high degree of sequence homology, e.g., amino acid sequence homology of more than 30%, usually more than 40%, such as more than 60%, and even more than 80-90% homology, when the two sequences are aligned.

"Homology" refers to the percent similarity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence similarity or identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, DC, which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

An adjuvant composition comprising a type 1 interferon inducer, such as dsRNA, and an antigen delivery system and/or an immunostimulatory molecule or ISS, "enhances" or "increases" the immune response, or displays "enhanced" or "increased" immunogenicity vis-a-vis a selected antigen when it possesses a greater capacity to elicit an immune response than the immune response elicited by an equivalent amount of the antigen when delivered with the type 1 interferon inducer, without an antigen delivery system and/or an immunostimulatory molecule. Such enhanced immunogenicity can be determined by administering the antigen and adjuvant composition, and antigen controls to animals and comparing antibody titers against the two using standard assays such as radioimmunoassay and ELISAs, well known in the art.

The terms "effective amount" or "pharmaceutically effective amount" of an adjuvant composition and antigen, as provided herein, refer to a nontoxic but sufficient amount of the composition to provide the desired response, such as an immunological response, and optionally, a corresponding therapeutic effect, or in the case of delivery of a therapeutic protein, an amount sufficient to effect treatment of the subject, as defined below. As will be pointed out below, the exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

By "vertebrate subject" is meant any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The invention described herein is intended for use in any of the above vertebrate species, since the immune systems of all of these vertebrates operate similarly.

II. Modes of Carrying out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

As noted above, the present invention is based on the discovery that an antigen, delivered in combination with an adjuvant composition comprising a type 1 interferon inducer, such as dsRNA, and an antigen delivery system and/or an immunostimulatory molecule, elicits significantly higher antibody titers than those observed without such adjuvants. In order to further an understanding of the invention, a more detailed discussion is provided below regarding antigens for use in the subject methods and compositions, as well as production of adjuvant compositions comprising type 1 interferon inducers.

Antigens

In particular, the compositions and methods of the invention provide for enhanced immune responses, including cell-mediated immunity, and/or humoral antibody responses. Accordingly, the compositions and methods of the present invention will find use with any antigen for which cellular and/or humoral immune responses are desired, including antigens derived from viral, bacterial, fungal and parasitic pathogens that may induce antibodies, T-cell helper epitopes and T-cell cytotoxic epitopes. Such antigens include, but are not limited to, those encoded by human and animal viruses and can correspond to either structural or non-structural proteins.

The technique is particularly useful for immunization against intracellular viruses and tumor cell antigens which normally elicit poor immune responses. Additionally, the compositions and methods can be used to produce antibodies in laboratory animals for immunopurification, diagnostic, and other purposes.

For example, the present invention will find use for stimulating an immune response against a wide variety of proteins from the herpesvirus family, including proteins derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human herpesviruses such as HHV6 and HHV7. (See, e.g. Chee et al., *Cytomegaloviruses* (J. K. McDougall, ed., Springer-Verlag 1990) pp. 125-169, for a review of the protein coding content of cytomegalovirus; McGeoch et al., *J. Gen. Virol.* (1988) 69:1531-1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207-211, for the identification of protein coding sequences in an EBV genome; and Davison and Scott, *J. Gen. Virol.* (1986) 67:1759-1816, for a review of VZV.)

Antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436, incorporated by reference herein in their entireties. The HCV genome encodes several viral proteins, discussed further below. These proteins, as well as antigenic fragments thereof, will find use in the present methods. Similarly, the sequence for the δ-antigen from HDV is known (see, e.g., U.S. Pat. No. 5,378,814) and this sequence can also be conveniently used in the present methods. Additionally, antigens derived from HBV, such as the core antigen, the surface antigen, sAg, as well as the presurface sequences, pre-S1 and pre-S2 (formerly called pre-S), as well as combinations of the above, such as sAg/pre-S1, sAg/pre-S2, sAg/pre-S1/pre-S2, and pre-S1/pre-S2, will find use herein. See, e.g., "HBV Vaccines—from the laboratory to license: a case study" in Mackett, M. and Williamson, J. D., *Human Vaccines and Vaccination*, pp. 159-176, for a discussion of HBV structure; and U.S. Pat. Nos. 4,722,840, 5,098,704, 5,324,513, incorporated herein by reference in their entireties; Beames et al., *J. Virol.* (1995) 69:6833-6838, Birnbaum et al., *J. Virol.* (1990) 64:3319-3330; and Zhou et al., *J. Virol.* (1991) 65:5457-5464.

Antigens derived from other viruses will also find use in the claimed methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); $HIV-1_{CM235}$, $HIV-1_{US4}$; HIV-2; simian immunodeficiency virus (SIV) among others. Additionally, antigens may also be derived from human papillomavirus (HPV) and the tick-borne encephalitis viruses. See, e.g. Virology, 3rd Edition (W. K. Joklik ed. 1988); *Fundamental Virology*, 2nd Edition (B. N. Fields and D. M. Knipe, eds. 1991), for a description of these and other viruses.

More particularly, the gp120 envelope protein from any of the above HIV isolates, including members of the various genetic subtypes of HIV, are known and reported (see, e.g., Myers et al., Los Alamos Database, Los Alamos National Laboratory, Los Alamos, N. Mex. (1992); Myers et al., *Human Retroviruses and Aids*, 1990, Los Alamos, N. Mex.: Los Alamos National Laboratory; and Modrow et al., *J. Virol.* (1987) 61:570-578, for a comparison of the envelope gene sequences of a variety of HIV isolates) and sequences derived from any of these isolates will find use in the present methods. Furthermore, the invention is equally applicable to other immunogenic proteins derived from any of the various HIV isolates, including any of the various envelope proteins such as gp160, gp140 and gp41, gag antigens such as p24gag and p55gag, as well as proteins derived from the pol region.

Influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al., *Virology* (1990) 179:759-767; Webster et al., "Antigenic variation among type A influenza viruses," p. 127-168. In: P. Palese and D. W. Kingsbury (ed.), *Genetics of influenza viruses*. Springer-Verlag, New York). Thus, proteins derived from any of these isolates can also be used in the invention described herein.

Antigens for use in the compositions and methods described herein may also be derived from numerous bacterial antigens, such as those from organisms that cause diphtheria, cholera, tuberculosis, tetanus, pertussis, meningitis, and other pathogenic states, including, without limitation, Meningococcus A, B and C, *Hemophilus influenza* type B (HIB), and *Helicobacter pylori*. Examples of parasitic antigens include those derived from organisms causing malaria and Lyme disease.

Furthermore, the methods described herein provide a means for treating a variety of malignant cancers. For example, the system of the present invention can be used to mount both humoral and cell-mediated immune responses to particular proteins specific to the cancer in question, such as an activated oncogene, a fetal antigen, or an activation marker. Such tumor antigens include any of the various MAGEs (melanoma associated antigen E), including MAGE 1, 2, 3, 4, etc. (Boon, T. *Scientific American* (March 1993): 82-89); any of the various tyrosinases; MART 1 (melanoma antigen recognized by T cells), mutant ras; mutant p53; p97 melanoma antigen; CEA (carcinoembryonic antigen), among others.

It is readily apparent that the subject invention can be used to raise antibodies to a large number of antigens for diagnostic and immunopurification purposes, as well as to prevent or treat a wide variety of diseases.

As explained above, the compositions and methods of the present invention may employ HCV antigens. The genome of the hepatitis C virus typically contains a single open reading frame of approximately 9,600 nucleotides, which is transcribed into a polyprotein. The full-length sequence of the polyprotein is disclosed in European Publication No. 388,232 and U.S. Pat. No. 6,150,087, incorporated herein by reference in their entireties. As shown in Table 1, An HCV polyprotein, upon cleavage, produces at least ten distinct products, in the order of NH$_2$-Core-E1-E2-p7-NS2-NS3-NS4a-NS4b-NS5a-NS5b-COOH. The core polypeptide occurs at positions 1-191, numbered relative to HCV-1 (see, Choo et al. (1991) *Proc. Natl. Acad. Sci. USA* 88:2451-2455, for the HCV-1 genome). This polypeptide is further processed to produce an HCV polypeptide with approximately amino acids 1-173. The envelope polypeptides, E1 and E2, occur at about positions 192-383 and 384-746, respectively. The P7 domain is found at about positions 747-809. NS2 is an integral membrane protein with proteolytic activity and is found at about positions 810-1026 of the polyprotein. NS2, either alone or in combination with NS3 (found at about positions 1027-1657), cleaves the NS2-NS3 sissle bond which in turn generates the NS3 N-terminus and releases a large polyprotein that includes both serine protease and RNA helicase activities. The NS3 protease, found at about positions 1027-1207, serves to process the remaining polyprotein. The helicase activity is found at about positions 1193-1657. Completion of polyprotein maturation is initiated by autocatalytic cleavage at the NS3-NS4a junction, catalyzed by the NS3 serine protease. Subsequent NS3-mediated cleavages of the HCV polyprotein appear to involve recognition of polyprotein cleavage junctions by an NS3 molecule of another polypeptide. In these reactions, NS3 liberates an NS3 cofactor (NS4a, found about positions 1658-1711), two proteins (NS4b found at about positions 1712-1972, and NS5a found at about positions 1973-2420), and an RNA-dependent RNA polymerase (NS5b found at about positions 2421-3011).

TABLE 1

| Domain | Approximate Boundaries* |
|---|---|
| C (core) | 1-191 |
| E1 | 192-383 |
| E2 | 384-746 |
| P7 | 747-809 |
| NS2 | 810-1026 |
| NS3 | 1027-1657 |
| NS4a | 1658-1711 |
| NS4b | 1712-1972 |
| NS5a | 1973-2420 |
| NS5b | 2421-3011 |

*Numbered relative to HCV-1. See, Choo et al. (1991) Proc. Natl. Acad. Sci. USA 88:2451-2455.

Sequences for the above HCV polyprotein products, and immunogenic polypeptides derived therefrom, are known (see, e.g., U.S. Pat. No. 5,350,671, incorporated herein by reference in its entirety). For example, a number of general and specific immunogenic polypeptides, derived from the HCV polyprotein, have been described. See, e.g., Houghton et al., European Publ. Nos. 318,216 and 388,232; Choo et al. *Science* (1989) 244:359-362; Kuo et al. *Science* (1989) 244: 362-364; Houghton et al. *Hepatology* (1991) 14:381-388; Chien et al. *Proc. Natl. Acad. Sci. USA* (1992) 89:10011-10015; Chien et al. *J. Gastroent. Hepatol.* (1993) 8:S33-39; Chien et al., International Publ. No. WO 93/00365; Chien, D. Y., International Publ. No. WO 94/01778. These publications provide an extensive background on HCV generally, as well as on the manufacture and uses of HCV polypeptide immunological reagents. For brevity, therefore, the disclosure of these publications is incorporated herein by reference.

Any desired antigenic HCV polypeptide can be utilized with the present invention, including, for example, the E1 and/or E2 envelope glycoproteins of HCV, as well as E1E2 complexes, associated either through non-covalent or covalent interactions Such complexes may be made up of immunogenic fragments of E1 and E2 which comprise epitopes. For example, fragments of E1 polypeptides can comprise from about 5 to nearly the full-length of the molecule, such as 6, 10, 25, 50, 75, 100, 125, 150, 175, 185 or more amino acids of an E1 polypeptide, or any integer between the stated numbers. Similarly, fragments of E2 polypeptides can comprise 6, 10, 25, 50, 75, 100, 150, 200, 250, 300, or 350 amino acids of an E2 polypeptide, or any integer between the stated numbers. The E1 and E2 polypeptides may be from the same or different HCV strains. For example, epitopes derived from, e.g., the hypervariable region of E2, such as a region spanning amino acids 384-410 or 390-410, can be included in the E2 polypeptide. A particularly effective E2 epitope to incorporate into the E2 sequence or E1E2 complexes is one which includes a consensus sequence derived from this region, such as the consensus sequence Gly-Ser-Ala-Ala-Arg-Thr-Thr-Ser-Gly-Phe-Val-Ser-Leu-Phe-Ala-Pro-Gly-Ala-Lys-Gln-Asn (SEQ ID NO:4), which represents a consensus sequence for amino acids 390-410 of the HCV type 1 genome. Additional epitopes of E1 and E2 are known and described in, e.g., Chien et al., International Publication No. WO 93/00365, incorporated by reference herein in its entirety.

Moreover, the E1 and E2 polypeptides may lack all or a portion of the membrane spanning domain. The membrane anchor sequence functions to associate the polypeptide to the endoplasmic reticulum. Normally, such polypeptides are capable of secretion into growth medium in which an organism expressing the protein is cultured. However, as described in International Publication No. WO 98/50556, such polypeptides may also be recovered intracellularly. Secretion into growth medium is readily determined using a number of detection techniques, including, e.g., polyacrylamide gel electrophoresis and the like, and immunological techniques such as immunoprecipitation assays as described in, e.g., International Publication No. WO 96/04301, published Feb. 15, 1996. With E1, generally polypeptides terminating with about amino acid position 370 and higher (based on the numbering of HCV1 E1) will be retained by the ER and hence not secreted into growth media. With E2, polypeptides terminating with about amino acid position 731 and higher (also based on the numbering of the HCV1 E2 sequence) will be retained by the ER and not secreted. (See, e.g., International Publication No. WO 96/04301, published Feb. 15, 1996). It should be noted that these amino acid positions are not absolute and may vary to some degree. Thus, the present invention contemplates the use of E1 and E2 polypeptides which retain the transmembrane binding domain, as well as polypeptides which lack all or a portion of the transmembrane binding domain, including E1 polypeptides terminating at about amino acids 369 and lower, and E2 polypeptides, terminating at about amino acids 730 and lower, are intended to be captured by the present invention. Furthermore, the C-terminal truncation can extend beyond the transmembrane spanning domain towards the N-terminus. Thus, for example, E1 truncations occurring at positions lower than, e.g., 360 and E2 truncations occurring at positions lower than, e.g., 715, are also encompassed by the present invention. All that is necessary is that the truncated E1 and E2 polypeptides remain functional for their intended purpose. However, particularly preferred truncated E1 constructs are those that do not extend beyond about amino acid 300. Most preferred are those terminating at position 360. Preferred truncated E2 constructs are those with C-terminal truncations that do not extend beyond about amino acid position 715. Particularly preferred E2 truncations are those molecules truncated after any of amino acids 715-730, such as 725. If truncated molecules are used, it is preferable to use E1 and E2 molecules that are both truncated.

E2 exists as multiple species (Spaete et al., *Virol.* (1992) 188:819-830; Selby et al., *J. Virol.* (1996) 70:5177-5182; Grakoui et al., *J. Virol.* (1993) 67:1385-1395; Tomei et al., *J. Virol.* (1993) 67:4017-4026) and clipping and proteolysis may occur at the N- and C-termini of the E1 and E2 polypeptides. Thus, an E2 polypeptide for use herein may comprise at least amino acids 405-661, e.g., 400, 401, 402 ... to 661, such as 384-661, 384-715, 384-746, 384-749 or 384-809, or 384 to any C-terminus between 661-809, of an HCV polyprotein, numbered relative to the full-length HCV-1 polyprotein. Similarly, preferable E1 polypeptides for use herein can comprise amino acids 192-326, 192-330, 192-333, 192-360, 192-363, 192-383, or 192 to any C-terminus between 326-383, of an HCV polyprotein.

The E1 and E2 polypeptides and complexes thereof may also be present as asialoglycoproteins. Such asialoglycoproteins are produced by methods known in the art, such as by using cells in which terminal glycosylation is blocked. When these proteins are expressed in such cells and isolated by GNA lectin affinity chromatography, the E1 and E2 proteins aggregate spontaneously. Detailed methods for producing these E1E2 aggregates are described in, e.g., U.S. Pat. No. 6,074,852, incorporated herein by reference in its entirety. For example, E1E2 complexes are readily produced recombinantly, either as fusion proteins or by e.g., co-transfecting host cells with constructs encoding for the E1 and E2 polypeptides of interest. Co-transfection can be accomplished either in trans or cis, i.e., by using separate vectors or by using a single vector which bears both of the E1 and E2 genes. If done using a single vector, both genes can be driven by a single set of control elements or, alternatively, the genes can be present on the vector in individual expression cassettes, driven by individual control elements. Following expression, the E1 and E2 proteins will spontaneously associate. Alternatively, the complexes can be formed by mixing the individual proteins together which have been produced separately, either in purified or semi-purified form, or even by mixing culture media in which host cells expressing the proteins, have been cultured, if the proteins are secreted. Finally, the E1E2 complexes of the present invention may be expressed as a fusion protein wherein the desired portion of E1 is fused to the desired portion of E2.

Moreover, the E1E2 complexes may be present as a heterogeneous mixture of molecules, due to clipping and proteolytic cleavage, as described above. Thus, a composition including E1E2 complexes may include multiple species of E1E2, such as E1E2 terminating at amino acid 746 (E1E2$_{746}$), E1E2 terminating at amino acid 809 (E1E2$_{809}$), or any of the other various E1 and E2 molecules described above, such as E2 molecules with N-terminal truncations of from 1-20 amino acids, such as E2 species beginning at amino acid 387, amino acid 402, amino acid 403, etc.

E1E2 complexes are readily produced recombinantly, either as fusion proteins or by e.g., co-transfecting host cells with constructs encoding for the E1 and E2 polypeptides of interest. Co-transfection can be accomplished either in trans or cis, i.e., by using separate vectors or by using a single vector which bears both of the E1 and E2 genes. If done using a single vector, both genes can be driven by a single set of control elements or, alternatively, the genes can be present on the vector in individual expression cassettes, driven by individual control elements. Following expression, the E1 and E2 proteins will spontaneously associate. Alternatively, the complexes can be formed by mixing the individual proteins together which have been produced separately, either in purified or semi-purified form, or even by mixing culture media in which host cells expressing the proteins, have been cultured, if the proteins are secreted. Finally, the E1E2 complexes of the present invention may be expressed as a fusion protein wherein the desired portion of E1 is fused to the desired portion of E2.

Methods for producing E1E2 complexes from full-length, truncated E1 and E2 proteins which are secreted into media, as well as intracellularly produced truncated proteins, are known in the art. For example, such complexes may be produced recombinantly, as described in U.S. Pat. No. 6,121,020; Ralston et al., *J. Virol.* (1993) 67:6753-6761, Grakoui et al., *J. Virol.* (1993) 67:1385-1395; and Lanford et al., *Virology* (1993) 197:225-235.

Other HCV polypeptides may also be used in the invention. For example, HCV polypeptides derived from the Core region, such as polypeptides derived from the region found between amino acids 1-191; amino acids 10-53; amino acids 10-45; amino acids 67-88; amino acids 86-100; 81-130; amino acids 121-135; amino acids 120-130; amino acids 121-170; and any of the Core epitopes identified in, e.g., Houghton et al., U.S. Pat. No. 5,350,671; Chien et al. *Proc. Natl. Acad. Sci. USA* (1992) 89:10011-10015; Chien et al. *J. Gastroent. Hepatol.* (1993) 8:S33-39; Chien et al., International Publ. No. WO 93/00365; Chien, D. Y., International Publ. No. WO 94/01778; and U.S. Pat. No. 6,150,087, the disclosures of which are incorporated herein by reference in their entireties, will find use with the subject compositions and methods.

Additionally, polypeptides derived from the nonstructural regions of the virus will also find use herein. The NS3/4a region of the HCV polyprotein has been described and the amino acid sequence and overall structure of the protein are disclosed in Yao et al. *Structure* (November 1999) 7:1353-1363. See, also, Dasmahapatra et al., U.S. Pat. No. 5,843,752, incorporated herein by reference in its entirety. As explained above, either the native sequence or immunogenic analogs can be used in the subject formulations. Dasmahapatra et al., U.S. Pat. No. 5,843,752 and Zhang et al., U.S. Pat. No. 5,990,276, both describe analogs of NS3/4a and methods of making the same.

Moreover, polypeptides for use in the subject compositions and methods may be derived from the NS3 region of the HCV polyprotein. A number of such polypeptides are known, including, but not limited to polypeptides derived from the c33c and c100 regions, as well as fusion proteins comprising an NS3 epitope, such as c25. These and other NS3 polypeptides are useful in the present compositions and are known in the art and described in, e.g., Houghton et al, U.S. Pat. No. 5,350,671; Chien et al. *Proc. Natl. Acad. Sci. USA* (1992) 89:10011-10015; Chien et al. *J. Gastroent. Hepatol.* (1993) 8:S33-39; Chien et al., International Publ. No. WO 93/00365; Chien, D. Y., International Publ. No. WO 94/01778; and U.S. Pat. No. 6,150,087, the disclosures of which are incorporated herein by reference in their entireties.

Additionally, multiple epitope fusion antigens (termed "MEFAs"), as described in International Publ. No. WO 97/44469, may be used in the subject compositions. Such MEFAs include multiple epitopes derived from two or more of the various viral regions. The epitopes are preferably from more than one HCV strain, thus providing the added ability to protect against multiple strains of HCV in a single vaccine.

It should be noted that for convenience, the various HCV regions are generally defined with respect to the amino acid number relative to the polyprotein encoded by the genome of HCV-1a, as described in Choo et al. (1991) *Proc Natl Acad Sci USA* 88:2451, with the initiator methionine being designated position 1. However, the polypeptides for use with the present invention are not limited to those derived from the HCV-1a sequence. Any strain or isolate of HCV can serve as the basis for providing antigenic sequences for use with the invention. In this regard, the corresponding regions in another HCV isolate can be readily determined by aligning sequences from the two isolates in a manner that brings the sequences into maximum alignment.

Various strains and isolates of HCV are known in the art, which differ from one another by changes in nucleotide and amino acid sequence. For example, isolate HCV J1.1 is described in Kubo et al (1989) Japan. Nucl. Acids Res. 17:10367-10372; Takeuchi et al.(1990) Gene 91:287-291; Takeuchi et al. (1990) J. Gen. Virol. 71:3027-3033; and Takeuchi et al. (1990) Nucl. Acids Res. 18:4626. The complete coding sequences of two independent isolates, HCV-J and BK, are described by Kato et al., (1990) Proc. Natl. Acad. Sci. USA 87:9524-9528 and Takamizawa et al., (1991) J. Virol. 65:1105-1113, respectively. HCV-1 isolates are described by Choo et al. (1990) Brit. Med. Bull. 46:423-441; Choo et al. (1991) Proc. Natl. Acad. Sci. USA 88:2451-2455 and Han et al. (1991) Proc. Natl. Acad. Sci. USA 88:1711-1715. HCV isolates HC-J1 and HC-J4 are described in Okamoto et al. (1991) Japan J. Exp. Med. 60:167-177. HCV isolates HCT 18~, HCT 23, Th, HCT 27, EC1 and EC10 are described in Weiner et al. (1991) Virol. 180:842-848. HCV isolates Pt-1, HCV-K1 and HCV-K2 are described in Enomoto et al. (1990) Biochem. Biophys. Res. Commun. 170:1021-1025. HCV isolates A, C, D & E are described in Tsukiyama-Kohara et al. (1991) Virus Genes 5:243-254. HCV polypeptides for use in the compositions and methods of the invention can be obtained from any of the above cited strains of HCV or from newly discovered isolates isolated from tissues or fluids of infected patients.

Other preferred antigens for use in the subject compositions and methods are those derived from HIV. The HIV genome includes the regions known as Gag (p55gag), Pol, Vif, Vpr, Tat, Rev, Vpu, Env and/or Nef. HIV antigens from any of these regions, from any of the various subtypes, such as HIV subtype B and HIV subtype C, as well as any of the various isolates, such as SF162, SF2, AF110965, AF110967, AF110968, AF110975, 8_5_$_{TV}$1_C.ZA, 8_2_TV1_C.ZA or 12-5_1_TV2_C.ZA, and the like, will find use with the present methods. The various regions of the HIV genome are shown in Table 2, with numbering relative to 8_5_TV1_C.ZA (FIGS. 5A-5D; SEQ ID NO: 5). However, it will be readily apparent to one of ordinary skill in the art in view of the teachings of the present disclosure how to determine corresponding regions in other HIV strains or variants (e.g., isolates $HIV_{IIIb}$, $HIV_{SF2}$, $HIV-1_{SF162}$, $HIV-1_{SF170}$, $HIV_{LAV}$, $HIV_{LAI}$, $HIV_{MN}$, $HIV-1_{CM235}$, $HIV-1_{US4}$, other HIV-1 strains from diverse subtypes (e.g., subtypes, A through G, and O), HIV-2 strains and diverse subtypes (e.g., $HIV-2_{UC1}$ and $HIV-2_{UC2}$), and simian immunodeficiency virus (SIV). (See, e.g., Virology, 3rd Edition (W. K. Joklik ed. 1988); *Fundamental Virology*, 2nd Edition (B. N. Fields and D. M. Knipe, eds. 1991); *Virology*, 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify the various regions).

The envelope protein of HIV is a glycoprotein of about 160 kd (gp160). During virus infection of the host cell, gp160 is cleaved by host cell proteases to form gp120 and the integral membrane protein, gp41. The gp41 portion is anchored in the membrane bilayer of virion, while the gp120 segment protrudes into the surrounding environment. gp120 and gp41 are more covalently associated and free gp120 can be released from the surface of virions and infected cells. The gp120 polypeptide is instrumental in mediating entry into the host cell. Recent studies have indicated that binding of CD4 to gp120 induces a conformational change in Env that allows for binding to a co-receptor (e.g, a chemokine receptor) and subsequent entry of the virus into the cell. (Wyatt, R., et al. (1998) *Nature* 393:705-711; Kwong, P., et al.(1998) *Nature* 393:648-659). CD4 is bound into a depression formed at the interface of the outer domain, the inner domain and the bridging sheet of gp120.

TABLE 2

| Regions of the HIV Genome relative to 8_5_TV1_C.ZA | |
|---|---|
| Region | Position in nucleotide sequence |
| 5'LTR | 1-636 |
| U3 | 1-457 |
| R | 458-553 |
| U5 | 554-636 |
| NFkB II | 340-348 |
| NFkB I | 354-362 |
| Sp1 III | 379-388 |
| Sp1 II | 390-398 |
| Sp1 I | 400-410 |
| TATA Box | 429-433 |

TABLE 2-continued

Regions of the HIV Genome relative to 8_5_TV1_C.ZA

| Region | Position in nucleotide sequence |
| --- | --- |
| TAR | 474-499 |
| Poly A signal | 529-534 |
| PBS | 638-655 |
| p7 binding region, packaging signal | 685-791 |
| Gag (p55gag): | 792-2285 |
| p17 | 792-1178 |
| p24 | 1179-1871 |
| Cyclophilin A bdg. | 1395-1505 |
| MHR | 1632-1694 |
| p2 | 1872-1907 |
| p7 | 1908-2072 |
| Frameshift slip | 2072-2078 |
| p1 | 2073-2120 |
| p6gag | 2121-2285 |
| Zn-motif I | 1950-1991 |
| Zn-motif II | 2013-2054 |
| Pol: | 2072-5086 |
| p6Pol | 2072-2245 |
| Prot | 2246-2542 |
| p66RT | 2543-4210 |
| p15RNaseH | 3857-4210 |
| p31Int | 4211-5086 |
| Vif: | 5034-5612 |
| Hydrophilic region | 5292-5315 |
| Vpr: | 5552-5839 |
| Oligomerization | 5552-5677 |
| Amphipathic α-helix | 5597-5653 |
| Tat: | 5823-6038 and 8417-8509 |
| Tat-1 exon | 5823-6038 |
| Tat-2 exon | 8417-8509 |
| N-terminal domain | 5823-5885 |
| Trans-activation domain | 5886-5933 |
| Transduction domain | 5961-5993 |
| Rev: | 5962-6037 and 8416-8663 |
| Rev-1 exon | 5962-6037 |
| Rev-2 exon | 8416-8663 |
| High-affinity bdg. site | 8439-8486 |
| Leu-rich effector domain | 8562-8588 |
| Vpu: | 6060-6326 |
| Transmembrane domain | 6060-6161 |
| Cytoplasmic domain | 6162-6326 |
| Env (gp160): | 6244-8853 |
| Signal peptide | 6244-6324 |
| gp120 | 6325-7794 |
| V1 | 6628-6729 |
| V2 | 6727-6852 |
| V3 | 7150-7254 |
| V4 | 7411-7506 |
| V5 | 7663-7674 |
| C1 | 6325-6627 |
| C2 | 6853-7149 |
| C3 | 7255-7410 |
| C4 | 7507-7662 |
| C5 | 7675-7794 |
| CD4 binding | 7540-7566 |
| gp41 | 7795-8853 |
| Fusion peptide | 7789-7842 |
| Oligomerization domain | 7924-7959 |
| N-terminal heptad repeat | 7921-8028 |
| C-terminal heptad repeat | 8173-8280 |
| Immunodominant region | 8023-8076 |
| Nef: | 8855-9478 |
| Myristoylation | 8858-8875 |
| SH3 binding | 9062-9091 |
| Polypurine tract | 9128-9154 |
| SH3 binding | 9296-9307 |

It will be apparent that one of skill in the art can readily align any sequence to that shown in Table 2 to determine relative locations of any particular HIV gene, as described above. For example, using one of the alignment programs described herein (e.g., BLAST), other HIV genomic sequences can be aligned with 8_5_TV1_C.ZA (Table 2) and locations of genes determined. Polypeptide sequences can be similarly aligned.

Recombinant methods of obtaining the various HIV antigens once the region desired is identified are well known in the art and are described further below. See, also, U.S. Pat. No. 5,614,612, incorporated herein by reference in its entirety.

Moreover, modified sequences of any of these HIV regions, such as modified gp120 and p55gag, can be used in the subject methods. Sequences can be modified for optimum codon usage to simulate human codons and to reduce toxicity. Such modified sequences are known in the art and the sequences and methods of producing the same are described in detail in commonly owned International Publication Nos. WO 00/39304 and WO 00/39302, as well as in International Publication No. WO 98/34640, all incorporated herein by reference in their entireties.

The subject methods are also particularly useful for antigens derived from *Neisseria* spp., such as *N. meningitidis*, the causative agent of bacterial meningitis and sepsis. Meningococci are divided into serological groups based on the immunological characteristics of capsular and cell wall antigens. Currently recognized serogroups include A, B, C, W-135, X, Y, Z and 29E. For purposes of the present invention, a meningococcal antigen may be derived from any of the various known serogroups. The polysaccharides responsible for the serogroup specificity have been purified from several of these groups, including A, B, C, W-135 and Y. Effective capsular polysaccharide-based vaccines have been developed against meningococcal disease caused by serogroups A, C, Y and W135 and any of these vaccine antigens will find use in the present compositions and methods. See, e.g., International Publication Nos. WO 96/29412, WO 96/14086, WO 99/57280, WO 00/22430, WO 99/24578, WO 99/36544, as well as Tettelin et al. (2000) *Science* 287:1809-1815 and Pizza et al. (2000) *Science* 287:1816-1820, all incorporated by reference herein in their entireties, for a description of various meningococcal protein antigens that will find use herein. Additionally, saccharide antigens, such as those from *N. meningitidis* serogroup A, C W135 and/or Y, such as described in Costantino et al. (1992) *Vaccine* 10:691-698 and Costantino et al. (1999) *Vaccine* 17:1251-1263 will find use herein. Other useful *Neisseria* antigens include those derived from *N. gonorrhorea*, for example, those described in International Publication Nos. WO 99/57280, WO 99/24578 and WO 99/36544.

For example, *N. meningitidis* serogroup B (termed "MenB" herein) accounts for a large percentage of bacterial meningitis in infants and children residing in the U.S. and Europe. Accordingly, antigens derived from MenB are particularly useful with the present compositions and methods, such as any of the antigens expressed by the various open reading frames (ORFs) of the MenB genome. See, e.g., International Publication No. WO 99/57280. Examples of such antigens include MenB proteins 961 and 287. Other meningococcal antigens for use herein include derivatives of the capsular MenB polysaccharide (termed "MenB PS derivatives" herein). MenB PS is a homopolymer of (N-acetyl (α 2->8) neuraminic acid. Examples of MenB PS derivatives include $C_3$-$C_8$ N-acyl-substituted MenB PS derivatives as described in EP Publication No. 504,202 B. Similarly, U.S. Pat. No. 4,727,136 describes an N-propionylated MenB PS molecule, termed "NPr-MenB PS." Also useful are molecular mimetics of unique epitopes of MenB PS as described in U.S. Pat. No. 6,030,619. Additionally, outer membrane vesicle preparations from MenB, such as those described in International Patent Application PCT/IB01/00166, Bjune et al. (1991) *Lancet* 338:1093-1096, Fukasawa et al. (1999) *Vaccine* 17:2951-2958 and Rosenquist et al. (1998) *Dev. Biol. Stand.* 92:323-333. All of the above references are incorporated herein by reference in their entireties.

The complete genomic sequence of MenB, strain MC58, has been described. Tettelin et al., *Science* (2000) 287:1809. Several proteins that elicited serum bactericidal antibody responses have been identified by whole genome sequencing. Many of these proteins have sequences that are highly conserved among *Neisseria meningitidis*. Pizza et al., *Science* (2000) 287:1816. Accordingly, such antigens will find use herein.

As explained above, the selected antigens may be used in their entireties or immunogenic fragments thereof, as well as immunogenic variants, can be used. Thus, the selected antigens can be modified by deletions, insertions, or conservative or nonconservative amino acid substitutions, provided that a immunogenicity is retained.

The antigens for use herein can be produced using standard techniques of molecular biology. For example, polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from viral nucleic acid molecules, using techniques described in the art. For HCV, such techniques are described in, e.g., Houghton et al., U.S. Pat. No. 5,350,671. The gene of interest can also be produced synthetically, rather than cloned. The molecules can be designed with appropriate codons for the particular sequence. The complete sequence is then assembled from overlapping oligonucleotides prepared by standard methods and assembled into a complete coding sequence. See, e.g., Edge (1981) *Nature* 292:756; Nambair et al. (1984) *Science* 223:1299; and Jay et al. (1984) *J. Biol. Chem.* 259:6311.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. In particular, one method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al. (1991) *Proc. Natl. Acad. Sci. USA* 88:4084-4088. Additionally, oligonucleotide directed synthesis (Jones et al. (1986) *Nature* 54:75-82), oligonucleotide directed mutagenesis of pre-existing nucleotide regions (Riechmann et al. (1988) *Nature* 332:323-327 and Verhoeyen et al. (1988) *Science* 239:1534-1536), and enzymatic filling-in of gapped oligonucleotides using $T_4$ DNA polymerase (Queen et al. (1989) *Proc. Natl. Acad. Sci. USA* 86:10029-10033) can be used to provide molecules having altered or enhanced antigen-binding capabilities and immunogenicity.

Once coding sequences have been prepared or isolated, such sequences can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements.

The coding sequence is then placed under the control of suitable control elements, depending on the system to be used for expression. Thus, the coding sequence can be placed under the control of a promoter, ribosome binding site (for bacterial expression) and, optionally, an operator, so that the DNA sequence of interest is transcribed into RNA by a suitable transformant. The coding sequence may or may not contain a signal peptide or leader sequence which can later be removed by the host in post-translational processing. See, e.g., U.S. Pat. Nos. 4,431,739; 4,425,437; 4,338,397.

In addition to control sequences, it may be desirable to add regulatory sequences which allow for regulation of the expression of the sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector. For example, enhancer elements may be used herein to increase expression levels of the constructs. Examples include the SV40 early gene enhancer (Dijkema et al. (1985) *EMBO J.* 4:761), the enhancer/promoter derived from the long terminal repeat (LTR) of the Rous Sarcoma Virus (Gorman et al. (1982) *Proc. Natl. Acad. Sci. USA* 79:6777) and elements derived from human CMV (Boshart et al. (1985) *Cell* 41:521), such as elements included in the CMV intron A sequence (U.S. Pat. No. 5,688,688). The expression cassette may further include an origin of replication for autonomous replication in a suitable host cell, one or more selectable markers, one or more restriction sites, a potential for high copy number and a strong promoter.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the molecule of interest may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

As explained above, it may also be desirable to produce mutants or analogs of the polypeptide of interest. Mutants or analogs of the antigen for use in the subject compositions may be prepared by the deletion of a portion of the sequence encoding the polypeptide of interest, by insertion of a sequence, and/or by substitution of one or more nucleotides within the sequence. Techniques for modifying nucleotide sequences, such as site-directed mutagenesis, and the like, are well known to those skilled in the art. See, e.g., Sambrook et al., supra; Kunkel, T. A. (1985) *Proc. Natl. Acad. Sci. USA* (1985) 82:448; Geisselsoder et al. (1987) *BioTechniques* 5:786; Zoller and Smith (1983) *Methods Enzymol.* 100:468; Dalbie-McFarland et al. (1982) *Proc. Natl. Acad. Sci USA* 79:6409.

The molecules can be expressed in a wide variety of systems, including insect, mammalian, bacterial, viral and yeast expression systems, all well known in the art.

For example, insect cell expression systems, such as baculovirus systems, are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook et al., supra. Yeast expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human embryonic kidney cells, human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus spp.*, will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica.* Insect cells for use with baculovirus expression vectors include, inter alia, *Aedes aegypti, Autographa californica, Bombyx mori, Drosophila melanogaster, Spodoptera frugiperda*, and *Trichoplusia ni*.

Nucleic acid molecules comprising nucleotide sequences of interest can be stably integrated into a host cell genome or maintained on a stable episomal element in a suitable host cell using various gene delivery techniques well known in the art. See, e.g., U.S. Pat. No. 5,399,346.

Depending on the expression system and host selected, the molecules are produced by growing host cells transformed by an expression vector described above under conditions whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art.

Type 1 Interferon Adjuvant Compositions

One or more antigens, produced as described above, are administered with an adjuvant composition which includes a type 1 interferon inducer, an antigen delivery system and/or an immunostimulatory molecule. The antigen may be administered either prior to, concurrent with, or subsequent to, delivery of the adjuvant composition. If administered separately, the antigen will be provided in a composition such as described further below. Alternatively, the antigen may be provided in the adjuvant composition.

Type 1 interferon inducers elicit production of type 1 interferon (IFN-1) above base levels. IFN-α and IFN-β are the major species of type 1 interferons. Thus, IFN-1 levels can be assessed using assays that measure IFN-α and IFN-β. Such assays are well known in the art. One representative assay measures the ability of the sample to inhibit the cytopathic effect of vesicular stomatitis virus on L cells in monolayer culture. See, e.g., Le Bon et al., *Immunity* (2001) 14:461-470. Another assay measures antiviral activity in culture using encephalomyocarditis virus (EMCV) as a test virus. See, e.g., Tazulakhova et al., *J. Interfer. Cyotkine Res.* (2001) 21:65-73.

Type 1 interferon inducers include natural compounds such as low molecular weight phenols of natural origin such as, but not limited to aromatic hydrocarbons which are derivatives of gossypol including Megasin, Kagocel ("NIARnedic-plus," Moscow, Russia), Savrats, Ragosin (N.F. Gamaleya Institute, Moscow, Russia) and Gosalidon; polymers including double-stranded RNA (see further below); synthetic compounds such as, but not limited to, fluorenones such as Amixin (OOO "Lancepharm," Moscow, Russia), and nitric bases such as the acridanones Neovir and Cycloferon (NTFF "Polysan," St. Petersburg, Russia); and polynucleotides such as Ampligen (poly[I-$C_{12}$U], Poludan and polyguacil.

One particularly preferred type 1 interferon inducer for use with the subject compositions and methods is double-stranded RNA (dsRNA). Double-stranded RNAs for use in the adjuvant compositions can be from various sources. A number of organisms naturally produce dsRNA, including yeasts and viruses. DsRNA from such sources is made up of intermittent riboguanylic acid-ribocytidylic acid ([rG-rC]) and riboadenylic acid-polyribouridylic acid ([rA-rU]) base pairs. It appears that all viruses except single-stranded DNA viruses, produce dsRNA. Viral dsRNA exists either in the form of duplexes of complementary strands or in the form of intramolecular secondary structure within single-stranded RNA. Viral sources of dsRNA for dsRNA viruses (genomic), ssRNA viruses (transcription intermediates), dsDNA viruses (symmetrical transcription followed by RNA-RNA annealing), and retroviruses (secondary structure in viral mRNA) are known and described in, e.g., Majde, J. A., *J. Interfer. Cytokine Res.* (2000) 20:259-272 and Jacobs and Langland, *Virology* (1996) 219:339-349.

Particular sources of viral dsRNA include, but are not limited to, dsRNAs from Mengo virus-infected cells (Falcoff et al., *Antimicrob. Agents Chemother.* (1973) 3:590-598); dsRNAs from reoviruses and fungal viruses (Field et al., *Proc. Natl. Acad. Sci. USA* (1967) 58:1004-1010, De Benedetti et al., *J. Virol.* (1985) 54:408-413); retrovirus dsRNA (Jacobs and Langland, *Virology* (1996) 219:339-349), such as from HIV-1 (Maitra et al., *Virology* (1994) 204:823-827); dsRNA extracted from picornavirus-infected cells (Falcoff et al., *Antimicrob. Agents Chemother.* (1973) 3:590-598); dsRNA from influenza-infected lungs (Majde et al., *Microb. Pathogen.* (1991) 10:105-115); dsRNA from infected plant cells (Lin and Langenberg, *Virology* (1985) 142:291-298); dsRNA from togaviruses (Stollar, B. D., *Crit. Rev. Biochem.* (1975) 3:45-69); dsRNA from rubella-virus infected cells (Lee et al., *Virology* (1994) 200:307-312); dsRNA from Semliki Forest virus-infected cells (Lee et al., *Virology* (1994) 200:307-312); dsRNA from dengue virus-infected cells (MacKenzie et al., *Virology* (1996) 220:232-240); the dsRNAs known as Larifan (Riga, Latvia) and Ridostin ("Diapharam" NOP "VECTOR," Berdsk, Russia). Any of these various dsRNAs, as well as dsRNAs from other sources, will find use with the present compositions and methods.

DsRNA from infected cells is readily obtained using standard methods of nucleic acid extraction, such as phenol extraction techniques, and as described in several of the publications above. See, e.g., Falcoff et al., *Antimicrob. Agents Chemother.* (1973) 3:590-598; Fayet et al., *Prog. Immunobiol. Standard.* (1972) 5:267-273; Majde et al., *Microb. Pathogen.* (1991) 10:105-115)

A number of synthetic dsRNAs are also known and will find use herein and are synthesized using techniques well known and described in the art. Such synthetic dsRNAs include, but are not limited to, polyriboinosinic-polyribocytidylic acid (poly[rI-rC]) and polyriboguanylic-polyribocytidylic acid (poly[rG-rC]) (see, e.g., Michelson et al., *Prog. Nuc. Acid Res. Mol. Biol.* (1967) 6:83-141); polyriboadenylic-polyribouridylic acid (poly[rA-rU]); low molecular weight dsRNA of mixed base composition, such as, but not limited to, a synthetic dsRNA with 309 bp (Haines et al., *J. Biol. Chem.* (1992) 267:18315-18319); as well as the synthetic mismatched dsRNAs described in, e.g., U.S. Pat. Nos. 5,906,980 and 5,258,369, incorporated herein by reference in their entireties. Moreover, dsRNAs with modified backbones can be made using techniques well known in the art. Synthetic dsRNAs can have a variety of lengths and generally range from 50-250 bps in length, such as 75-150, 85-100, or any integer between 50-250 bps in length. A representative synthetic 90mer dsRNA that includes a 90mer strand of riboinosinic acid and a 90mer strand of ribocytidylic acid annealed thereto, is described below in the examples.

As explained above, the use of an antigen delivery system, i.e., particulate delivery systems, along with a type 1 interferon inducer, provides for significantly enhanced immune responses as compared with the use of a type 1 interferon inducer alone. Thus, according to the invention, the type 1 interferon inducer is combined with an antigen delivery system and/or an immunostimulatory molecule prior to delivery. Particular antigen delivery systems for use herein include submicron oil-in-water emulsions, cationic emulsions, microparticles, ISCOMs, liposomes, and the like.

In particular, submicron oil-in water emulsions for use herein include nontoxic, metabolizable oils and commercial emulsifiers. Examples of nontoxic, metabolizable oils include, without limitation, vegetable oils, fish oils, animal oils or synthetically prepared oils. Fish oils, such as cod liver oil, shark liver oils and whale oils, are preferred, with squalene, 2,6,10,15,19,23-hexamethyl-2,6,10,14,18,22-tetracosahexacne, found in shark liver oil, particularly preferred. The oil component will be present in an amount of from about 0.5% to about 20% by volume, preferably in an amount up to about 15%, more preferably in an amount of from about 1% to about 12% and most preferably from 1% to about 4% oil.

The aqueous portion of the adjuvant can be buffered saline or unadulterated water. Since the compositions are intended for parenteral administration, it is preferable to make up the final solutions so that the tonicity, i.e., osmolality, is essentially the same as normal physiological fluids, in order to prevent post-administration swelling or rapid absorption of the composition due to differential ion concentrations between the composition and physiological fluids. If saline is used rather than water, it is preferable to buffer the saline in order to maintain a pH compatible with normal physiological conditions. Also, in certain instances, it may be necessary to maintain the pH at a particular level in order to insure the stability of certain composition components. Thus, the pH of the compositions will generally be pH 6-8 and pH can be maintained using any physiologically acceptable buffer, such as phosphate, acetate, tris, bicarbonate or carbonate buffers, or the like. The quantity of the aqueous agent present will generally be the amount necessary to bring the composition to the desired final volume.

Emulsifying agents suitable for use in the oil-in-water formulations include, without limitation, sorbitan-based nonionic surfactants such as a sorbitan mono-, di-, or triester, for example those commercially available under the name of SPAN™ or ARLACEL™, such as SPAN™85 (sorbitan trioleate); polyoxyethylene sorbitan mono-, di-, or triesters commercially known by the name TWEEN™, such as TWEEN 80™ (polyoxyelthylenesorbitan monooleate); polyoxyethylene fatty acids available under the name MYRJ™; polyoxyethylene fatty acid ethers derived from lauryl, acetyl, stearyl and oleyl alcohols, such as those known by the name of BRIJ™; and the like. These substances are readily available from a number of commercial sources, including Sigma, St. Louis, Mo. and ICI America's Inc., Wilmington, Del. These emulsifying agents may be used alone or in combination. The emulsifying agent will usually be present in an amount of 0.02% to about 2.5% by weight (w/v), preferably 0.05% to about 1%, and most preferably 0.01% to about 0.5. The amount present will generally be about 20-30% of the weight of the oil used.

The emulsions can also contain other immunostimulating agents, such as muramyl peptides, including, but not limited to, N-acetyl-muramyl-L-threonyl-D-isoglutamine (thr-MDP), N-acteyl-normuramyl-L-alanyl-D-isogluatme (nor-MDP), -acetylmuramyl-L-alanyl-D-isogluatminyl-L-alanine-2-(1'-2'-dipalmitoyl-sn-glycero-3-huydroxyphosphoryloxy)-ethylamine (MTP-PE), etc. Immunostimulating bacterial cell wall components, such as monophosphorylipid A (MPL), trehalose dimycolate (TDM), and cell wall skeleton (CWS), may also be present. Alternatively, the emulsions may be free of these agents. However, the submicron oil-in-water emulsions of the present invention may be devoid of any polyoxypropylene-polyoxyethylene (POP-POE) block copolymers. For a description of various suitable submicron oil-in-water emulsion formulations for use with the present invention, as well as immunostimulating agents, see, e.g., International Publication No. WO 90/14837; *Remington: The Science and Practice of Pharmacy*, Mack Publishing Company, Easton, Pa., 19th edition, 1995; Van Nest et al., "Advanced adjuvant formulations for use with recombinant subunit vaccines," In *Vaccines 92, Modern Approaches to New Vaccines* (Brown et al., ed.) Cold Spring Harbor Laboratory Press, pp. 57-62 (1992); Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York (1995) pp. 277-296; and U.S. Pat. No. 6,299,884, incorporated herein by reference in its entirety.

In order to produce submicron particles, i.e., particles less than 1 micron in diameter and in the nanometer size range, a number of techniques can be used. For example, commercial emulsifiers can be used that operate by the principle of high shear forces developed by forcing fluids through small apertures under high pressure. Examples of commercial emulsifiers include, without limitation, Model 110Y microfluidizer (Microfluidics, Newton, Mass.), Gaulin Model 30CD (Gaulin, Inc., Everett, Mass.), and Rainnie Minilab Type 8.30H (Miro Atomizer Food and Dairy, Inc., Hudson, Wis.). The appropriate pressure for use with an individual emulsifier is readily determined by one of skill in the art. For example, when the Model 110Y microfluidizer is used, operation at 5000 to 30,000 psi produces oil droplets with diameters of about 100 to 750 nm.

The size of the oil droplets can be varied by changing the ratio of detergent to oil (increasing the ratio decreases droplet size), operating pressure (increasing operating pressure reduces droplet size), temperature (increasing temperature decreases droplet size), and adding an amphipathic immunostimulating agent (adding such agents decreases droplet size). Actual droplet size will vary with the particular detergent, oil and immunostimulating agent (if any) and with the particular operating conditions selected. Droplet size can be verified by use of sizing instruments, such as the commercial Sub-Micron Particle Analyzer (Model N4MD) manufactured by the Coulter Corporation, and the parameters can be varied using the guidelines set forth above until substantially all droplets are less than 1 micron in diameter, preferably less than about 0.8 microns in diameter, and most preferably less than about 0.5 microns in diameter. By substantially all is meant at least about 80% (by number), preferably at least about 90%, more preferably at least about 95%, and most preferably at least about 98%. The particle size distribution is typically Gaussian, so that the average diameter is smaller than the stated limits.

Particularly preferred submicron oil-in-water emulsions for use herein are squalene/water emulsions optionally containing varying amounts of MTP-PE, such as a submicron oil-in-water emulsions containing 4-5% w/v squalene, 0.25-1.0% w/v TWEEN 80™ (polyoxyelthylenesorbitan monooleate), and/or 0.25-1.0% SPAN 85™ (sorbitan trioleate), and optionally, N-acetylmuramyl-L-alanyl-D-isogluatminyl-L-alanine-2-(1'-2'-dipalmitoyl-sn-glycero-3-huydroxyphosphoryloxy)-ethylamine (MTP-PE), for example, the submicron oil-in-water emulsion known as "MF59" (International Publication No. WO 90/14837; U.S. Pat. No. 6,299,884, incorporated herein by reference in its entirety; and Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277-296). MF59 contains 4-5% w/v Squalene (e.g., 4.3%), 0.25-0.5% w/v TWEEN 80™, and 0.5% w/v SPAN 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 μg/dose, more preferably 0-250 μg/dose and most preferably, 0-100 μg/dose. As used herein, the term "MF59-0" refers to the above submicron oil-in-water emulsion lacking MTP-PE, while the term "MF59-100" contains 100 μg MTP-PE per dose, and so on. MF69, another submicron oil-in-water emulsion for use herein, contains 4.3% w/v squalene, 0.25% w/v TWEEN 80™, and 0.75% w/v SPAN 85™ and optionally MTP-PE. Yet another submicron oil-in-water emulsion is MF75, also known as SAF, containing 10% squalene, 0.4% TWEEN 80™, 5% pluronic-blocked polymer L121, and thr-MDP, also microfluidized into a submicron emulsion. MF75-100 includes 100 μg of MTP-PE per dose.

Submicron oil-in-water emulsions, methods of making the same and immunostimulating agents, such as muramyl peptides, for use in the compositions, are described in detail in International Publication No. WO 90/14837 and U.S. Pat. No. 6,299,884, incorporated herein by reference in its entirety.

Generally, for purposes of the present invention, approximately 10 μg to 10 mg of dsRNA, more preferably 500 μg to 5 mg, even more preferably 100 μg to 1 mg, such as 50 . . . 40 . . . 30 . . . 20 . . . 10 μg and so on, to 0.5 mg dsRNA, and any integer within these ranges, will be present in the submicron oil-in-water emulsions described herein.

Microparticles will also find use as antigen delivery systems. The term "microparticle" as used herein, refers to a particle of about 100 nm to about 150 μm in diameter, more preferably about 200 nm to about 30 μm in diameter, and most preferably about 500 nm to about 10 μm in diameter. Preferably, the microparticle will be of a diameter that permits parenteral administration without occluding needles and capillaries. Microparticle size is readily determined by techniques well known in the art, such as photon correlation spectroscopy, laser diffractometry and/or scanning electron microscopy.

Microparticles for use herein will be formed from materials that are sterilizable, non-toxic and biodegradable. Such materials include, without limitation, poly(α-hydroxy acid), polyhydroxybutyric acid, polycaprolactone, polyorthoester, polyanhydride, polyvinyl alcohol and ethylenevinyl acetate. Preferably, microparticles for use with the present invention are derived from a poly(α-hydroxy acid), in particular, from a poly(lactide) ("PLA") (see, e.g., U.S. Pat. No. 3,773,919) or a copolymer of D,L-lactide and glycolide or glycolic acid, such as a poly(D,L-lactide-co-glycolide) ("PLG" or "PLGA") (see, e.g., U.S. Pat. No. 4,767,628), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the desired dose of polypeptide and the disorder to be treated. These parameters are discussed more fully below. Biodegradable polymers for manufacturing microparticles useful in the present invention are readily commercially available from, e.g., Boehringer Ingelheim, Germany and Birmingham Polymers, Inc., Birmingham, Ala.

Particularly preferred polymers for use herein are PLA and PLG polymers. These polymers are available in a variety of molecular weights, and the appropriate molecular weight to provide the desired release rate for the polypeptide in question is readily determined by one of skill in the art. Thus, e.g., for PLA, a suitable molecular weight will be on the order of about 2000 to 250,000. For PLG, suitable molecular weights will generally range from about 10,000 to about 200,000, preferably about 15,000 to about 150,000, and most preferably about 50,000 to about 100,000.

If a copolymer such as PLG is used to form the microparticles, a variety of lactide:glycolide ratios will find use herein and the ratio is largely a matter of choice, depending in part on the rate of degradation desired. For example, a 50:50 PLG polymer, containing 50% D,L-lactide and 50% glycolide, will provide a fast resorbing copolymer while 75:25 PLG degrades more slowly, and 85:15 and 90:10, even more slowly, due to the increased lactide component. It is readily apparent that a suitable ratio of lactide:glycolide is easily determined by one of skill in the art based on the nature disorder to be treated. Moreover, mixtures of microparticles with varying lactide:glycolide ratios will find use in the formulations in order to achieve the desired release kinetics. PLG copolymers with varying lactide:glycolide ratios and molecular weights are readily available commercially from a number of sources including from Boehringer Ingelheim, Germany and Birmingham Polymers, Inc., Birmingham, Ala. These polymers can also be synthesized by simple polycondensation of the lactic acid component using techniques well known in the art, such as described in Tabata et al., *J. Biomed. Mater. Res.* (1988) 22:837-858.

The microparticles are prepared that either contain the desired molecule (e.g., dsRNA and/or antigen) or that have the molecule adsorbed to the surface. Several techniques are known in the art for preparing such microparticles. For example, double emulsion/solvent evaporation techniques, such as described in U.S. Pat. No. 3,523,907 and Ogawa et al., *Chem. Pharm. Bull.* (1988) 36:1095-1103, can be used herein to make the microparticles. These techniques involve the formation of a primary emulsion consisting of droplets of polymer solution, which is subsequently mixed with a continuous aqueous phase containing a particle stabilizer/surfactant.

More particularly, a water-in-oil-in-water (w/o/w) solvent evaporation system can be used to form the microparticles, as described by O'Hagan et al., *Vaccine* (1993) 11:965-969 and Jeffery et al., Pharm. Res. (1993) 10:362. In this technique, the particular polymer is combined with an organic solvent, such as ethyl acetate, dimethylchloride (also called methylene chloride and dichloromethane), acetonitrile, acetone, chloroform, and the like. The polymer will be provided in about a 2-15%, more preferably about a 4-10% and most preferably, a 6% solution, in organic solvent. The polymer solution is emulsified using e.g, an homogenizer. The emulsion is then combined with a larger volume of an aqueous solution of an emulsion stabilizer such as polyvinyl alcohol (PVA) or polyvinyl pyrrolidone. The emulsion stabilizer is typically provided in about a 2-15% solution, more typically about a 4-10% solution. The mixture is then homogenized to produce a stable w/o/w double emulsion. Organic solvents are then evaporated.

The formulation parameters can be manipulated to allow the preparation of small (<5 μm) and large (>30 82 m) microparticles. See, e.g., Jeffery et al., *Pharm. Res.* (1993) 10:362-368; McGee et al., *J. Microencap.* (1996). For example, reduced agitation results in larger microparticles, as does an increase in internal phase volume. Small particles are produced by low aqueous phase volumes with high concentrations of PVA.

Microparticles can also be formed using spray-drying and coacervation as described in, e.g., Thomasin et al., *J. Controlled Release* (1996) 41:131; U.S. Pat. No. 2,800,457; Masters, K. (1976) *Spray Drying* 2nd Ed. Wiley, N.Y.; air-suspension coating techniques, such as pan coating and Wurster coating, as described by Hall et al., (1980) The "Wurster Process" in *Controlled Release Technologies: Methods, Theory, and Applications* (A. F. Kydonieus, ed.), Vol. 2, pp. 133-154 CRC Press, Boca Raton, Fla. and Deasy, P. B., *Crit. Rev. Ther. Drug Carrier Syst.* (1988) S(2):99-139; and ionic gelation as described by, e.g., Lim et al., *Science* (1980) 210:908-910.

Particle size can be determined by, e.g., laser light scattering, using for example, a spectrometer incorporating a helium-neon laser. Generally, particle size is determined at room temperature and involves multiple analyses of the sample in question (e.g., 5-10 times) to yield an average value for the particle diameter. Particle size is also readily determined using scanning electron microscopy (SEM).

Prior to use of the microparticles, protein content (e.g., if the microparticle contains or has the antigen of interest adsorbed thereto) may be determined so that an appropriate amount of the microparticles may be delivered to the subject in order to elicit an appropriate immunological response. Protein content of the microparticles can be determined according to methods known in the art, such as by disrupting the microparticles and extracting the entrapped polypeptide. For example, microparticles can be dissolved in dimethylchloride and the protein extracted into distilled water, as described in, e.g., Cohen et al., *Pharm. Res.* (1991) 8:713; Eldridge et al., *Infect. Immun.* (1991) 59:2978; and Eldridge et al., *J. Controlled Release* (1990)11:205. Alternatively, microparticles can be dispersed in 0.1 M NaOH containing 5% (w/v) SDS. The sample is agitated, centrifuged and the supernatant assayed for the particular polypeptide using an appropriate assay. See, e.g., O'Hagan et al., *Int. J. Pharm.* (1994) 103:37-45.

If antigen is associated with the microparticle, the particles will preferably comprise from about 0.1% to about 40% (w/w) polypeptide, more preferably about 2% to about 25% (w/w) polypeptide, and even more preferably about 3%-4% to about 18%-20% (w/w) polypeptide. The load of polypeptide in the microparticles will depend on the desired dose and the condition being treated, as discussed in more detail below.

Following preparation, microparticles can be stored as is or freeze-dried for further use. In order to adsorb dsRNA and/or antigen to the microparticles, the microparticle preparation is simply mixed with the dsRNA and/or the antigen of interest and the resulting formulation can again be lyophilized prior to use. Generally, for purposes of the present invention, approximately 10 μg to 10 mg of dsRNA, more preferably 500 μg to 5 mg, even more preferably 100 μg to 1 mg, such as 50 . . . 40 . . . 30 . . . 20 . . . 10 μg and so on, to 0.5 mg dsRNA, and any integer within these ranges, will be adsorbed or entrapped with the microparticles described herein.

One preferred method for adsorbing macromolecules onto prepared microparticles is described in International Publication No. WO 00/050006, incorporated herein by reference in its entirety. Briefly, microparticles are rehydrated and dispersed to an essentially monomeric suspension of microparticles using dialyzable anionic or cationic detergents. Useful detergents include, but are not limited to, any of the various N-methylglucamides (known as MEGAs), such as heptanoyl-N-methylglucamide (MEGA-7), octanoyl-N-methylglucamide (MEGA-8), nonanoyl-N-methylglucamide (MEGA-9), and decanoyl-N-methyl-glucamide (MEGA-10); cholic acid; sodium cholate; deoxycholic acid; sodium deoxycholate; taurocholic acid; sodium taurocholate; taurodeoxycholic acid; sodium taurodeoxycholate; 3-[(3-cholamidopropyl)dimethylammonio]-1-propane-sulfonate (CHAPS); 3-[(3-cholamidopropyl) dimethylammonio]-2-hydroxy-1-propane-sulfonate (CHAPSO); -dodecyl-N,N-dimethyl-3-ammonio-1-propane-sulfonate (ZWITTERGENT 3-12); N,N-bis-(3-D-gluconeamidopropyl)-deoxycholamide (DEOXY-BIGCHAP); -octylglucoside; sucrose monolaurate; glycocholic acid/sodium glycocholate; laurosarcosine (sodium salt); glycodeoxycholic acid/sodium glycodeoxycholate; sodium dodceyl sulfate (SDS); 3-(trimethylsilyl)-1-propanesulfonic acid (DSS); cetrimide (CTAB, the principal component of which is hexadecyltrimethylammonium bromide); hexadecyltrimethylammonium bromide; dodecyltrimethylammonium bromide; hexadecyltrimethyl-ammonium bromide; tetradecyltrimethylammonium bromide; benzyl dimethyldodecylammonium bromide; benzyl dimethylhexadecylammonium chloride; and benzyl dimethyltetra-decylammonium bromide. The above detergents are commercially available from e.g., Sigma Chemical Co., St. Louis, Mo. Various cationic lipids known in the art can also be used as detergents. See Balasubramaniam et al., 1996, *Gene Ther.*, 3:163-72 and Gao, X., and L. Huang. 1995, *Gene Ther.*, 2:7110-722.

The microparticle/detergent mixture is then physically ground, e.g., using a ceramic mortar and pestle, until a smooth slurry is formed. An appropriate aqueous buffer, such as phosphate buffered saline (PBS) or Tris buffered saline, is then added and the resulting mixture sonicated or homogenized until the microparticles are fully suspended. The macromolecule of interest, such as dsRNA or antigen, is then added to the microparticle suspension and the system dialyzed to remove detergent. The polymer microparticles and detergent system are preferably chosen such that the macromolecule of interest will adsorb to the microparticle surface while still maintaining activity of the macromolecule. The resulting microparticles containing surface adsorbed macromolecule may be washed free of unbound macromolecule and stored as a suspension in an appropriate buffer formulation, or lyophilized with the appropriate excipients, as described further below.

Specifically, microparticles manufactured in the presence of charged detergents, such as anionic or cationic detergents, yield microparticles with a charged surface having a net negative or a net positive charge. These microparticles can adsorb a greater variety of molecules. For example, microparticles manufactured with anionic detergents, such as sodium dodecyl sulfate (SDS) or 3-(trimethylsilyl)-1-propanesulfonic acid (DSS), i.e. PLG/SDS or PLG/DSS microparticles, adsorb positively charged antigens, such as proteins. Similarly, microparticles manufactured with cationic detergents, such as CTAB, i.e. PLG/CTAB microparticles, adsorb negatively charged macromolecules, such as dsRNA.

If microparticles and submicron oil-in-water emulsions will be used together, the two are combined using techniques well known in the art. See, e.g., U.S. Pat. No. 6,086,901, incorporated herein by reference in its entirety. Generally, the microparticles and submicron oil-in-water emulsion can be combined by simple mixing, stirring, or shaking. Other techniques, such as passing a mixture of the two components rapidly through a small opening (such as a hypodermic needle) can also be used to provide the adjuvant compositions. If combined, the various components of the composition can be present in a wide range of ratios. For example, the microparticle and emulsion components are typically used in a volume ratio of 1:50 to 50:1, preferably 1:10 to 10:1, more preferably from about 1:3 to 3:1, and most preferably about 1:1. However, other ratios may be more appropriate for specific purposes.

Other particulate antigen delivery systems for use with the present methods and compositions include cationic lipids and liposomes. Various cationic lipids are known in the art and will find use herein. See Balasubramaniam et al., (1996) *Gene Ther.*, 3:163-172 and Gao and Huang (1995) *Gene Ther.*, 2:7110-7122.

Lipid encapsulation with liposomes is generally accomplished using liposomes which are able to stably bind or entrap and retain nucleic acid (in the case of dsRNA) and/or the antigen of interest. The ratio of condensed dsRNA to lipid preparation can vary but will generally be around 1:10 to 1:0.25, such as 1:5 or 1:1 or any integer between these ranges (mg dsRNA:micromoles lipid). For a review of the use of liposomes as carriers for delivery of nucleic acids, see, Hug and Sleight, *Biochim. Biophys. Acta.* (1991) 1097:1-17; Straubinger et al., in *Methods of Enzymology* (1983), Vol. 101, pp. 512-527.

Liposomal preparations for use in the instant invention are generally cationic (positively charged) preparations. Cationic liposomes have been shown to mediate intracellular delivery of plasmid DNA (Felgner et al., *Proc. Natl. Acad. Sci. USA* (1987) 84:7413-7416); mRNA (Malone et al., *Proc. Natl. Acad. Sci. USA* (1989) 86:6077-6081); and purified transcription factors (Debs et al., *J. Biol. Chem.* (1990) 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., *Proc. Natl. Acad. Sci. USA* (1987) 84:7413-7416). Other commercially available lipids include transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194-4198; PCT Publication No. WO 90/11092 for a description of the synthesis of DOTAP (1,2-bis(oleoyloxy)-3-(trimethylammonio)propane) liposomes.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512-527; Szoka et al., *Proc. Natl. Acad. Sci. USA* (1978) 75:4194-4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem.* (1980) 255:10431; Szoka and Papahadjopoulos, *Proc. Natl. Acad. Sci. USA* (1978) 75:145; and Schaefer-Ridder et al., *Science* (1982) 215:166.

Furthermore, other particulate systems and polymers can be used as antigen delivery systems. For example, polymers such as polylysine, polyarginine, polyornithine, spermine, spermidine, as well as conjugates of these molecules, are useful for delivering the dsRNA and an antigen of interest. See, e.g., Felgner, P. L., *Advanced Drug Delivery Reviews* (1990) 5:163-187, for a review of delivery systems useful for gene transfer.

As explained above, ISCOMs are another antigen delivery system useful in the present methods and compositions. ISCOMs for use with the present invention are produced using standard techniques, well known in the art, and are described in e.g., U.S. Pat. Nos. 4,981,684, 5,178,860, 5,679,354 and 6,027,732; European Publ. Nos. EPA 109,942; 180,564 and 231,039; Coulter et al. (1998) *Vaccine* 16:1243. Typically, the term "ISCOM" refers to immunogenic complexes formed between glycosides, such as triterpenoid saponins (particularly Quil A), and antigens which contain a hydrophobic region. See, e.g., European Publ. Nos. EPA 109,942 and 180,564. In this embodiment, the antigen (usually with a hydrophobic region) or type 1 interferon inducer is solubilized in detergent and added to the reaction mixture, whereby ISCOMs are formed with the molecule incorporated therein. However, molecules which lack the desirable hydrophobic properties may be incorporated into the immunogenic complexes after coupling with peptides having hydrophobic amino acids, fatty acid radicals, alkyl radicals and the like.

As explained in European Publ. No. EPA 231,039, the presence of the desired molecule is not necessary in order to form the basic ISCOM structure (referred to as a matrix or ISCOMATRIX), which may be formed from a sterol, such as cholesterol, a phospholipid, such as phosphatidylethanolamine, and a glycoside, such as Quil A. Thus, the molecule of interest, rather than being incorporated into the matrix, is present on the outside of the matrix, for example adsorbed to the matrix via electrostatic interactions. For example, proteins with high positive charge may be electrostatically bound to the ISCOM particles, rather than through hydrophobic forces. For a more detailed general discussion of saponins and ISCOMs, and methods of formulating ISCOMs, see Barr et al. (1998) *Adv. Drug Delivery Reviews* 32:247-271 (1998). The same concepts apply to delivery of dsRNA if desired using ISCOMs.

More particularly, classic ISCOMs are formed by combination of cholesterol, saponin, phospholipid, and immunogens. Classical ISCOM formulations are typically particulates which are approximately 40 nm in diameter and in which the desired molecule is enclosed in a negatively charged, cage-like pentagonal docdecahedral structure composed of saponin, cholesterol and phospholipid (Morein et al. (1984) *Nature* 308:457). ISCOM matrix compositions are formed identically, but without the desired molecule. Molecules with high positive charge may be electrostatically bound in the ISCOM particles, rather than through hydrophobic forces. For a more detailed general discussion of saponins and ISCOMs, and methods of formulating ISCOMs, see Barr et al. (1998) *Adv. Drug Delivery Reviews* 32:247-271 (1998).

The ISCOM matrix may be prepared, for example, by mixing together solubilized sterol, glycoside and (optionally) phospholipid. If phospholipids are not used, two dimensional structures are formed. See, e.g., European Publ. No. EPA 231,039. The term "ISCOM matrix" is used to refer to both the 3-dimensional and 2-dimensional structures. The glycosides to be used are generally glycosides which display amphipathic properties and comprise hydrophobic and hydrophilic regions in the molecule. Preferably saponins are used, such as the saponin extract from *Quillaja saponaria* Molina and Quil A. Other preferred saponins are aescine from *Aesculus hippocastanum* (Patt et al. (1960) *Arzneimittelforschung* 10:273-275 and sapoalbin from *Gypsophilla struthium* (Vochten et al. (1968) *J. Pharm. Belg.* 42:213-226.

In order to prepare the ISCOMs, glycosides are used in at least a critical micelle-forming concentration. In the case of Quil A, this concentration is about 0.03% by weight. The sterols used to produce ISCOMs may be known sterols of animal or vegetable origin, such as cholesterol, lanosterol, lumisterol, stigmasterol and sitosterol. Suitable phospholipids include phosphatidylcholine and phosphatidylethanolamine. Generally, the molar ratio of glycoside (especially when it is Quil A) to sterol (especially when it is cholesterol) to phospholipid is 1:1:0-1, ±20% (preferably not more than ±10%) for each figure. This is equivalent to a weight ratio of about 5:1 for the Quil A:cholesterol.

A solubilizing agent may also be present and may be, for example a detergent, urea or guanidine. Generally, a non-ionic, ionic or zwitter-ionic detergent or a cholic acid based detergent, such as sodium desoxycholate, cholate and CTAB, can be used for this purpose. Examples of suitable detergents include, but are not limited to, octylglucoside, nonyl N-methyl glucamide or decanoyl N-methyl glucamide, alkylphenyl polyoxyethylene ethers such as a polyethylene glycol p-isooctyl-phenylether having 9 to 10 oxyethylene groups (commercialized under the trade name TRITON X-100R™), acylpolyoxyethylene esters such as acylpolyoxyethylene sorbitane esters (commercialized under the trade name TWEEN 20™, TWEEN 80™, and the like). The solubilizing agent is generally removed for formation of the ISCOMs, such as by ultrafiltration, dialysis, ultracentrifugation or chromatography, however, in certain methods, this step is unnecessary. (See, e.g., U.S. Pat. No. 4,981,684).

Generally, the ratio of glycoside, such as QuilA, to antigen by weight is in the range of 5:1 to 0.5:1. Preferably the ratio by weight is approximately 3:1 to 1:1, and more preferably the ratio is 2:1.

As explained above, the adjuvant composition may also contain immunostimulatory molecules, either in addition to or in place of the antigen delivery system. Immunostimulatory agents for use herein include, without limitation, monophosphorylipid A (MPL), trehalose dimycolate (TDM), and cell wall skeleton (CWS), preferably MPL+CWS (Detox™). MPL may be formulated into an emulsion to enhance its immunostimulatory affect. See, e.g., Ulrich et al., "MPLr immunostimulat: adjuvant formulations." in Vaccine Adjuvants: Prepartion Methods and Research Protocols (O'Hagan D T, ed.) Human Press Inc., N.J. (2000) pp. 273-282. MPL has been shown to induce the synthesis and release of cytokines, particularly IL-2 and IFN-γ. Other useful immunostimulatory molecules include LPS and immunostimulatory nucleic acid sequences (ISS), including but not limited to, unmethylated CpG motifs, such as CpG oligonucleotides.

Oligonucleotides containing unmethylated CpG motifs have been shown to induce activation of B cells, NK cells and antigen-presenting cells (APCs), such as monocytes and macrophages. See, e.g., U.S. Pat. No. 6,207,646. Thus, adjuvants derived from the CpG family of molecules, CpG dinucleotides and synthetic oligonucleotides which comprise CpG motifs (see, e.g., Krieg et al. *Nature* (1995) 374:546 and Davis et al. *J. Immunol.* (1998) 160:870-876) such as any of the various immunostimulatory CpG oligonucleotides disclosed in U.S. Pat. No. 6,207,646, may be used in the subject methods and compositions. Such CpG oligonucleotides generally comprise at least 8 up to about 100 basepairs, preferably 8 to 40 basepairs, more preferably 15-35 basepairs, preferably 15-25 basepairs, and any number of basepairs between these values. For example, oligonucleotides comprising the consensus CpG motif, represented by the formula 5'-$X_1CGX_2$-3', where $X_1$ and $X_2$ are nucleotides and C is unmethylated, will find use as immunostimulatory CpG molecules. Generally, $X_1$ is A, G or T, and $X_2$ is C or T. Other useful CpG molecules include those captured by the formula 5'-$X_1X_2CGX_3X_4$, where $X_1$ and $X_2$ are a sequence such as GpT, GpG, GpA, ApA, ApT, ApG, CpT, CpA, CpG, TpA, TpT or TpG, and $X_3$ and $X_4$ are TpT, CpT, ApT, ApG, CpG, TpC, ApC, CpC, TpA, ApA, GpT, CpA, or TpG, wherein "p" signifies a phosphate bond. Preferably, the oligonucleotides do not include a GCG sequence at or near the 5'- and/or 3' terminus. Additionally, the CpG is preferably flanked on its 5'-end with two purines (preferably a GpA dinucleotide) or with a purine and a pyrimidine (preferably, GpT), and flanked on its 3'-end with two pyrimidines, preferably a TpT or TpC dinucleotide. Thus, preferred molecules will comprise the sequence GACGTT, GACGTC, GTCGTT or GTCGCT, and these sequences will be flanked by several additional nucleotides. The nucleotides outside of this central core area appear to be extremely amendable to change.

Moreover, the CpG oligonucleotides for use herein may be double- or single-stranded. Double-stranded molecules are more stable in vivo while single-stranded molecules display enhanced immune activity. Additionally, the phosphate backbone may be modified, such as phosphorodithioate-modified, in order to enhance the immunostimulatory activity of the CpG molecule. As described in U.S. Pat. No. 6,207,646, CpG molecules with phosphorothioate backbones preferentially activate B-cells, while those having phosphodiester backbones preferentially activate monocytic (macrophages, dendritic cells and monocytes) and NK cells.

One exemplary CpG oligonucleotide for use in the present compositions has the sequence 5'-TCCATGACGTTCCT-GACGTT-3' (SEQ ID NO:3).

CpG molecules can readily be tested for their ability to stimulate an immune response using standard techniques, well known in the art. For example, the ability of the molecule to stimulate a humoral and/or cellular immune response is readily determined using the immunoassays described above. Moreover, the antigen and adjuvant compositions can be administered with and without the CpG molecule to determine whether an immune response is enhanced.

If used, the CpG oligonucleotide can be administered either prior to, concurrent with, or subsequent to, delivery of the antigen and/or the adjuvant composition. If administered prior to immunization with the antigen and/or the adjuvant composition, the CpG oligonucleotide can be administered as early as 5-10 days prior to immunization, preferably 3-5 days prior to immunization and most preferably 1-3 or 2 days prior to immunization. If administered separately, the CpG oligonucleotide can be delivered either to the same site of delivery as the antigen and adjuvant composition(s) or to a different delivery site. If simultaneous delivery is desired, the CpG oligonucleotide can be included with the antigen and/or adjuvant composition(s). Generally about 0.5 µg to 1000 µg of the CpG adjuvants will be used, more generally 0.5 µg to about 500 µg, preferably 1 to about 100 µg, preferably about 5 to about 50 µg, preferably 5 to about 30, or any amount within these ranges, of the CpG oligonucleotide per dose, will find use with the present methods.

As explained above, once the adjuvant composition is formulated, it can be administered to the vertebrate subject, either prior to, concurrent with, or subsequent to, delivery of the antigen. If administered prior to immunization with the antigen, the adjuvant formulations can be administered as early as 5-10 days prior to immunization, preferably 3-5 days prior to immunization and most preferably 1-3 or 2 days prior to immunization with the antigens of interest. If administered separately, the adjuvant formulation can be delivered either to the same site of delivery as the antigen compositions or to a different delivery site. Additionally, if the antigen is to be administered separately, it will generally be delivered in a vaccine composition that includes one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles. Moreover, the vaccine compositions can include carriers, additional adjuvants, additional immunostimulatory agents, and so forth, as described below. Delivery is also as described below.

If simultaneous delivery is desired, the antigen can be included with the adjuvant composition. Generally, the antigens and adjuvant can be combined by simple mixing, stirring, or shaking. Other techniques, such as passing a mixture of the two components rapidly through a small opening (such as a hypodermic needle) can also be used to provide the vaccine compositions.

If combined, the various components of the composition can be present in a wide range of ratios. For example, the antigen and emulsion components are typically used in a volume ratio of 1:50 to 50:1, preferably 1:10 to 10:1, more preferably from about 1:3 to 3:1, and most preferably about 1:1. However, other ratios may be more appropriate for specific purposes, such as when a particular antigen has a low immunogenicity, in which case a higher relative amount of the antigen component is required.

Additionally, the compositions can comprise mixtures of one or more antigens, such as antigens derived from more than one viral isolate, as well as additional viral antigens, bacterial antigens, fungal antigens, parasitic antigens and the like. The compositions may also be administered in conjunction with other antigens and immunoregulatory agents, for example, immunoglobulins, cytokines, lymphokines, and chemokines, including but not limited to interferons such as IL-2, modified IL-2 (cys125→ser125), GM-CSF, IL-12, γ-interferon, IP-10, MIP1β, ribavirin and RANTES.

The compositions may include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Such carriers are well known to those of ordinary skill in the art. Furthermore, the antigen may be conjugated to a bacterial toxoid, such as toxoid from diphtheria, tetanus, cholera, etc.

Additional adjuvants may also be present, such as but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837; Chapter 10 in *Vaccine design: the subunit and adjuvant approach*, eds. Powell & Newman, Plenum Press 1995), containing 5% Squalene, 0.5% TWEEN 80™, and 0.5% SPAN 85™ (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% TWEEN 80™, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% TWEEN 80™, and one or more bacterial cell wall components from the group consisting of monophosphorylipid A (MPL), trehalose dimycolate (TDM), and cell wall skeleton (CWS), preferably MPL+CWS (DETOX™); (3) saponin adjuvants, such as QS21 or STIMULON™ (Cambridge Bioscience, Worcester, Mass.) may be used or particles generated therefrom such as ISCOMs (immunostimulating complexes), which ISCOMs may be devoid of additional detergent, see, e.g., International Publication No. WO 00/07621; (4) Complete Freund's Adjuvant (CFA) and Incomplete Freund's Adjuvant (IFA); (5) cytokines, such as interleukins (IL-1, IL-2, IL-4, IL-5, IL-6, IL-7, IL-12 (International Publication No. WO 99/44636), etc.), interferons (e.g., gamma interferon), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. W093/13202 and W092/19265); (7) MPL or 3-O-deacylated MPL (3dMPL) (see, e.g., GB 2220221), EP-A-0689454, optionally in the substantial absence of alum when used with pneumococcal saccharides (see, e.g., International Publication No. WO 00/56358); (8) combinations of 3 dMPL with, for example, QS21 and/or oil-in-water emulsions (see, e.g., EP-A-0835318, EP-A-0735898, EP-A-0761231; (9) oligonucleotides comprising CpG motifs (see, e.g., Roman et al. (1997) *Nat. Med.* 3:849-854; Weiner et al. (1997) *Proc. Natl. Acad. Sci. USA* 94:10833-10837; Davis et al. (1998) *J. Immunol.* 160:870-876; Chu et al. (1997) *J. Exp. Med.* 186:1623-1631; Lipford et al. (1997) *Eur. J. Immunol.* 27:2340-2344; Moldoveanu et al. (1988) *Vaccine* 16:1216-1224; Krieg et al. (1995) *Nature* 374:546-549; Klinman et al. (1996) *Proc. Natl. Acad. Sci. USA* 93:2879-2883; Ballas et al. (1996) *J. Immunol.* 157:1840-1845; Cowdery et al. (1996) *J. Immunol.* 156:4570-4575; Halpern et al. (1996) *Cell Immunol.* 167:72-78; Yamamoto et al. (1988) *Jpn. J. Cancer Res.* 79:866-873; Stacey et al. (1996) *J. Immunol.* 157:2116-2122; Messina et al. (1991) *J. Immunol.* 147:1759-1764; Yi et al. (1996) *J. Immunol.* 157:4918-4925; Yi et al. (1996) *J. Immunol.* 157:5394-5402; Yi et al. (1998) *J. Immunol.* 160:4755-4761; Yi et al. (1998) *J. Immunol.* 160:5898-5906; International Publication Nos. WO 96/02555, WO 98/16247, WO 98/18810, WO 98/40100, WO 98/55495, WO 98/37919 and WO 98/52581), such as those containing at least on CG dinucleotide, with cytosine optionally replaced with 5-methylcytosine; (10) a polyoxyethylene ether or a polyoxyethylene ester (see, e.g., International Publication No. WO 99/52549); (11) a polyoxyethylene sorbitan ester surfactant in combination with an octoxynol (see, e.g., International Publication No. WO 01/21207) or a polyoxyethylene alkyl ether or ester surfactant in combination with at least one additional non-ionic surfactant such as an octoxynol (see, e.g., International Publication No. WO 01/21152); (12) a saponin and an immunostimulatory oligonucleotide such as a CpG oligonucleotide (see, e.g., International Publication No. WO 00/62800); (13) an immunostimulant and a particle of metal salt (see, e.g., International Publication No. WO 00/23105); and (14) other substances that act as immunostimulating agents to enhance the effectiveness of the composition.

Muramyl peptides include, but are not limited to, N-acetyl-muramyl-L-threonyl-D-isoglutamine (thr-MDP), N-acteyl-normuramyl-L-alanyl-D-isogluatme (nor-MDP), -acetylmuramyl-L-alanyl-D-isogluatminyl-L-alanine-2-(1'-2'-dipalmitoyl-sn-glycero-3-huydroxyphosphoryloxy)-ethylamine (MTP-PE), etc.

Typically, the compositions are prepared as injectables, either as liquid solutions or suspensions; solid forms suitable for solution in, or suspension in, liquid vehicles prior to injection may also be prepared.

The compositions will comprise a therapeutically effective amount of the antigen and any other of the above-mentioned components, as needed. By "therapeutically effective amount" is meant an amount of an antigen which will induce an immunological response. Where prophylaxis is desired, preferably a protective immunological response, in the individual to which it is administered will be elicited. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γδ T cell populations.

Once formulated, the compositions are conventionally administered parenterally, e.g., by injection, either intravenously, subcutaneously or intramuscularly. Additional formulations suitable for other modes of administration include oral and pulmonary formulations, suppositories, and transdermal applications. Dosage treatment may be a single dose schedule or a multiple dose schedule. Preferably, the effective amount is sufficient to bring about treatment or prevention of disease symptoms. The exact amount necessary will vary depending on the subject being treated; the age and general condition of the individual to be treated; the capacity of the individual's immune system to synthesize antibodies; the degree of protection desired; the severity of the condition being treated; the particular antigen selected and its mode of administration, among other factors. An appropriate effective amount can be readily determined by one of skill in the art. A "therapeutically effective amount" will fall in a relatively broad range that can be determined through routine trials using in vitro and in vivo models known in the art. The amount of HCV and HIV antigens used in the examples below provides general guidance which can be used to optimize the elicitation of antibodies directed against the particular antigen.

For example, antigen is preferably injected intramuscularly to a large mammal, such as a primate, for example, a baboon, chimpanzee, or human, at a dose of approximately 0.1 µg to about 5.0 mg per dose, or any amount between the stated ranges, such as 0.5 µg to about 1.0 mg, 1 µg to about 500 µg, 2.5 µg to about 250 µg, 4 µg to about 200 µg, such as 2, 4, 5, 6, 7, 8, 10 . . . 20 . . . 30 . . . 40 . . . 50 . . . 60 . . . 70 . . . 80 . . . 90 . . . 100, etc., µg per dose.

Administration of antigen can elicit an antibody titer in the mammal that lasts for at least 1 week, 2 weeks, 1 month, 2 months, 3 months, 4 months, 6 months, 1 year, or longer. Optionally, antibody titers can be maintained in a mammal by providing one or more booster injections of the antigen at 2 weeks, 1 month, 2 months, 3 months, 4 months, 5 months, 6 months, 1 year, or more after the primary injection.

Preferably, an antigen elicits an antibody titer of at least 100, 150, 175, 200, 300, 400, 500, 750, 1,000, 1,500, 2,000, 3,000, 4,000, 5,000, 10,000, 20,000, 30,000, 40,000, 50,000 (geometric mean titer), or higher, or any number between the stated titers, as determined using a standard immunoassay, such as the immunoassay described in the examples below.

Deposits of Strains Useful in Practicing the Invention

A deposit of biologically pure cultures of the following strains was made with the American Type Culture Collection, 10801 University Boulevard, Manassas, Va. The accession number indicated was assigned after successful viability testing, and the requisite fees were paid. made under the provisions of the Budapest Treaty on the International Recognition of the Deposit of Microorganisms for the Purpose of Patent Procedure and the Regulations thereunder (Budapest Treaty). This assures maintenance of viable cultures for a period of thirty (30) years from the date of deposit. The organisms will be made available by the ATCC under the terms of the Budapest Treaty, which assures permanent and unrestricted availability of the progeny to one determined by the U.S. Commissioner of Patents and Trademarks to be entitled thereto according to 35 U.S.C. §122 and the Commissioner's rules pursuant thereto (including 37 C.F.R. §1.12 with particular reference to 886 OG 638). Upon the granting of a patent, all restrictions on the availability to the public of the deposited cultures will be irrevocably removed.

These deposits are provided merely as convenience to those of skill in the art, and are not an admission that a deposit is required under 35 U.S.C. §112. The nucleic acid sequences of these genes, as well as the amino acid sequences of the molecules encoded thereby, are incorporated herein by reference and are controlling in the event of any conflict with the description herein. A license may be required to make, use, or sell the deposited materials, and no such license is hereby granted.

| Plasmid | Deposit Date | ATCC No. |
|---------|--------------|----------|
| E1E2-809 | Aug. 16, 2001 | PTA-3643 |

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Production of HCV E1E2

An HCV E1E2 complex for use in the present vaccine compositions was prepared as a fusion protein as follows. In particular, mammalian expression plasmid pMH-E1E2-809 (FIG. 2, ATCC Deposit No. PTA-3643) encodes an E1E2 fusion protein which includes amino acids 192-809 of HCV 1a (see, Choo et al., Proc. Natl. Acad. Sci. USA (1991) 88:2451-2455).

Chinese Hamster Ovary (CHO) cells were used for expression of the HCV E1E2 sequence from pMH-E1E2-809. In particular, CHO DG44 cells were used. These cells, described by Uraub et al., Proc. Natl. Acad. Sci. USA (1980) 77:4216-4220, were derived from CHO K-1 cells and were made dihydrofolate reductase (dhfr) deficient by virtue of a double deletion in the dhfr gene.

DG44 cells were transfected with pMH-E1E2-809. The transfected cells were grown in selective medium such that only those cells expressing the dhfr gene could grow (Sambrook et al., supra). Isolated CHO colonies were picked (~800 colonies) into individual wells of a 96-well plate. From the original 96-well plates, replicates were made to perform expression experiments. The replicate plates were grown until the cells made a confluent monolayer. The cells were fixed to the wells of the plate and permeablized using cold methanol. Anti-E1 and anti-E2 antibodies, 3D5C3 and 3E5-1 respectively, were used to probe the fixed cells. After adding an anti-mouse HRP conjugate, followed by substrate, the cell lines with the highest expression were determined. The highest expressing cell lines were then expanded to 24-well cluster plates. The assay for expression was repeated, and again, the highest expressing cell lines were expanded to wells of greater volume. This was repeated until the highest expressing cell lines were expanded from 6-well plates into tissue culture flasks. At this point there was sufficient quantity of cells to allow accurate count and harvest of the cells, and quantitative expression assays were done. An ELISA was performed on the cell extract, to determine high expressors.

EXAMPLE 2

Purification of HCV E1E2

Following expression, CHO cells were lysed and the intracellularly produced $E1E2_{809}$ was purified by GNA-lectin affinity chromatography (GNA step), followed by hydroxyapatite (HAP) column chromatography (HAP step), DV50 membrane filtration (DV50 step), SP Sepharose HP column chromatography (SP step), Q membrane filtration (Q step) and G25 Sephadex column chromatography G25 step). At the completion of each of the processing steps, the product pool was either 0.2µ filtered and held at 2-8° C. or processed immediately through the next purification step. At the completion of the purification process, the antigen was 0.2µ filtered and held frozen at −60° C., or lower until filtered for formulation.

Specifically, to lyse the cells, two volumes of chilled lysis buffer (1% Triton X-100 in 100 mM Tris, pH8, and 1 mM EDTA) were added to the CHO cells at 2-8° C. The mixture was centrifuged at 5000 rpm for 45 min at 2-8° C. to remove debris. The supernatant was collected and filtered through a Sartorias 0.65 µm Sartopure prefilter (Sartorius) then a Sartorias 0.65 mm Sartofine prefilter, followed by a Sartorious 0.45 µm Sartobran filter and a 0.2 µm Sartobran filter. The filtered lysate was kept on ice prior to loading on the GNA column.

A GNA agarose column (1885 ml, 200×600, Vector Labs, Burlingame, Calif.) was pre-equilibrated with eight column volumes of equilibration buffer (25 mM $NaPO_4$, 1.0 M NaCl, 12% Triton X-100, pH 6.8) prior to loading. The lysate was applied to the column at 31.4 ml/min (6 cm/hr) over night. The column was washed with 4 bed volumes of equilibration buffer, then washed again with 5 bed volumes of 10 mM $NaPO_4$, 80 mM NaCl, 0.1% Triton X-100, pH 6.8. The product was eluted with 1 M methyl α-D-mannopyranoside (MMP), 10 mM $NaPO_4$, 80 mM NaCl, 0.1% Triton X-100, pH 6.8. The elution peak, about 1 column volume, was collected, 02 µm filtered and stored at or below −60° C. for HAP chromatography.

HAP chromatography was conducted at room temperature. A 1200 ml (100×150 mm) type I ceramic hydroxyapatite column was conditioned with one column volume of 0.4 M $NaPO_4$, pH 6.8, then equilibrated with not less than ten column volumes of 10 mM $NaPO_4$, 80 mM NaCl, 0.1% Triton X-100, pH 6.8. Four lots of GNA eluate pools were thawed in a circulating water bath at not more than 30° C., 0.2 µm filtered and loaded onto the equilibrated column at 131 ml/min (100 cm/hr). HAP equilibration buffer was applied to the column as a chase buffer following the load. The flow-through was collected when UV rose above baseline. The product collection was stopped when the product pool volume reached to a volume of load volume plus 75% of the column volume. The HAP flow-through pool was further processed, by DV50 viral reduction filtration.

DV50 Filtration was conducted at room temperature. DV50 load was prepared by diluting the HAP pool two-fold and adjusting to 0.15% Triton X-100, 1 mM EDTA, pH 5.3. Dilution and adjustment were achieved by adding Dilution Buffer-1 (3 mM citric acid, 2 mM EDTA, 0.2% Triton X-100) to adjust the pH of the product pool to 5.3, followed by addition of Dilution Buffer-2 (2 mM EDTA, 0.2% Triton X-100, pH 5.3) to bring the final volume to 2-fold of the original HAP pool volume.

The diluted and adjusted HAP pool (DV50 Load) was filtered through a 10-inch, Pall Ultipor VF DV50 membrane cartridge (Pall). The filter housing was assembled with filter cartridge, prewetted with water, and sterilized by autoclaving at 123° C. for 60 minutes with slow exhaust prior to use. The filter was then prewetted with SP equilibration buffer (10 mM Sodium Citrate, 1 mM EDTA, 0.15% Triton X-100, pH 5.3), and drained before application of the DV50 load at a pressure not more than 45 psi. DV50 load was subsequently applied with a flux rate of about 800 ml/min at a transmembrane pressure of about 30 psi. The filtrate was collected and stored at 2-8° C. overnight and used in the SP step.

SP chromatography was conducted at room temperature in room. An 88-ml (50×45 mm) SP Sepharose HP column (Pharmacia, Peapack, N.J.) was equilibrated with 15 column volumes of equilibration buffer (10 mM Sodium Citrate, 1 mM EDTA, 0.15% Triton X-100, pH 5.3). The DV50 filtrate was applied to the column. The column was washed first with 5 column volumes of equilibration buffer followed by 20 column volumes of wash buffer containing 10 mM Sodium Citrate, 15 mM NaCl, 1 mM EDTA, 0.1% TWEEN 80™, pH 6.0. Product was eluted from the column with 10 mM Sodium Citrate, 180 mM NaCl, 1 mM EDTA, 0.1% TWEEN 80™, pH 6.0. The entire 280 nm absorption peak was collected as product pool. The product pool was stored at 2-8° C. overnight and used in the Q-membrane filtration step.

The Q-membrane filtration step was conducted at room temperature. Two sterilized Sartorious Q100X disc membranes were connected in series. The membranes were equilibrated with not less than 300 ml of Q equilibration buffer (10 mM Sodium Citrate, 180 mM NaCl, 1 mM EDTA, 0.1% TWEEN 80™, pH 6.0). The entire SP eluate pool was filtered through equilibrated Q membranes at a flow rate of 30-100 ml/min, followed by flushing with 40 ml of Q equilibration buffer. The filtrate and the flush were collected and combined as the product pool and used in the G25 step.

The G25 step was conducted at room temperature. A 1115-ml (100×142 mm) Pharmacia Sephadex G-25 column (Pharmacia, Peapack, N.J.) was equilibrated with not less than five column volumes of formulation buffer (10 mM Sodium Citrate, 270 mM NaCl, 1 mM EDTA, 0.1% TWEEN 80™, pH 6.0). Q filtrate pool was applied to the column and the column flow-through collected, filtered through a 0.22 μm filter (Millipore) and stored frozen at −60° C. or below, until use.

EXAMPLE 3

Use of dsRNA Adjuvant Compositions and HCV Antigens

The ability of dsRNA, in combination with a representative delivery system, to enhance the immunogenicity of HCV $E1E2_{809}$, produced and purified as described above, was determined as follows.

The formulations used in this study are summarized in Table 3. MF59, a representative submicron oil-in-water emulsion which contains 4-5% w/v squalene, 0.5% w/v TWEEN 80™, 0.5% SPAN 85™, was produced as described previously. See, International Publication No. WO 90/14837; U.S. Pat. No. 6,299,884, incorporated herein by reference in its entirety; and Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277-296.

The dsRNA used in these studies was poly[rI-rC], available from Sigma Chemical Co. (St. Louis, Mo.). The dsRNA was reconstituted in RNase-free distilled water and added to the above components at room temperature.

The CpG molecule used was 5'-TCCATGACGTTCCT-GACGTT-3' (SEQ ID NO:3).

The formulations used for all groups included 2.0 μg per dose of the HCV $E1E2_{809}$ antigen, produced as described above.

Balb/C mice were divided into 5 groups (10 mice per group) and administered, intramuscularly a vaccine composition with the components specified in Table 3. Animals were boosted at 30 and 90 days following the initial injection. Serum was collected 14 days following the last injection and anti-E1E2 and anti-E2 antibody titers determined by enzyme immunoassays, as described in Chien et al., *Proc. Natl. Acad. Sci. USA* (1992) 89:10011.

Figure 3:
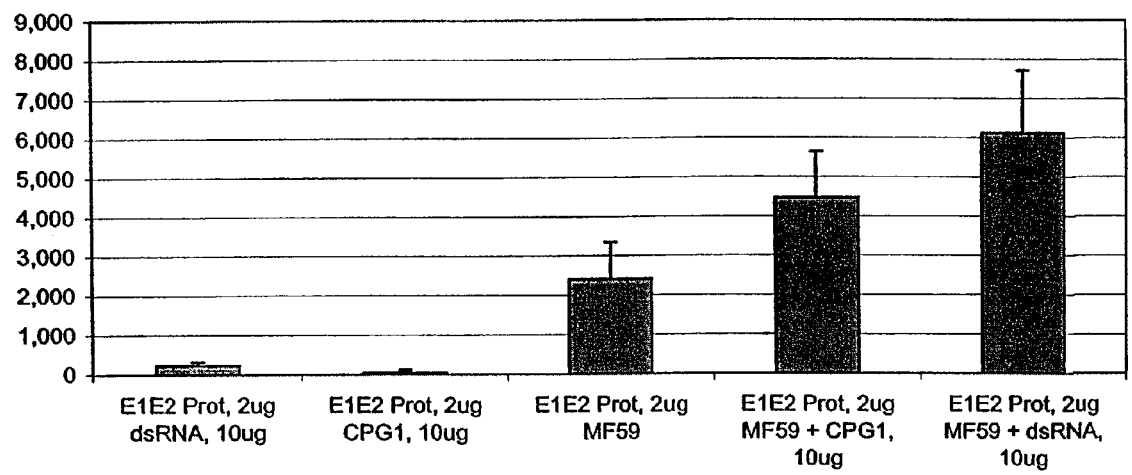
FIG. 3 shows E1E2$_{809}$ anti-E2 IgG antibody titers from mice immunized with E1E2$_{809}$ plus dsRNA; E1E2$_{809}$ plus CpG1; E1E2$_{809}$ plus MF59; E1E2$_{809}$ plus MF59 and CpG1; and E1E2$_{809}$ plus dsRNA and MF59, as described in the examples. Bars show the geometric mean antibody titer (GMT) of the group of 10 mice. The error bars represent standard error of the mean.

The results are shown in Table 3 and FIG. 3. As can be seen, mice immunized with HCV E1E2 using dsRNA combined with MF59 as adjuvant, produced significantly higher (P<0.05) levels of E1E2 antibodies than mice immunized with E1E2 using dsRNA alone, CpG1 alone or MF59 alone as adjuvants. Additionally, antibody titers were higher in the dsRNA+MF59 group than in the group of animals administered CpG+MF59, without dsRNA.

TABLE 3

Immunogenicity of HCV $E1E2_{809}$ using dsRNA and MF59 as adjuvant.

| Group | Formulation | Antigen | Geometric Mean E1E2 EIA Antibody Titer | Standard Error |
|---|---|---|---|---|
| 1 | dsRNA, 10 μg | $E1E2_{809}$, 2 μg | 222 | 95 |
| 2 | CpG1, 10 μg | $E1E2_{809}$, 2 μg | 35 | 80 |
| 3 | MF59 | $E1E2_{809}$, 2 μg | 2407 | 943 |
| 4 | MF59 + CpG1, 10 μg | $E1E2_{809}$, 2 μg | 4477 | 1174 |
| 5 | MF59 + dsRNA, 10 μg | $E1E2_{809}$, 2 μg | 6116 | 1601 |

EXAMPLE 4

Use of dsRNA Adjuvant Compositions and HIV Antigens

The ability of dsRNA, in combination with representative delivery systems, to enhance the immunogenicity of HIV antigens was determined as follows.

4A. In order to test the ability of dsRNA in combination with various delivery systems to enhance the immunogenicity of HIV gp120, the following experiment was done.

The formulations used in this study are summarized in Table 4. MF59, CpG1 and dsRNA are as described above.

HIV gp120 was produced using techniques as previously described. See, e.g., International Publication No. WO 00/39302, describing methods for producing modified gp120 sequences.

PLG/CTAB, another representative delivery system, is a poly (d,l-lactide-co-glycolide) (PLG) microparticle which has been treated with cetrimide (CTAB) to enhance adsorption of dsRNA. The PLG polymers were obtained from Boehringer Ingelheim. The PLG polymer used was RG505, which has a copolymer ratio of 50/50 and a molecular mass of 65 kDa. The PLG/CTAB microparticles were produced as described in Singh et al., *Proc. Natl. Acad. Sci. USA* (2000) 97:811-816. Briefly, cationic microparticles were produced using a modified solvent evaporation process. 10 ml of a 5% (wt/vol) polymer solution was emulsified in methylene chloride with 1 ml PBS at high speed using an Ika homogenizer (Ika-Werk Instruments, Cincinnati, Ohio). The primary emulsion was then added to 50 ml distilled water containing CTAB (0.5% wt/vol). This resulted in the formation of a water/oil/water emulsion that was stirred at 6000 rpm for 12 hours at room temperature, allowing the methylene chloride to evaporate. The resulting micorparticles were washed twice with distilled water by centrifugation at 10,000 g and freeze-dried. Before use, dsRNA was adsorbed to the microparticles by incubating 100 mg of microparticles in 0.2 mg/ml solution (5 ml) of dsRNA at 4° C. for six hours.

PLG/DSS is a PLG microparticle which has been treated with 3-(trimethylsilyl)-1-propanesulfonic acid (DSS) to enhance adsorption of antigen. The PLG/DSS microparticle, with adsorbed gp120 antigen, was produced as described above, with DSS substituted for CTAB. DSS is commercially available from, e.g., Sigma Chemical Co., St. Louis, Mo.

The formulations used for all groups included 10 μg per dose of the HIV gp120 antigen. The PLG/DSS/gp120 microparticles were mixed with dsRNS/PLG/CTAB microparticles with or without the adjuvants indicated and vortexed prior to immunization.

Balb/C mice were divided into 6 groups (10 mice per group) and administered, intramuscularly a vaccine composition with the components specified in Table 4. Animals were boosted at 30 and 90 days following the initial injection. Serum was collected 14 days following the last injection and anti-gp120 antibody titers determined by enzyme immunoassays as described in O'Hagan et al., *J. Virol.* (2001) 75:9037-9043.

The results are shown in Table 4. As can be seen, mice immunized with HIV gp120 using dsRNA combined with MF59 as adjuvant, produced significantly higher (P<0.05) levels of anti-gp120 antibodies than mice immunized with gp120 using dsRNA alone, CpG1 alone or MF59 alone as adjuvants. Additionally, antibody titers were significantly higher in the group of mice administered dsRNA adsorbed to PLG/CTAB microparticles than in the group of animals administered dsRNA alone.

TABLE 4

Immunogenicity of HIV gp120 using dsRNA and MF59 or PLG/CTAB as adjuvant.

| Group | Formulation | Antigen | Geometric Mean gp120 Antibody Titer | Standard Error |
|---|---|---|---|---|
| 1 | PLG/CTAB dsRNA, 10 μg | PLG/DSS/ gp120, 10 μg | 3414 | 1284 |
| 2 | MF59, 10 μg | PLG/DSS/ gp120, 10 μg | 3398 | 745 |
| 3 | MF59 + CpG1,10 μg | PLG/DSS/ gp120, 10 μg | 1943 | 825 |
| 4 | MF59 + dsRNA, 10 μg | PLG/DSS/ gp120, 10 μg | 12,777 | 1624 |
| 5 | dsRNA, 10 μg | PLG/DSS/ gp120, 10 μg | 1898 | 235 |
| 6 | CpG1, 10 μg | PLG/DSS/ gp120, 10 μg | 26 | 29 |

4B. In order to test the ability of dsRNA in combination with various delivery systems to enhance the immunogenicity of HIV p55gag, the following experiment was done.

The formulations used in this study are summarized in Table 5. MF59, CpG1, PLG/DSS and dsRNA are as described above.

HIV p55gag was produced as previously described. See, e.g., International Publication No. WO 00/39302, describing methods for producing modified p55gag sequences. The PLG/DSS/p55gag microparticles were produced as described above with p55gag substituted for gp120.

The formulations used for all groups included 10 μg per dose of the HIV p55gag antigen.

Balb/C mice were divided into 5 groups (10 mice per group) and administered, intramuscularly a vaccine composition with the components specified in Table 5. Animals were boosted at 30 and 90 days following the initial injection. Serum was collected 14 days following the last injection and anti-p55gag antibody titers determined by enzyme immunoassays as described in Kazzaz et al., *J. Cont. Del.* (2000) 67:347-356.

Figure 4:
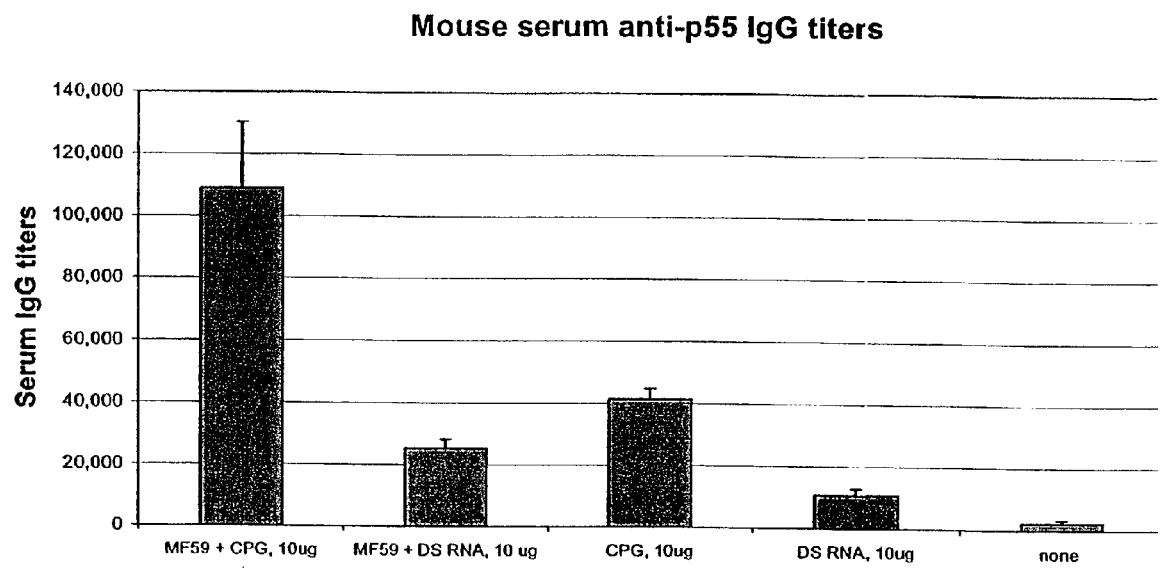
FIG. 4 shows anti-p55gag IgG antibody titers from mice immunized with p55gag plus MF59 and CpG1, 10 µg; p55gag plus MF59 and dsRNA, 10 µg; p55 plus CpG1, 10 µg; and dsRNA, 10 µg (alone), as described in the examples. Bars show the geometric mean antibody titer (GMT) of the group of 10 mice. The error bars represent standard error of the mean.

The results are shown in Table 5 and FIG. 4. As can be seen, mice immunized with HIV p55gag using dsRNA combined with CpG1, with and without MF59, as well as those immunized with dsRNA combined with MF59, produced significantly higher (P<0.05) levels of anti-P55gag antibodies than mice immunized with p55gag using dsRNA alone.

TABLE 5

Immunogenicity of HIV p55gag using dsRNA and MF59 as adjuvant.

| Group | Formulation | Antigen | Geometric Mean p55gag Antibody Titer | Standard Error |
|---|---|---|---|---|
| 1 | MF59 + CpG1, 10 μg | PLG/DSS/ p55gag, 10 μg | 109,046 | 21,294 |
| 2 | MF59 + dsRNA, 10 μg | PLG/DSS/ p55gag, 10 μg | 25,361 | 2881 |
| 3 | CpG1, 10 μg | PLG/DSS/ p55gag, 10 μg | 41,443 | 3460 |
| 4 | dsRNA, 10 μg | PLG/DSS/ p55gag, 10 μg | 10,798 | 2122 |
| 5 | none | PLG/DSS p55gag, 10 μg | 2341 | 936 |

EXAMPLE 5

Use of dsRNA Adjuvant Compositions and Meningococcal Antigens

The ability of dsRNA, in combination with representative delivery systems, to enhance the immunogenicity of Meningococcal antigens, was determined as follows.

5A. The formulations used in this study are summarized in Tables 6 and 7. PLG/CTAB, PLG/DSS, CpG1, MF59 and dsRNA are as described above. Additionally, for some of the groups (as indicated in the tables), CpG1 was adsorbed to the microparticles.

The Meningococcal antigens used were Meningococcal B (MenB) proteins 287 and 961. These proteins are described in International Publication No. WO 99/57280, incorporated herein by reference in its entirety. The dose of each antigen given was 20 μg per immunization. These antigens were also adsorbed to PLG/DSS microparticles using the protocol described above.

Balb/C mice were divided into 10 groups (10 mice per group) and administered, intramuscularly a vaccine composition with the components specified in Tables 6 and 7. Animals were boosted at 21 and 35 days following the initial injection. Serum was collected 14 days following the second injection (at the time of the second boost) and 14 days following the last injection and anti-287 and 961 antibody titers determined by enzyme immunoassays. The titers specified represent the reciprocal serum dilution given and O.D. 0.5 at 450 nm.

The results are shown in Tables 6 and 7. As can be seen, mice immunized with PLG/MenB 961 using PLG/dsRNA, produced significantly higher levels of anti-961 antibodies than mice immunized with PLG/MenB 961 alone. Additionally, anti-961 antibody titers were significantly higher in the group of mice administered PLG/dsRNA plus PLG/287 and PLG/961 than in the group of animals administered PLG/287 and PLG/961 without dsRNA.

TABLE 6

Immunogenicity of MenB 961 using various adjuvants.

| Group | Formulation | Geometric Mean MenB 961 Antibody Titer | Standard Error |
|---|---|---|---|
| 1 | PLG/DSS/961 | 3818 | 1019 |
| 2 | PLG/DSS/961 + CpG1, 10 μg | 14,149 | 2588 |

TABLE 6-continued

Immunogenicity of MenB 961 using various adjuvants.

| Group | Formulation | Geometric Mean MenB 961 Antibody Titer | Standard Error |
|---|---|---|---|
| 3 | PLG/DSS/961 + PLG/CpG1, 10 μg | 18,536 | 9491 |
| 4 | PLG/DSS/961 + PLG/CTAB dsRNA, 10 μg | 24,321 | 3452 |
| 5 | 961 + CFA/IFA | 50,453 | 19,415 |

TABLE 7

Immunogenicity of MenB 961 + MenB 287 using various adjuvants.

| Group | Formulation | Geometric Mean MenB 287 Antibody Titer | Standard Error MenB 287 | Geometric Mean MenB 961 Antibody Titer | Standard Error MenB 961 |
|---|---|---|---|---|---|
| 6 | PLG/287 + PLG/961 | 13,557 | 5180 | 2476 | 817 |
| 7 | PLG/287 + PLG/961 + CpG1, 10 μg | 21,664 | 10,256 | 6557 | 4297 |
| 8 | PLG/287 + PLG/961 + PLG/CpG1, 10 μg | 27,259 | 5062 | 7510 | 3365 |
| 9 | PLG/287 + PLG/961 + CpG1, 10 μg + MF59 | 27,981 | 5502 | 26,826 | 5613 |
| 10 | PLG/287 + PLG/961 + PLG/dsRNA, 10 μg | 13,525 | 2807 | 7324 | 2163 |

5B. The formulations used in this study are summarized in Table 8. The MenB 961 and 287 proteins, MF59 and dsRNA are as described above. Additionally, for some of the groups (as indicated in the tables), alum and Complete Freund's Adjuvant (CFA) were used in the formulations. None of the compositions included PLG.

Balb/C mice were divided into 5 groups and administered and boosted with vaccine compositions with the components specified in Table 8, as described above. Serum was collected and assayed using anti-961 antibodies, as described above.

The results are shown in Table 8. As can be seen, mice immunized with MenB 961+287, in combination with alum and dsRNA produced significantly higher levels of anti-961 antibodies than mice immunized with alum and MenB 961+287 without dsRNA. Antibody titers in mice immunized with MenB 961+287, in combination with MF59 and dsRNA likewise displayed higher titers than mice immunized with MenB 961+287 with MF59 in the absence of dsRNA.

TABLE 8

Immunogenicity of MenB 961 using various adjuvants.

| Group | Formulation | Geometric Mean MenB 961 Antibody Titer | Standard Error |
|---|---|---|---|
| 1 | alum 961 + 287 | 5197 | 5198 |
| 2 | alum 961 + 287 + dsRNA | 29,409 | 7683 |
| 3 | CFA 961 + 287 | 36,752 | 26,457 |
| 4 | 961 + 287 + MF59 + dsRNA | 4176 | 799 |
| 5 | 961 + 287 + MF59 | 90 | 352 |

EXAMPLE 6

Activity of Poly[rI-rC]

A synthetic polyriboinosinic-polyribocytidylic acid (poly[rI-rC]) dsRNA 90mer was synthesized. This dsRNA included a 90mer strand of riboinosinic acid and a 90mer strand of ribocytidylic acid annealed thereto. The synthetic dsRNA was tested for its ability to stimulate TNF and IL-12 p40 production by human peripheral blood mononuclear cells in vitro. Results shown were from 4 donors and the compound was tested at a final concentration of 100 μg/ml. Activity was between 20 and 70% of heterogeneous poly[rI-rC] samples. Thus, the synthetic dsRNA derivative displayed in vitro activity.

| Donor | TNF-alpha (pg/ml) | IL-12 p40 (pg/ml) |
|---|---|---|
| 1 | 24 | 41 |
| 2 | 36 | 22 |
| 3 | 62 | 90 |
| 4 | 92 | 140 |

Accordingly, novel adjuvant compositions and methods of using the same are disclosed. From the foregoing, it will be appreciated that, although specific embodiments of the invention have been described herein for purposes of illustration, various modifications may be made without departing from the spirit and the scope of the invention as defined by the appended claims.

The invention claimed is:

1. A composition comprising: (1) dsRNA, wherein the dsRNA is polyriboinosinic-polyribocytidylic acid (poly[rI-rC]), polyriboguanylic-polyribocytidylic acid (poly[rG-rC]) or polyriboadenylic-polyribouridylic acid (poly[rA-rU]); and (2) an HCV E1E2 polypeptide that comprises a sequence of amino acids with at least 90% sequence identity to the contiguous sequence of amino acids depicted at positions 20-637 of SEQ ID NO:2, with the proviso that the HCV E1E2 polypeptide comprises the amino acid sequence of SEQ ID NO:4 at a position corresponding to amino acids 218-238 of SEQ ID NO:2, wherein said polypeptide elicits an immune response against HCV, wherein said dsRNA and/or said HCV E1E2 polypeptide are adsorbed to a microparticle, and further wherein the immune response to the composition is increased as compared to the immune response to a composition comprising the HCV E1E2 polypeptide without the dsRNA and/or the microparticle.

2. The composition of claim 1, wherein the dsRNA is poly[rI-rC].

3. The composition of claim 2, wherein the microparticle comprises a polymer selected from the group consisting of a poly(α-hydroxy acid), a polyhydroxy butyric acid, a polycaprolactone, a polyorthoester, and a polyanhydride.

4. The composition of claim 3, wherein the microparticle comprises poly(D,L-lactide-co-glycolide) (PLG).

5. The composition of claim 4, wherein the polypeptide is adsorbed to the microparticle.

6. The composition of claim 4, wherein the dsRNA is adsorbed to the microparticle.

7. The composition of claim 5, wherein the dsRNA is adsorbed to the microparticle.

8. The composition of claim 1, wherein the microparticle comprises 3-(trimethylsilyl)-1-propanesulfonic acid (DSS).

9. The composition of claim 1, wherein the microparticle comprises hexadecyl trimethyl ammonium bromide (CTAB).

* * * * *

SEQUENCE LISTING

```
<160> NUMBER OF SEQ ID NOS: 5
<210> SEQ ID NO 1
<211> LENGTH: 1914
<212> TYPE: DNA
<213> ORGANISM: Artificial Sequence
<220> FEATURE:
<221> NAME/KEY: CDS
<222> LOCATION: (1)..(1911)
<220> FEATURE:
```

<223> OTHER INFORMATION: Description of Artificial Sequence: HCV-1
     E1/E2/p7 region

<400> SEQUENCE: 1

```
tct

```
            290                 295                 300
gga agc ggc ccc gac cag cgc ccc tac tgc tgg cac tac ccc cca aaa     960
Gly Ser Gly Pro Asp Gln Arg Pro Tyr Cys Trp His Tyr Pro Pro Lys
305                 310                 315                 320 cct tgc ggt att gtg ccc gcg aag agt gtg tgt ggt ccg gta tat tgc    1008
Pro Cys Gly Ile Val Pro Ala Lys Ser Val Cys Gly Pro Val Tyr Cys
                325                 330                 335 ttc act ccc agc ccc gtg gtg gtg gga acg acc gac agg tcg ggc gcg    1056
Phe Thr Pro Ser Pro Val Val Val Gly Thr Thr Asp Arg Ser Gly Ala
            340                 345                 350 ccc acc tac agc tgg ggt gaa aat gat acg gac gtc ttc gtc ctt aac    1104
Pro Thr Tyr Ser Trp Gly Glu Asn Asp Thr Asp Val Phe Val Leu Asn
        355                 360                 365 aat acc agg cca ccg ctg ggc aat tgg ttc ggt tgt acc tgg atg aac    1152
Asn Thr Arg Pro Pro Leu Gly Asn Trp Phe Gly Cys Thr Trp Met Asn
370                 375                 380 tca act gga ttc acc aaa gtg tgc gga gcg cct cct tgt gtc atc gga    1200
Ser Thr Gly Phe Thr Lys Val Cys Gly Ala Pro Pro Cys Val Ile Gly
385                 390                 395                 400 ggg gcg ggc aac aac acc ctg cac tgc ccc act gat tgc ttc cgc aag    1248
Gly Ala Gly Asn Asn Thr Leu His Cys Pro Thr Asp Cys Phe Arg Lys
                405                 410                 415 cat ccg gac gcc aca tac tct cgg tgc ggc tcc ggt ccc tgg atc aca    1296
His Pro Asp Ala Thr Tyr Ser Arg Cys Gly Ser Gly Pro Trp Ile Thr
            420                 425                 430 ccc agg tgc ctg gtc gac tac ccg tat agg ctt tgg cat tat cct tgt    1344
Pro Arg Cys Leu Val Asp Tyr Pro Tyr Arg Leu Trp His Tyr Pro Cys
        435                 440                 445 acc atc aac tac act ata ttt aaa atc agg atg tac gtg gga ggg gtc    1392
Thr Ile Asn Tyr Thr Ile Phe Lys Ile Arg Met Tyr Val Gly Gly Val
450                 455                 460 gag cac agg ctg gaa gct gcc tgc aac tgg acg cgg ggc gaa cgt tgc    1440
Glu His Arg Leu Glu Ala Ala Cys Asn Trp Thr Arg Gly Glu Arg Cys
465                 470                 475                 480 gat ctg gaa gat agg gac agg tcc gag ctc agc ccg tta ctg ctg acc    1488
Asp Leu Glu Asp Arg Asp Arg Ser Glu Leu Ser Pro Leu Leu Leu Thr
                485                 490                 495 act aca cag tgg cag gtc ctc ccg tgt tcc ttc aca acc ctg cca gcc    1536
Thr Thr Gln Trp Gln Val Leu Pro Cys Ser Phe Thr Thr Leu Pro Ala
            500                 505                 510 ttg tcc acc ggc ctc atc cac ctc cac cag aac att gtg gac gtg cag    1584
Leu Ser Thr Gly Leu Ile His Leu His Gln Asn Ile Val Asp Val Gln
        515                 520                 525 tac ttg tac ggg gtg ggg tca agc atc gcg tcc tgg gcc att aag tgg    1632
Tyr Leu Tyr Gly Val Gly Ser Ser Ile Ala Ser Trp Ala Ile Lys Trp
530                 535                 540 gag tac gtc gtc ctc ctg ttc ctt ctg ctt gca gac gcg cgc gtc tgc    1680
Glu Tyr Val Val Leu Leu Phe Leu Leu Leu Ala Asp Ala Arg Val Cys
545                 550                 555                 560 tcc tgc ttg tgg atg atg cta ctc ata tcc caa gcg gaa gcg gct ttg    1728
Ser Cys Leu Trp Met Met Leu Leu Ile Ser Gln Ala Glu Ala Ala Leu
                565                 570                 575 gag aac ctc gta ata ctt aat gca gca tcc ctg gcc ggg acg cac ggt    1776
Glu Asn Leu Val Ile Leu Asn Ala Ala Ser Leu Ala Gly Thr His Gly
            580                 585                 590 ctt gta tcc ttc ctc gtg ttc ttc tgc ttt gca tgg tat ctg aag ggt    1824
Leu Val Ser Phe Leu Val Phe Phe Cys Phe Ala Trp Tyr Leu Lys Gly
        595                 600                 605 aag tgg gtg ccc gga gcg gtc tac acc ttc tac ggg atg tgg cct ctc    1872
```

```
Lys Trp Val Pro Gly Ala Val Tyr Thr Phe Tyr Gly Met Trp Pro Leu
            610                 615                 620 ctc ctg ctc ctg ttg gcg ttg ccc cag cgg gcg tac gcg taa           1914
Leu Leu Leu Leu Leu Ala Leu Pro Gln Arg Ala Tyr Ala
625                 630                 635

<210> SEQ ID NO 2
<211> LENGTH: 637
<212> TYPE: PRT
<213> ORGANISM: Artificial Sequence
<220> FEATURE:
<223> OTHER INFORMATION: Description of Artificial Sequence: HCV-1
      E1/E2/p7 region

<400> SEQUENCE: 2

Ser Phe Ser Ile Phe Leu Leu Ala Leu Leu Ser Cys Leu Thr Val Pro
  1               5                  10                  15

Ala Ser Ala Tyr Gln Val Arg Asn Ser Thr Gly Le

-continued

```
                    325                 330                 335
    Phe Thr Pro Ser Pro Val Val Gly Thr Thr Asp Arg Ser Gly Ala
                340                 345                 350
    Pro Thr Tyr Ser Trp Gly Glu Asn Asp Thr Asp Val Phe Val Leu Asn
                355                 360                 365
    Asn Thr Arg Pro Pro Leu Gly Asn Trp Phe Gly Cys Thr Trp Met Asn
                370                 375                 380
    Ser Thr Gly Phe Thr Lys Val Cys Gly Ala Pro Pro Cys Val Ile Gly
    385                 390                 395                 400
    Gly Ala Gly Asn Asn Thr Leu His Cys Pro Thr Asp Cys Phe Arg Lys
                    405                 410                 415
    His Pro Asp Ala Thr Tyr Ser Arg Cys Gly Ser Gly Pro Trp Ile Thr
                420                 425                 430
    Pro Arg Cys Leu Val Asp Tyr Pro Tyr Arg Leu Trp His Tyr Pro Cys
                435                 440                 445
    Thr Ile Asn Tyr Thr Ile Phe Lys Ile Arg Met Tyr Val Gly Gly Val
                450                 455                 460
    Glu His Arg Leu Glu Ala Ala Cys Asn Trp Thr Arg Gly Glu Arg Cys
    465                 470                 475                 480
    Asp Leu Glu Asp Arg Asp Arg Ser Glu Leu Ser Pro Leu Leu Leu Thr
                    485                 490                 495
    Thr Thr Gln Trp Gln Val Leu Pro Cys Ser Phe Thr Thr Leu Pro Ala
                500                 505                 510
    Leu Ser Thr Gly Leu Ile His Leu His Gln Asn Ile Val Asp Val Gln
                515                 520                 525
    Tyr Leu Tyr Gly Val Gly Ser Ser Ile Ala Ser Trp Ala Ile Lys Trp
                530                 535                 540
    Glu Tyr Val Val Leu Leu Phe Leu Leu Leu Ala Asp Ala Arg Val Cys
    545                 550                 555                 560
    Ser Cys Leu Trp Met Met Leu Leu Ile Ser Gln Ala Glu Ala Ala Leu
                    565                 570                 575
    Glu Asn Leu Val Ile Leu Asn Ala Ala Ser Leu Ala Gly Thr His Gly
                580                 585                 590
    Leu Val Ser Phe Leu Val Phe Phe Cys Phe Ala Trp Tyr Leu Lys Gly
                595                 600                 605
    Lys Trp Val Pro Gly Ala Val Tyr Thr Phe Tyr Gly Met Trp Pro Leu
                610                 615                 620
    Leu Leu Leu Leu Leu Ala Leu Pro Gln Arg Ala Tyr Ala
    625                 630                 635

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: CpG1

<400> SEQUENCE: 3
tccatgacgt tcctgacgtt                                                  20

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: consensus
      sequence
```

<400> SEQUENCE: 4

Gly Ser Ala Ala Arg Thr Thr Ser Gly Phe Val Ser Leu Phe Ala Pro
 1               5                  10                  15

Gly Ala Lys Gln Asn
            20

<210> SEQ ID NO 5
<211> LENGTH: 9781
<212> TYPE: DNA
<213> ORGANISM: Artificial Sequence
<220> FEATURE:
<223> OTHER INFORMATION: Description of Artificial Sequence: HIV Type C
      8_5_TV1_C.ZA

<400> SEQUENCE: 5

| | |
|---|---|
| tggaagggtt aatttactcc aagaaaaggc aagaaatcct tgatttgtgg gtctatcaca | 60 |
| cacaaggctt cttccctgat ggcaaaact acacaccggg gccagggtc agatatccac | 120 |
| tgacctttgg atggtgctac aagctagtgc cagttgaccc aggggaggtg aagaggcca | 180 |
| acggaggaga agacaactgt ttgctacacc ctatgagcca acatgagca gaggatgaag | 240 |
| atagagaagt attaaagtgg aagtttgaca gcctcctagc acgcagacac atggcccgcg | 300 |
| agctacatcc ggagtattac aaagactgct gacacagaag gactttccg cctgggactt | 360 |
| tccactgggg cgttccggga ggtgtggtct gggcgggact gggagtggt caaccctcag | 420 |
| atgctgcata taagcagctg cttttcgcct gtactgggtc tctctcggta gaccagatct | 480 |
| gagcctggga gccctctggc tatctaggga acccactgct taagcctcaa taaagcttgc | 540 |
| cttgagtgct ttaagtagtg tgtgcccatc tgttgtgtga ctctggtaac tagagatccc | 600 |
| tcagaccctt tgtggtagtg tggaaaatct ctagcagtgg cgcccgaaca gggaccagaa | 660 |
| agtgaaagtg agaccagagg agatctctcg acgcaggact cggcttgctg aagtgcacac | 720 |
| ggcaagaggc gagaggggcg gctggtgagt acgccaattt tacttgacta gcggaggcta | 780 |
| gaaggagaga gatgggtgcg agagcgtcaa tattaagcgg cggaaaatta gataaatggg | 840 |
| aaagaattag gttaaggcca ggggaaaga acattatat gttaaaacat ctagtatggg | 900 |
| caagcaggga gctggaaaga tttgcactta accctggcct gttagaaaca tcagaaggct | 960 |
| gtaaacaaat aataaaacag ctacaaccag ctcttcagac aggaacagag gaacttagat | 1020 |
| cattattcaa cacagtagca actctctatt gtgtacataa agggatagag gtacgagaca | 1080 |
| ccaaggaagc cttagacaag atagaggaag aacaaaacaa atgtcagcaa aaagcacaac | 1140 |
| aggcaaaagc agctgacgaa aaggtcagtc aaaattatcc tatagtacag aatgcccaag | 1200 |
| ggcaaatggt acaccaagct atatcaccta gaacattgaa tgcatggata aaagtaatag | 1260 |
| aggaaaaggc tttcaatcca gaggaaatac ccatgtttac agcattatca gaaggagcca | 1320 |
| ccccacaaga tttaaacaca atgttaaata cagtgggggg acatcaagca gccatgcaaa | 1380 |
| tgttaaaaga taccatcaat gaggaggctg cagaatggga taggacacat ccagtacatg | 1440 |
| cagggcctgt tgcaccaggc cagatgagag aaccaagggg aagtgacata gcaggaacta | 1500 |
| ctagtaccct tcaggaacaa atagcatgga tgacaagtaa tccacctatt ccagtagaag | 1560 |
| acatctataa aagatggata attctggggt taaataaaat agtaagaatg tatagccctg | 1620 |
| ttagcatttt ggacataaaa caagggccaa agaacccctt tagagactat gtagaccggt | 1680 |
| tctttaaaac cttaagagct gaacaagcta cacaagatgt aaagaattgg atgacagaca | 1740 |
| ccttgttggt ccaaaatgcg aacccagatt gtaagaccat tttaagagca ttaggaccag | 1800 |

-continued

```
gggcctcatt agaagaaatg atgacagcat gtcagggagt gggaggacct agccataaag    1860
caagagtgtt ggctgaggca atgagccaag caaacagtaa catactagtg cagagaagca    1920
attttaaagg ctctaacaga attattaaat gtttcaactg tggcaaagta gggcacatag    1980
ccagaaattg cagggcccct aggaaaaagg gctgttggaa atgtggacag aaggacacc     2040
aaatgaaaga ctgtactgag aggcaggcta attttttagg gaaaatttgg ccttcccaca    2100
aggggaggcc agggaatttc ctccagaaca gaccagagcc aacagcccca ccagcagaac    2160
caacagcccc accagcagag agcttcaggt tcgaggagac aaccccgtg ccgaggaagg     2220
agaaagagag ggaacccttta acttccctca aatcactctt tggcagcgac cccttgtctc   2280
aataaaagta gagggccaga taaggaggc tctcttagac acaggagcag atgatacagt     2340
attagaagaa atagatttgc cagggaaatg gaaaccaaaa atgatagggg gaattggagg    2400
ttttatcaaa gtaagacagt atgatcaaat acttatagaa atttgtggaa aaaggctat     2460
aggtacagta ttagtagggc ctacaccagt caacataatt ggaagaaatc tgttaactca    2520
gcttggatgc acactaaatt ttccaattag tcctattgaa actgtaccag taaaattaaa    2580
accaggaatg gatggcccaa aggtcaaaca atggccattg acagaagaaa aataaaagc     2640
attaacagca atttgtgagg aaatggagaa ggaaggaaaa attacaaaaa ttgggcctga    2700
taatccatat aacactccag tatttgccat aaaaaagaag gacagtacta agtggagaaa    2760
attagtagat ttcagggaac tcaataaaag aactcaagac ttttgggaag ttcaattagg    2820
aataccacac ccagcaggat taaaaagaa aaaatcagtg acagtgctag atgtggggga    2880
tgcatatttt tcagttcctt tagatgaaag cttcaggaaa tatactgcat tcaccatacc    2940
tagtataaac aatgaaacac cagggattag atatcaatat aatgtgctgc cacagggatg    3000
gaaaggatca ccagcaatat tccagagtag catgacaaaa atcttagagc ccttcagagc    3060
aaaaaatcca gacatagtta tctatcaata tatggatgac ttgtatgtag gatctgactt    3120
agaaataggg caacatagag caaaaataga gagttaagg gaacatttat tgaaatgggg    3180
atttacaaca ccagacaaga aacatcaaaa agaaccccca tttctttgga tggggtatga    3240
actccatcct gacaaatgga cagtacaacc tatactgctg ccagaaaagg atagttggac    3300
tgtcaatgat atacagaagt tagtgggaaa attaaactgg gcaagtcaga tttacccagg    3360
gattaaagta aggcaactct gtaaactcct caggggggcc aaagcactaa cagacatagt    3420
accactaact gaagaagcag aattagaatt ggcagagaac agggaaattt taagagaacc    3480
agtacatgga gtatattatg atccatcaaa agacttgata gctgaaatac agaaacaggg    3540
gcatgaacaa tggacatatc aaatttatca agaccatttt aaaaatctga aaacagggaa    3600
gtatgcaaaa atgaggacta cccacactaa tgatgtaaaa cagttaacag aggcagtgca    3660
aaaaatagcc atgaaagca tagtaatatg gggaaagact cctaaattta gactacccat     3720
ccaaaaagaa acatgggaga catggtggac agactattgg caagccacct ggatccctga    3780
gtgggagttt gttaataccc ctcccctagt aaaattatgg taccaactag aaaaagatcc    3840
catagcagga gtagaaactt tctatgtaga tggagcaact aatagggaag ctaaaatagg    3900
aaaagcaggg tatgttactg acagaggaag gcagaaaatt gttactctaa ctaacacaac    3960
aaatcagaag actgagttac aagcaattca gctagctctg caggattcag gatcagaagt    4020
aaacatagta acagactcac agtatgcatt aggaatcatt caagcacaac cagataagag    4080
tgactcagag atatttaacc aaataataga acagttaata aacaaggaaa gaatctacct    4140
```

```
gtcatgggta ccagcacata aaggaattgg gggaaatgaa caagtagata aattagtaag    4200
taagggaatt aggaaagtgt tgtttctaga tggaatagat aaagctcaag aagagcatga    4260
aaggtaccac agcaattgga gagcaatggc taatgagttt aatctgccac ccatagtagc    4320
aaaagaaata gtagctagct gtgataaatg tcagctaaaa ggggaagcca tacatggaca    4380
agtcgactgt agtccaggga tatggcaatt agattgtacc catttagagg gaaaaatcat    4440
cctggtagca gtccatgtag ctagtggcta catggaagca gaggttatcc cagcagaaac    4500
aggacaagaa acagcatatt ttatattaaa attagcagga agatggccag tcaaagtaat    4560
acatacagac aatggcagta attttaccag tactgcagtt aaggcagcct gttggtgggc    4620
aggtatccaa caggaatttg gaattcccta caatccccaa agtcaggag tggtagaatc     4680 catgaataaa gaattaaaga aaataatagg acaagtaaga gatcaagctg agcaccttaa    4740
gacagcagta caaatggcag tattcattca caattttaaa agaaaagggg gaattggggg    4800
gtacagtgca ggggaaagaa taatagacat aatagcaaca gacatacaaa ctaaagaatt    4860
acaaaaacaa attataagaa ttcaaaattt tcgggtttat tacagagaca gcagagaccc    4920
tatttggaaa ggaccagccg aactactctg gaaaggtgaa ggggtagtag taatagaaga    4980
taaaggtgac ataaaggtag taccaaggag gaaagcaaaa atcattagag attatggaaa    5040
acagatggca ggtgctgatt gtgtggcagg tggacaggat gaagattaga gcatggaata    5100
gtttagtaaa gcaccatatg tatatatcaa ggagagctag tggatgggtc tacagacatc    5160
attttgaaag cagacatcca aaagtaagtt cagaagtaca tatcccatta ggggatgcta    5220
gattagtaat aaaaacatat tggggtttgc agacaggaga aagagattgg catttgggtc    5280
atggagtctc catagaatgg agactgagag aatacagcac acaagtagac cctgacctgg    5340
cagaccagct aattcacatg cattattttg attgttttac agaatctgcc ataagacaag    5400
ccatattagg acacatagtt tttcctaggt gtgactatca agcaggacat aagaaggtag    5460
gatctctgca atacttggca ctgacagcat tgataaaacc aaaaaagaga aagccacctc    5520
tgcctagtgt tagaaaatta gtagaggata gatggaacga ccccagaag accaggggcc    5580 gcagagggaa ccatacaatg aatggacact agagattcta gaagaactca agcaggaagc    5640
tgtcagacac tttcctagac catggctcca tagcttagga caatatatct atgaaaccta    5700
tggggatact tggacgggag ttgaagctat aataagagta ctgcaacaac tactgttcat    5760
tcatttcaga attggatgcc aacatagcag aataggcatc ttgcgacaga gaagagcaag    5820
aaatggagcc agtagatcct aaactaaagc cctggaacca tccaggaagc caacctaaaa    5880
cagcttgtaa taattgcttt tgcaaacact gtagctatca ttgtctagtt tgctttcaga    5940
caaaaggttt aggcatttcc tatggcagga agaagcggag acagcgacga agcgctcctc    6000
caagtggtga agatcatcaa aatcctctat caaagcagta agtacacata gtagatgtaa    6060
tggtaagttt aagtttattt aaaggagtag attatagatt aggagtagga cattgatag     6120 tagcactaat catagcaata atagtgtgga ccatagcata tatagaatat aggaaattgg    6180
taagacaaaa gaaaatagac tggttaatta aagaattag ggaaagagca gaagacagtg     6240
gcaatgagag tgatggggac acagaagaat tgtcaacaat ggtggatatg gggcatctta    6300
ggcttctgga tgctaatgat ttgtaacacg gaggacttgt gggtcacagt ctactatggg    6360
gtacctgtgt ggagagaagc aaaaactact ctattctgtg catcagatgc taaagcatat    6420
gagacagaag tgcataatgt ctgggctaca catgcttgtg tacccacaga ccccaaccca    6480
caagaaatag ttttgggaaa tgtaacagaa aattttaata tgtggaaaaa taacatggca    6540
```

```
gatcagatgc atgaggatat aatcagttta tgggatcaaa gcctaaagcc atgtgtaaag   6600
ttgaccccac tctgtgtcac tttaaactgt acagatacaa atgttacagg taatagaact   6660
gttacaggta atacaaatga taccaatatt gcaaatgcta catataagta tgaagaaatg   6720
aaaaattgct ctttcaatgc aaccacagaa ttaagagata agaaacataa agagtatgca   6780
ctcttttata aacttgatat agtaccactt aatgaaaata gtaacaactt acatatagaa   6840
ttaataaatt gcaataccte aaccataaca caagcctgtc caaggtctc ttttgacccg    6900
attcctatac attactgtgc tccagctgat tatgcgattc taaagtgtaa aataagaca    6960
ttcaatggga caggaccatg ttataatgtc agcacagtac aatgtacaca tggaattaag   7020
ccagtggtat caactcaact actgttaaat ggtagtctag cagaagaagg ataataatt    7080
agatctgaaa atttgacaga aataccaaa acaataatag tacatcttaa tgaatctgta    7140
gagattaatt gtacaaggcc caacaataat acaaggaaaa gtgtaaggat aggaccagga   7200
caagcattct atgcaacaaa tgacgtaata ggaaacataa gacaagcaca ttgtaacatt   7260
agtacagata gatggaataa aactttacaa caggtaatga aaaaattagg agagcatttc   7320
cctaataaaa caataaaatt tgaaccacat gcaggagggg atctagaaat tacaatgcat   7380
agctttaatt gtagaggaga atttttctat tgcaatacat caaacctgtt taatagtaca   7440
tactaccccta agaatggtac atacaaatac aatggtaatt caagcttacc catcacactc   7500
caatgcaaaa taaaacaaat tgtacgcatg tggcaagggg taggacaagc aatgtatgcc   7560
cctcccattg caggaaacat aacatgtaga tcaaacatca caggaatact attgacacgt   7620
gatgggggat ttaacaacac aaacaacgac acagaggaga cattcagacc tggaggagga   7680
gatatgaggg ataactggag aagtgaatta tataaatata agtggtaga aattaagcca    7740
ttgggaatag cacccactaa ggcaaaaaga agagtggtgc agagaaaaaa aagagcagtg   7800
ggaataggag ctgtgttcct tgggttcttg ggagcagcag gaagcactat gggcgcagcg   7860
tcaataacgc tgacggtaca ggccagacaa ctgttgtctg gtatagtgca acagcaaagc   7920
aatttgctga aggctataga ggcgcaacag catatgttgc aactcacagt ctggggcatt   7980
aagcagctcc aggcgagagt cctggctata gaaagatacc taaaggatca acagctccta   8040
gggatttggg gctgctctgg aagactcatc tgcaccactg ctgtgccttg gaactccagt   8100
tggagtaata atctgaagc agatatttgg gataacatga cttggatgca gtgggataga   8160
gaaattaata attacacaga aacaatattc aggttgcttg aagactcgca aaaccagcag   8220
gaaaagaatg aaaaagattt attagaattg gacaagtgga ataatctgtg gaattggttt   8280
gacatatcaa actggctgtg gtatataaaa atattcataa tgatagtagg aggcttgata   8340
ggtttaagaa taattttttgc tgtgctctct atagtgaata gagttaggca gggatactca   8400
cctttgtcat ttcagaccct tacccaagc ccgaggggac tcgacaggct cggaggaatc    8460
gaagaagaag gtggagagca agacagagac agatccatac gattggtgag cggattcttg   8520
tcgcttgcct gggacgatct gcggagcctg tgcctcttca gctaccaccg cttgagagac   8580
ttcatattaa ttgcagtgag ggcagtggaa cttctggac acagcagtct cagggactaa   8640
cagagggggt gggagatcct taagtatctg ggaagtcttg tgcagtattg ggtctagag    8700
ctaaaaaaga gtgctattag tccgcttgat accatagcaa tagcagtagc tgaaggaaca   8760
gataggatta tagaattggt acaaagaatt tgtagagcta tcctcaacat acctaggaga   8820
ataagacagg gctttgaagc agctttgcta taaaatggga ggcaagtggt caaaacgcag   8880
```

```
                                -continued
catagttgga tggcctgcag taagagaaag aatgagaaga actgagccag cagcagaggg  8940
agtaggagca gcgtctcaag acttagatag acatggggca cttacaagca gcaacacacc  9000
tgctactaat gaagcttgtg cctggctgca agcacaagag gaggacggag atgtaggctt  9060
tccagtcaga cctcaggtac ctttaagacc aatgacttat aagagtgcag tagatctcag  9120
cttcttttta aaagaaaagg ggggactgga agggttaatt tactctagga aaaggcaaga  9180
aatccttgat ttgtgggtct ataacacaca aggcttcttc cctgattggc aaaactacac  9240 atcgggggcca ggggtccgat tcccactgac ctttggatgg tgcttcaagc tagtaccagt  9300
tgacccaagg gaggtgaaag aggccaatga aggagaagac aactgtttgc tacaccctat  9360
gagccaacat ggagcagagg atgaagatag agaagtatta aagtggaagt ttgacagcct  9420
tctagcacac agacacatgg cccgcgagct acatccggag tattacaaag actgctgaca  9480
cagaagggac tttccgcctg ggactttcca ctggggcgtt ccgggaggtg tggtctgggc  9540
gggacttggg agtggtcacc ctcagatgct gcatataagc agctgctttt cgcttgtact  9600
gggtctctct cggtagacca gatctgagcc tgggagctct ctggctatct agggaaccca  9660
ctgcttaggc ctcaataaag cttgccttga gtgctctaag tagtgtgtgc ccatctgttg  9720
tgtgactctg gtaactagag atccctcaga ccctttgtgg tagtgtggaa aatctctagc  9780
a                                                                  9781
```